(12) United States Patent
Ghannoum

(10) Patent No.: US 12,233,097 B2
(45) Date of Patent: *Feb. 25, 2025

(54) COMPOSITIONS AND METHODS FOR PROMOTING A HEALTHY MICROBIAL FLORA IN A MAMMAL

(71) Applicant: BIOHM Health Inc., Cleveland, OH (US)

(72) Inventor: Afif Ghannoum, Moreland Hills, OH (US)

(73) Assignee: BIOHM Health Inc., Cleveland, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/690,879

(22) Filed: Mar. 9, 2022

(65) Prior Publication Data

US 2022/0296662 A1 Sep. 22, 2022

Related U.S. Application Data

(62) Division of application No. 16/468,053, filed as application No. PCT/US2018/021794 on Mar. 9, 2018, now Pat. No. 11,304,985.

(60) Provisional application No. 62/556,016, filed on Sep. 8, 2017, provisional application No. 62/470,060, filed on Mar. 10, 2017.

(51) Int. Cl.

| | |
|---|---|
| *A61K 36/064* | (2006.01) |
| *A23L 31/00* | (2016.01) |
| *A23L 33/135* | (2016.01) |
| *A61K 9/00* | (2006.01) |
| *A61K 9/19* | (2006.01) |
| *A61K 9/48* | (2006.01) |
| *A61K 9/50* | (2006.01) |
| *A61K 35/00* | (2006.01) |
| *A61K 35/745* | (2015.01) |
| *A61K 35/747* | (2015.01) |
| *A61K 38/47* | (2006.01) |
| *A61P 31/04* | (2006.01) |
| *A61P 31/10* | (2006.01) |

(52) U.S. Cl.
CPC ............ *A61K 36/064* (2013.01); *A23L 31/00* (2016.08); *A23L 33/135* (2016.08); *A61K 9/0053* (2013.01); *A61K 9/0056* (2013.01); *A61K 9/19* (2013.01); *A61K 9/4808* (2013.01); *A61K 9/5047* (2013.01); *A61K 35/745* (2013.01); *A61K 35/747* (2013.01); *A61K 38/47* (2013.01); *A61P 31/04* (2018.01); *A61P 31/10* (2018.01); *C12Y 302/01001* (2013.01); *A23V 2002/00* (2013.01); *A23V 2400/113* (2023.08); *A23V 2400/175* (2023.08); *A23V 2400/519* (2023.08); *A61K 2035/115* (2013.01)

(58) Field of Classification Search
CPC .. A61K 36/064; A61K 9/0053; A61K 9/0056; A61K 9/19; A61K 9/4808; A61K 9/5047; A61K 35/745; A61K 35/747; A61K 38/47; A61K 2035/115; A61K 35/741; A23L 31/00; A23L 33/135; C12Y 302/01001; A23V 2002/00; A23V 2400/113; A23V 2400/175; A23V 2400/519

See application file for complete search history.

(56) References Cited

U.S. PATENT DOCUMENTS

| | | | |
|---|---|---|---|
| 4,678,673 | A | 7/1987 | Marshall et al. |
| 6,759,040 | B1 | 7/2004 | Manyak et al. |
| 8,722,035 | B2 | 5/2014 | Porubcan |
| 11,304,985 | B2 | 4/2022 | Ghannoum |
| 2006/0251633 | A1 | 11/2006 | Salvadori et al. |
| 2009/0202516 | A1 | 8/2009 | Olmstead |
| 2010/0291050 | A1 | 11/2010 | Dalkeler et al. |
| 2012/0034200 | A1 | 9/2012 | Porubcan |

(Continued)

FOREIGN PATENT DOCUMENTS

| | | |
|---|---|---|
| AU | 2015100952 A | 8/2015 |
| AU | 2015100952 A4 * | 8/2015 |

(Continued)

OTHER PUBLICATIONS

Braz. Arch. Biol. Technol. v.56 n.1: pp. 113-119, Jan./Feb. 2013. (Year: 2013).*

Giang H H, Viet T Q, Lindberg J E and Ogle B 2010: Effects of microbial enzymes and a complex of lactic acid bacteria and *Saccharomyces boulardii* on growth performance and total tract digestibility in weaned pigs. Livestock Research for Rural Development. vol. 22, Article #179. (Year: 2010).*

(Continued)

*Primary Examiner* — Kade Ariani

(74) *Attorney, Agent, or Firm* — Eschweiler & Potashnik, LLC

(57) ABSTRACT

The disclosure provides compositions and dosage forms for promoting healthy microbial flora in a mammal, for example, a human. The disclosure further provides compositions and dosage forms for disrupting biofilm or preventing formation of biofilm containing pathogenic bacteria and/or pathogenic fungi in a particular region of a subject. The dosage forms contain (i) an isolated non-pathogenic fungal strain that is viable in the region of the subject, (ii) an isolated non-pathogenic bacterial strain that is viable in the region of the subject, and optionally (iii) an enzyme capable of disrupting the biofilm. The present disclosure also provides methods of disrupting a biofilm or preventing formation of a biofilm with such a composition or dosage form, methods of identifying a subject suitable for treatment with such a composition or dosage form, and methods of improving nutrient absorption using such a composition or dosage form.

20 Claims, 18 Drawing Sheets

(56) References Cited

U.S. PATENT DOCUMENTS

| | | |
|---|---|---|
| 2012/0252775 A1 | 10/2012 | Finegold |
| 2012/0315249 A1 | 12/2012 | Olmstead |
| 2012/0315260 A1 | 12/2012 | Ivanova et al. |
| 2013/0209374 A1 | 8/2013 | Castellana |
| 2013/0266539 A1 | 10/2013 | Borody |
| 2014/0037688 A1 | 2/2014 | Berkes et al. |
| 2015/0010670 A1 | 1/2015 | Mills et al. |
| 2016/0206564 A1 | 7/2016 | Trachtman |
| 2017/0020137 A1 | 1/2017 | Reilly |
| 2018/0325117 A1 | 11/2018 | Holmes |
| 2019/0381119 A1 | 12/2019 | Ghannoum |
| 2021/0030818 A1 | 2/2021 | Ghannoum |

FOREIGN PATENT DOCUMENTS

| | | | |
|---|---|---|---|
| CN | 109200065 A1 | 1/2019 | |
| CN | 109288874 A1 | 2/2019 | |
| CN | 110664848 A1 | 1/2020 | |
| CN | 111073828 A1 | 4/2020 | |
| JP | 2002-522393 A5 | 7/2002 | |
| JP | 2002-531510 A | 9/2002 | |
| JP | 2008-515809 A | 5/2008 | |
| JP | 2012-515167 B2 | 7/2012 | |
| JP | 2013-511555 A5 | 4/2013 | |
| WO | 2000007606 A2 | 2/2000 | |
| WO | 200029007 A1 | 5/2000 | |
| WO | 00033854 A1 | 6/2000 | |
| WO | 2003071883 A1 | 9/2003 | |
| WO | WO-2006041930 A2 * | 4/2006 | ........... A61K 31/355 |
| WO | 2009100456 A2 | 8/2009 | |
| WO | 2010081126 A2 | 7/2010 | |
| WO | 2011063394 A2 | 5/2011 | |
| WO | 2012110778 A2 | 8/2012 | |
| WO | 2012170915 A1 | 12/2012 | |
| WO | 2017/204788 A1 | 11/2017 | |
| WO | 2018165576 A1 | 9/2018 | |
| WO | WO-2019/173763 A1 | 9/2019 | |
| WO | 2022266469 A1 | 12/2022 | |

OTHER PUBLICATIONS

Sara Massironi, Roberta Elisa Rossi, Federica Alessandra Cavalcoli, Serena Della Valle, Mirella Fraquelli, Dario Conte, Nutritional deficiencies in inflammatory bowel disease: Therapeutic approaches, Clinical Nutrition (2013) vol. 32, Issue 6, p. 904-910. doi.org/10.1016/j.clnu.2013.03.020. (Year: 2013).*

Agazzi, "The benficial role of probiotics in monogastric animal nutrition and health", Journal of Dairy, Veterinary & Animal Research, 2015, 2(4): 116-132.

Bisson et al."Preventative Effects of Different Probiotic Formulations on Travelers' Diarrhea Model on Wistar Rats", Dig. Dis. Sci., 2010, Springer Science, 55: 911-919.

Bull et al., "The life history of *Lactobacillus acidophilus* as a probiotic: a tale of revisionary taxonomy, misidentification and commercial success," FEMS Microbiol Lett, 2013, 349: 77-87.

Cruz-Cordova et al., "CS21 positive multidrug-resistant ETEC clinical isolates from children with diarrhea are associated with self-aggregation, and adherence," Frontiers in Microbiology, 2014, 5(709): 1-10.

De Marco et al., "Antibiofilm and antiadhesive activities of dfferent synbiotics," Journal of Probiotics & Health, 2017, 5(3): 1-9.

Grape Chia Kombucha Published Nov. 2015 [retrieved from internet on Jun. 1, 2018]. <URL: http://www.gnpd.com/sinatra/recordpage/3543799/from_search/U0zmwg9NrN/?page=1.

Hoarau et al. "Bacteriome and Mycobiome Interactions Underscore Microbial Dysbiosis in Familial Crohn's Disease," mBio, 2016, 7(5): e01250-16.

Mohamed et al., "Association of putative enteroaggressive *Escherichia coli* virulence genes and biofilm production in isolates from travelers to developing countries," Journal of Clinical Microbiology, 2007, 45(1): 121-126.

Sanders et al., "Food formats for effective delivery of probiotics", Annual Review of Food Science and Technology, 2010, 1(1): 65-85.
Trends in Biotechnology, 2015, vol. 33, No. 9, pp. 496-503.
Journal of the Japanese Society of Chemotherapy, 2017, vol. 66, No. 1, pp. 129-138.
Appl Microbiol Biotechnol, 2016, vol. 100, pp. 6415-6426.
Biochemical and Biophysical Research, 2009, vol. 379, pp. 324-329.
Japanese Office Action dated Aug. 23, 2023 in connection with Application Serial No. 2020-547144.
Canadian Office Action dated Oct. 24, 2023 in connection with Application Serial No. 3,055,915.
Mahmoud A. Ghannoum; Evaluation of Microbiome Alterations Following Consumption of BIOHM, a Novel Probiotic (Journal Publication in Current Issues in Molecular Biology) Curr. Issues Mol. Biol. 2021, 43, 2135-2146. https://doi.org/10.3390/cimb43030148.
Ghannoum M; The Probiotic Biohm Improves Nutrient Absorption by Disrupting Gastrointestinal Biofilms (Journal Publication in Journal of Probiotics & Health); J Prob Health, vol. 7 Iss.2 No. 213; Aug. 7, 2019.
Ghannoum M; BIOHM Probiotics Retain Viability in Low pH Environments Simulating the Digestive Environment (Journal Publication in Journal of Probiotics & Health); J Prob Health, vol. 7 Iss.1 No. 1000211; Aug. 7, 2019.
Christopher L. Hager; Effects of a Novel Probiotic Combination on Pathogenic Bacterial-Fungal Polymicrobial Biofilms (Journal Publication in American Society of Microbiology (mBio)); Mar./Apr. 2019 vol. 10 Issue 2 e00338-19.
Ghannoum M; Effect of Mycobiome Diet on Gut Fungal and Bacterial Communities of Healthy Adults (Journal Publication in Journal of Probiotics & Health); J Prob Health, vol. 7 Iss.4 No. 215; Dec. 31, 2019.
G. Hoarau; Bacteriome and Mycobiome Interactions Underscore Microbial Dysbiosis in Familial Crohn's Disease (Journal Publication in American Society of Microbiology (mBio)); Sep./Oct. 2016 vol. 7 Issue 5 e01250-16.
Luca Di Martino; A Novel Probiotic Combination Ameliorates Crohn's Disease-Like Ileitis by Increasing Short-Chain Fatty Acid Production and Modulating Essential Adaptive Immune Pathways (Journal Publication in Inflammatory Bowel Diseases); Inflammatory Bowel Diseases, 2023, XX, 1-13; https://doi.org/10.1093/ibd/izac284.
Rachael Gowen; Modulating the Microbiome for Disease Treatment (Journal Publication in Gastroenterology); Gastroenterology 2023; https://doi.org/10.1053/j.gastro.2023.01.017.
M.B. La Monica; A Probiotic Amylase Blend Reduces Gastrointestinal Symptoms in a Randomized Clinical Study (Journal Publication in Beneficial Microbes); Oct. 23, 2023; DOI: 10.1163/18762891-20230043.
Mauricio Retuerto; Probiotic Supplementation of Pea-Derived Protein alters the gut microbiome balance in favor of increased protein degradation, reflected in increased levels of Essential Amino Acid in Human Plasma (Journal Publication in Gastroenterology & Hepatology); vol. 14 Issue 4-2023.
Bisson et al. "Preventive Effects of Different Probiotic Formulations on Travelers' Diarrhea Model on Wistar Rats," Dig. Dis. Sci., 2010, Springer Science, 55: 911-919.
Extended European Search Report for corresponding European Application No. 18764573.4 dated Dec. 21, 2020.
Findley et al. "Human Skin Fungal Diversity," Nature, 2013, 498(7454):1-16.
Ghannoum. "Cooperative Evolutionary Strategy between the Bacteriome and Mycobiome," mBio, 2016, 7(6): e01951-16.
Grape Chia Kombucha Published Nov. 2015 [Retrieved from internet on Jun. 1, 2018]. <URL: http://www.gnpd.com/sinatra/recordpage/3543799/from_search/Uzmwg9NrN/?page=1>.
Harikrishnan et al. "Immunomodulatory effect of probiotics enriched diets on Uronema marinum infected olive flounder," Fish & Shellfish Immunology, 2011, 30(1): 964-971.
Hoarau et al. "Bacteriome and Mycobiome Interactions Underscore Microbial Dysbiosis in Familial Chron's Disease," mBio, 2016, 7(5): e01250-16.

(56) References Cited

OTHER PUBLICATIONS

International Search Report and Written Opinion for International Application No. PCT/US2018/021794 dated Jun. 12, 2018.
International Search Report and Written Opinion for International Application No. PCT/US2019/021437 dated Jul. 5, 2019.
Light Formula Oven Baked Biscuits for Dogs Published Mar. 2012 [retrieved from internet on Jun. 1, 2018] <URL: http://www.gnpd.com/sinatra/recordpage/1735611/from_search/KTVgNLzvVe/?page=1>.
Mukherjee et al. "Oral Mycobiome Analysis of HIV-Infected Patients: Identification of Pichia as an Antagonist of Opportunistic Fungi," PLOS Pathogens, 2014, 10(3): e1003996.
Probiotics, Prebiotics & Enzymes Supplement for Pets Published May 2013 [retrieved from internet on Jun. 1, 2018]. <URL: http://www.gnpd.com/sinatra/recordpage/2058301/from_search/OLOK8PskIX/?page=1>.
Trilogy Kombucha Published Dec. 2015 [retrieved from internet on Jun. 1, 2018]. <URL: http://www.gnpd.com/sinatra/recordpage/3544057/from_search/U0zmwg9NrN/?page=1>.
Ultimate Probiotic Formula Supplement Published Sep. 2015 [retrieved from internet on Jun. 1, 2018]. <URL: http://www.gnpd.com/sinatra/recordpage/3358667/from_search/3Br2sCBSzh/?page=1>.
Agazzi, "The beneficial role of probiotics in monogastric animal nutrition and health", Journal of Dairy, Veterinary & Animal Research, 2015, 2(4): 116-132.
Ann et al., "Microencapsulation of lactobacillus acidophilus ATCC 43121 with prebiotic substrates using a hybridisation system," International Journal of Food Science and Technology, 2007, 42: 411-419.
ATCC Product Sheet (ATCC 39595), 2021.
Bruggencate et al., "The effect of a multi-strain probiotic on the reistance toward *Escherichia coli* challenge in a randomized, placebo-controlled, double-blind intervention study," European Journal of Clinical Nutrition, 2015, 69: 385-391.
Bull et al., "The life history of Lactobacillus acidophilus as probiotic: a tale of revisionary taxonomy, misidentification and commercial success," FEMS Microbiol Lett, 2013, 349: 77-87.
Cruz-Cordova et al., "CS21 positive multidrug-resistant ETEC clinical isolates from children with diarrhea are associated with self-aggression, and adherence," Frontiers in Microbiology, 2014, 5(709): 1-10.
De Marco et al., "Antibiofilm and antiadhesive activities of different synbiotic," Journal of Probiotics & Health, 2017, 5(3): 1-9.
Douillard et al., "Comparative Genomic and Functional Analysis of 100 Lactobacillus rhamnosus Strains and Their Comparison with Strain GG," 2013, PLoS Genet 9(8): e1003683.
Extended European Search Report for Corresponding European Application No. 19764245.7 dated Feb. 11, 2022.
Iannitti et al., "Therapeutical use of probiotic formulations in clinical practice", Clinical Nutrition, 2010, 29(6): 701-725.
Mohamed et al., "Association of putative enteroaggresive *Escherichia coli* virulence genes and biofilm production in isolates from travelers to developing countries," Journal of Clinical Microbiology, 2007, 45(1): 121-126.
Sanders et al., "Food formats for effective delivery of probiotics", Annual Review of Food Science and Technology, 2010, 1(1): 66-85.
Vandini et al., "Hard surface biocontrol in hospitals using microbial-based cleaning products," PLoS ONE, 2014, 9(9): 1-13.
Woo et al., "Probiotic-mediated competition, exclusion and displacement in biofil formation by food-borne pathogens," Letters in Applied Microbiology, 2013, 56: 307-313.
Santocchi et al., "Effects of Probiotic supplementation on gastrointestinal, sensory and core symptoms in autism spectrum disorders: a randomized controlled trial", Frontiers in Psychiatry, 2020, 11: 1-12.
Grossi et al., Unexpected improvement in core autism spectrum disorder symptoms after long-term treatment with probiotics:, SAGE Open Medical Case Reports, 2016, 4: 1-5.
Arnold et al., Probiotics for gastrointestinal symptoms and quality of life in autism: a placebo-controlled pilot trial, Journal of Child and Adolescent Psychopharmacology:, 2019, 29 (9): 659-669.
Kim et al., "Oxidative Stress in Inflammation-based Gastrointestinal Tract Diseases: Challenges and Opportunities", J of Gastroenterology and Hepatology, 2012, 27(6): 1004-1010.
Shin et al., "Proteobacteria: Microbial Signature of Dysbiosis in Gut Microbiota", Trends Biotechnol., 2015, 33(9): 496-503.
Matsubara, Victor Haruo et al., "Probiotic Lactobacilli inhibit early stages of Candida Albicans biofilm development by reducing their growth, cell adhesion, and filamentation." Appl. Microbiol. Biotechnol., 2016, 100(14):6415-6426.
Kim et al., "Released exopolysaccharide (r-EPS) produced from probiotic bacteria reduce biofilm formation of enterohemorrhagic *Escherichia coli* O157:H7," Biochemical and Biophysical Research Communications, 2009, 379(2); 324-329.
2011; Sartor RB. Efficacy of probiotics for the management of inflammatory bowel disease. J Gastroenterol Hepatol (NY). 2011;7(9): 606-608.
2007; Edwards-Ingram L, Gitsham P, Burton N, Warhurst G, Clarke I, David H, et al. Genotypic and Physiological Characterization of *Saccharomyces boulardii*, the probiotic strain of *Saccharomyces cerevisiae*. App Environ Microbiol 2007;73(8):2458-2467.
2019; Hager CL, Isham N, Schrom KP, et al. Effects of a Novel Probiotic Combination on Pathogenic Bacterial-Fungal Polymicrobial Biofilms. mBio. 2019;10(2).
2010; Murzyn, A., et al., Capric acid secreted by *S. boulardii* inhibits C. albicans filamentous growth, adhesion and biofilm formation. PLoS One, 2010. 5(8): p. e12050.
Non-Final Office Action for U.S. Appl. No. 16/979,459, dated Jul. 31, 2024, 20 pages.
Japanese Office Action dated Mar. 12, 2024 in connection with Application Serial No. 2020-547144.
Zampieri, G., et al. "Multi-dimensional experimental and computational exploration of metabolism pinpoints complex probiotic interactions," Metabolic Engineering, vol. 76, 2023, pp. 120-132, ISSN 1096-7176.
Non-Final Office Action for U.S. Appl. No. 16/979,459, dated May 31, 2022, 12 pages.
Non-Final Office Action for U.S. Appl. No. 16/979,459, dated Nov. 15, 2022, 16 pages.
Final Office Action for U.S. Appl. No. 16/979,459, dated Mar. 14, 2023, 25 pages.
Non-Final Office Action for U.S. Appl. No. 16/979,459, dated Sep. 25, 2023, 34 pages.
Final Office Action for U.S. Appl. No. 16/979,459, dated Mar. 22, 2024, 35 pages.

\* cited by examiner 1000 x MAGNIFICATION

PROBIOTIC BACTERIA CLUMP TOGETHER AND PREVENT FUNGAL HYPHENATION 3250 x MAGNIFICATION

PROBIOTIC BACTERIA CLUMP TOGETHER AND PREVENT FUNGAL HYPHENATION 500 x MAGNIFICATION   FUNGAL HYPHENATION IS SIGNIFICANTLY REDUCED UPON TREATMENT WITH THE PROBIOTIC FILTRATE 1000 x MAGNIFICATION

FUNGAL HYPHENATION IS SIGNIFICANTLY REDUCED UPON TREATMENT WITH THE PROBIOTIC FILTRATE

COMPOSITIONS AND METHODS FOR PROMOTING A HEALTHY MICROBIAL FLORA IN A MAMMAL

CROSS-REFERENCE TO RELATED APPLICATIONS

This application is a divisional of U.S. patent application Ser. No. 16/468,053, filed on Jun. 10, 2019, which is a U.S. national stage application, filed under 35 U.S.C. § 371, of International Application No. PCT/US2018/021794, filed on Mar. 9, 2018, which claims the benefit of and priority to U.S. Provisional Patent Application No. 62/470,060, filed on Mar. 10, 2017, and U.S. Provisional Patent Application No. 62/556,016, filed on Sep. 8, 2017, the contents of each of which are hereby incorporated by reference in their entireties for all purposes.

FIELD OF THE INVENTION

The present invention relates generally to compositions and methods for promoting a healthy microbial flora in a mammal. The invention further relates to compositions and methods for disrupting a biofilm comprising pathogenic bacteria and/or pathogenic fungi in a subject, and more specifically relates to a composition comprising: (i) one or more non-pathogenic fungal strains, (ii) one or more non-pathogenic bacterial strains and (iii) an optional enzyme capable of disrupting the biofilm, methods of treating a subject with such a composition, and methods of identifying subject suitable for treatment with such a composition.

BACKGROUND

Biofilms are formed when unicellular microorganisms live together and form a community that is protected by an exopolysaccharide (EPS) matrix. This EPS matrix typically is a conglomeration of proteins, polysaccharides and extracellular DNA. Biofilm-associated microorganisms differ from their planktonic (freely suspended) counterparts. It is believed that biofilm-forming cells co-aggregate with each other to form coordinated groups attached to a biotic or abiotic surface, the cells are surrounded by a protective EPS matrix, communicate effectively through quorum sensing, and have low metabolic activity that limits the impact of conventional antimicrobials (both antifungal and anti-bacterial agents) acting against actively metabolizing cells or cells in stationary phase.

Microorganisms, including bacteria, fungi, and archaea form biofilms. For a given subject (e.g., a human) many microorganisms (termed microbiota) exist on or within various regions of said subject, e.g., the gut, the skin, the vagina, the respiratory tract, and the mouth. There is an inextricable link between a host subject's gastrointestinal microbiota and digestion, immunity and metabolism. Gastrointestinal microbiota are important for vitamin and metabolites biosynthesis and digestion of complex macromolecules such as polysaccharides. Gastrointestinal microbiota, under normal conditions, aid in prevention of colonization of pathogenic microorganisms and in maintaining the integrity and function of the intestinal barrier and supporting the immune system.

However, undesirable or unbalanced biofilms may be involved in a significant percentage of human microbial infections (Potera, C. (1999) SCIENCE 283:1837-8). It has been proposed that four criteria define biofilm etiology during an infection include whether the pathogenic bacteria or fungi are surface associated or adherent to a substratum; whether the bacteria are in clusters, encased in a matrix of bacterial, fungal or host constituents; whether the infection is localized; and whether the infection is resistant to antibiotic and anti-fungal therapies despite the antimicrobial sensitivity of the constituent planktonic organisms (Parsek, M. R. & Singh, P. K. (2003) ANN REV. MICROBIAL. 57:677-701; Ghannoum, M., et al. (2015) MICROBIAL BIOFILMS. Second Ed., Am. Soc. for Microbiology).

It is believed that biofilm-based infections are involved in the etiology of dental caries, periodontal disease, cystic fibrosis (CF) airway infections, native valve endocarditis, chronic bacterial prostatitis, otitis media, and vaginal infections. Biofilm microorganisms may also be involved in implant-related infections, in which adherent microbial (including bacteria and fungi) populations form on the surfaces of catheters, prosthetic heart valves, joint replacements, and other devices (Donlan, R. M. (2001) EMERG. INFECT. DIS. 7:277-81; Chandra, J. and Ghannoum M. A. (2004) FUNGAL BIOFILMS., Ch. 3. In: MICROBIAL BIOFILMS. O'Toole G and Ghannoum MA (Editors)).

The intestinal tract provides a reservoir for many antibiotic-resistant biofilm fungi and bacteria, including *Candida* species, Enterobacteriaceae species, *Pseudomonas aeruginosa*, and *Acinetobacter* species (Donskey, C. J. (2004) CLIN. INFECT. DIS. 39:219-26). Although the lungs have traditionally been considered to be a major site of *P. aeruginosa* infection among critically ill patients, a significant number of these infections arise as a result of direct contamination of the airways by the gastrointestinal flora or by hematogenous dissemination from the intestines to the lung parenchyma. Effective methods for the inhibition, reduction and/or treatment of *P. aeruginosa* would have a significant impact for this condition.

With respect to biofilms in the gut, it is now believed that bacteria and fungi can exist for example as biofilms on the colonic epithelium, within the mucus layer covering it, and on food particles in the lumen (MacFarlane, S. & MacFarlane, G. T. (2006) APPL. ENVIRON. MICROBIOL. 72:6204-11; Probert, H. M. & Gibson, G. R. (2002) CURR. ISSUES INTEST. MICROBIOL. 3:23-7). The biofilms in the GI tract populated at least with pathogenic bacteria form a dense filamentous film encased within an exopolysaccharide (EPS) matrix. Such biofilms are impenetrable to antimicrobials and host immune cells, and are difficult to treat. For example, biofilms that are encased in EPS matrix have been implicated with diseases such as Crohn's Disease (CD) (Hoarau G, et al., Bacteriome and Mycobiome Interactions Underscore Microbial Dysbiosis, in Familial Crohn's Disease. Bio, 2016). Attempts to treat GI tract diseases or disorders with conventional probiotics has met with limited success.

Despite the advances made to date, there is need for improved compositions and methods for disrupting biofilms and treating biofilm associated diseases and disorders.

SUMMARY OF THE INVENTION

The present invention is based, in part, upon the discovery that it is possible to disrupt biofilms comprising, for example, pathogenic bacteria and/or pathogenic fungi, in a subject by administering to the subject a composition or a dosage form comprising both non-pathogenic bacteria and fungi, which when administered restores the natural microbiome and/or facilitates a more balanced microbiome in the subject. The present invention relates generally to compositions and methods for promoting a balanced and healthy microbial flora in a mammal.

In one aspect, the invention provides a composition comprising (i) an isolated and viable non-pathogenic fungal strain, and (ii) an isolated and viable non-pathogenic bacterial strain, which can be in the form of an admixture. The composition comprises: (i) one or more (for example, 1, 2, 3, 4, 5 or more) isolated non-pathogenic fungal strains that are viable in a preselected region of the subject, and (ii) one or more (for example, 1, 2, 3, 4, 5 or more) isolated non-pathogenic bacterial strains that are viable in the region of the subject.

In another aspect, the invention provides a composition comprising (i) an enzyme, (ii) a non-pathogenic fungal strain, and (iii) a non-pathogenic bacterial strain. For example, the composition comprises: (i) one or more (for example, 1, 2, 3, 4, 5 or more) enzymes capable, for example, of disrupting a biofilm in a preselected region of the subject, (ii) one or more (for example, 1, 2, 3, 4, 5 or more) non-pathogenic fungal strains that are viable (e.g., with or without replication) in the region of the subject, and (iii) one or more (for example, 1, 2, 3, 4, 5 or more) non-pathogenic bacterial strains that are viable (e.g., with or without replication) in the region of the subject.

In certain embodiments, the composition is formulated as a powdered blend of one or more isolated and viable non-pathogenic bacterial strains and one or more isolated and viable non-pathogenic fungal strains that is capable of disrupting biofilms or preventing formation of biofilms comprising pathogenic bacteria and/or pathogenic fungi, where the powdered blend optionally is coated, for example, coated with a functional coating such as a controlled release coating. Furthermore, in certain embodiments, the powdered blend of one or more isolated and viable non-pathogenic bacterial strains and one or more isolated and viable non-pathogenic fungal strains is freeze-dried or spray-dried. In certain embodiments, the optionally coated freeze-dried or spray-dried blend of one or more isolated and viable non-pathogenic bacterial strains and one or more isolated and viable non-pathogenic fungal strains is further blended with an enzyme (for example, amylase) capable of disrupting a biofilm.

In one aspect, the invention provides a dosage form, which upon administration to a subject, for example, a human, disrupts a biofilm or prevents formation of a biofilm comprising pathogenic bacteria and/or pathogenic fungi within a preselected region, for example, gastrointestinal tract, urinary tract, reproductive tract, upper respiratory tract, lower respiratory tract, biliary tract, mouth, eye, nose, ear, or skin, of the subject. The dosage form comprises a composition comprising: (i) one or more (for example, 1, 2, 3, 4, 5 or more) enzymes capable of disrupting the biofilm, (ii) one or more (for example, 1, 2, 3, 4, 5 or more) non-pathogenic fungal strains that are viable (e.g., with or without replication) in the region of the subject, and (iii) one or more (for example, 1, 2, 3, 4, 5 or more) non-pathogenic bacterial strains that are viable (e.g., with or without replication) in the region of the subject. The subject may be a mammal (e g, human, a companion animal (e.g., dog, cat, or rabbit), or a livestock animal (for example, cow, sheep, pig, goat, horse, donkey, and mule, buffalo, oxen, or camel)).

The microorganisms within the biofilm that are disrupted by the composition may comprise any type of pathogenic microorganism, e.g., bacteria (for example, Gram-positive bacteria and Gram-negative bacteria), fungi (for example, yeast and mold), archaea, and protozoa.

In certain embodiments, the composition or the dosage form comprises about 50, about 40, about 30, about 20 billion, about 10 billion, about 1 billion, about 500 million, about 100 million, about 50 million, or about 10 million colony forming units of the non-pathogenic bacteria strains and non-pathogenic fungal strain(s). In certain embodiments, the composition or dosage form comprises about 30 billion colony forming units of the non-pathogenic bacteria strains and non-pathogenic fungal strain(s). In certain embodiments, the composition or dosage form comprises about 15 billion colony forming units of *Bifidobacterium breve*, about 10 billion colony forming units of *Lactobacillus rhamnosus*, about 3.5 billion colony forming units of *Saccharomyces boulardii*, about 1.5 billion colony forming units of *Lactobacillus acidophilus*, and 500 SKP of Amylase. In certain embodiments, the composition comprises an admixture (blend) of one or more isolated and viable non-pathogenic bacterial strains and one or more isolated and viable non-pathogenic fungal strains is in the form of a powder. In certain embodiments, the composition comprises a powder of one or more isolated and viable non-pathogenic bacterial strains and one or more isolated and viable non-pathogenic fungal strains that is coated with functional coating (for example, coated with a controlled release coating) or a non-functional coating (for example, aesthetic coating). In certain embodiments the dosage form is a capsule, for example, a capsule that optionally is coated with a functional or non-functional coating.

In another aspect, the invention provides a method of disrupting a biofilm at a preselected region, for example, gastrointestinal tract, urinary tract, reproductive tract, upper respiratory tract, lower respiratory tract, biliary tract, mouth, eye, nose, ear, or skin, of the subject. The method comprises administering to the subject such a composition or dosage form, whereupon administration disrupts a biofilm in the subject. In certain embodiments, the biofilm comprises one or more bacteria and fungi, including (i) *Candida tropicalis* and *Escherichia coli* (*E. coli*), (ii) *Candida tropicalis* and *Serratia marcescens*, or (iii) *Candida tropicalis*, *Escherichia coli*, and *Serratia marcescens*. In certain embodiments, the biofilm comprises (i) *Candida albicans* and *Escherichia coli*, (ii) *Candida albicans* and *Serratia marcescens*, or (iii) *Candida albicans*, *Escherichia coli*, and *Serratia marcescens*.

The enzyme in the composition or dosage form disrupts extracellular matrix polysaccharides (EPSs) present in the biofilm making the pathogenic organisms more open to challenge by the non-pathogenic bacterial and fungal strains in the dosage forms. In certain embodiments, upon administration of the composition or the dosage form, the non-pathogenic bacterial strains (i) displace the pathogenic bacteria in the biofilm, (ii) interfere with the attachment of the pathogenic bacteria or fungi to a substratum of the biofilm, (iii) displace the pathogenic bacteria/fungi from an extracellular polymeric matrix present in the biofilm, (iv) prevent filamentation of the pathogenic fungi in the biofilm, or (v) a combination of any of the foregoing. In certain embodiments, administration of the composition or the dosage form permits restoration of the natural microbiome of the region in the subject and reduces the growth and/or development of pathogenic bacteria and/or pathogenic fungi.

In one aspect, the present invention provides a baked food product comprising a probiotic composition comprising (i) an isolated and viable non-pathogenic fungal strain, and (ii) an isolated and viable non-pathogenic bacterial strain. The non-pathogenic fungal and bacterial strains maintain viability after the baking process. The probiotic composition can include one or more of the compositions or dosage forms described herein.

In another aspect, the present invention provides a method of improving nutrient absorption in a subject, the method comprising consumption by the subject or administration to the subject a probiotic composition comprising (i) an isolated and viable non-pathogenic fungal strain and (ii) an isolated and viable non-pathogenic bacterial strain. The probiotic composition can include one or more of the compositions or dosage forms described herein. In certain embodiments, the probiotic composition comprises an enzyme, for example, an enzyme capable of disrupting a biofilm that may block or otherwise retard nutrient absorption.

In another aspect, the invention provides a method of identifying a subject suitable for receiving such a composition or dosage form. The method comprises: (a) quantifying the number or density of organisms of (i) at least one non-pathogenic bacterial strain and/or (ii) at least one non-pathogenic fungal strain present in a tissue or body fluid sample harvested from the region of the test subject; and (b) comparing the abundance levels or number of organisms quantified in the sample against the number or density of corresponding organisms present in a corresponding sample size of a corresponding region of a healthy subject. When the number or density of organisms in the sample from the test subject is less than the number or density of organisms present in the corresponding region of the healthy subject, the test subject is suitable for receiving the composition or dosage form.

Other features and advantages of the invention will be apparent from the following detailed description and claims.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the present disclosure. In the following description, various embodiments of the present disclosure are described with reference to the following drawings, in which:

FIG. 13A shows an untreated single species *C. albicans* biofilm. FIG. 13B shows a single species *C. albicans* biofilm treated with the probiotic filtrate. FIG. 13C shows an untreated mixed species *C. albicans, E. coli* and *S. marcescens* (CAES) biofilm. FIG. 13D shows a mixed species CAES biofilm treated with the probiotic filtrate.

FIG. 14A shows an untreated single species *C. tropicalis* biofilm. FIG. 14B shows a single species *C. tropicalis* biofilm treated with the probiotic filtrate. FIG. 14C shows an untreated mixed species *C. tropicalis, E. coli* and *S. marcescens* (CTES) biofilm. FIG. 14D shows a mixed species CTES biofilm treated with the probiotic filtrate.

DETAILED DESCRIPTION OF THE INVENTION

Figure 1A:
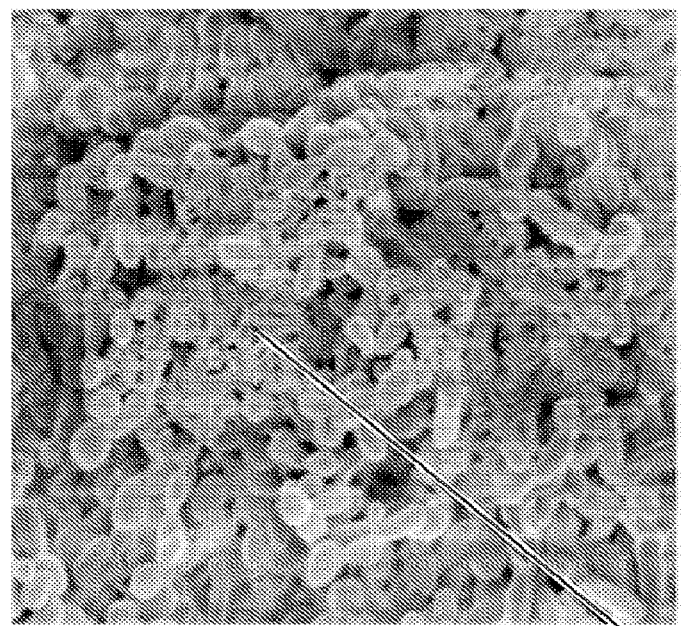
FIGS. 1A-1B are photographs showing effects of a probiotic formulation on *C. tropicalis* biofilm where FIG. 1A (1,000× magnification) and FIG. 1B (3,250× magnification) show that probiotic bacteria clump together and prevent fungal hyphenation.

The present invention is based, in part, upon the discovery that it is possible to prevent or disrupt biofilms comprising pathogenic bacteria and/or fungi, and optionally archaea and/or protozoa, in a subject by administering to the subject a composition or dosage form comprising both isolated and viable non-pathogenic bacteria and non-pathogenic fungi, which when administered promotes a more balanced microbiome and/or promotes the restoration of the natural microbiome in the subject. Unless the context dictates otherwise, the terms composition and dosage form can be used interchangeably herein, where a dosage form is a composition and vice versa. For example, it is contemplated that the composition consumed by, or administered to, a subject can be consumed or administered as a dosage form, for example, as a unit (for example, a spoonful) of the composition. Similarly, it is understood that a dosage form can, for example, comprise a composition described herein. For example, a dosage form can comprise, for example, a composition in the form of a powder described herein, or, for example, a capsule that contains such a composition.

In one aspect, the invention provides a composition comprising (i) an isolated and viable non-pathogenic fungal strain, and (ii) an isolated and viable non-pathogenic bacterial strain, which may be in the form of an admixture. The composition comprises: (i) one or more (for example, 1, 2, 3, 4, 5 or more) isolated non-pathogenic fungal strains that are viable in a preselected region of the subject, and (ii) one or more (for example, 1, 2, 3, 4, 5 or more) isolated non-pathogenic bacterial strains that are viable in the region of the subject.

In another aspect, the invention provides a composition comprising (i) an enzyme, (ii) a non-pathogenic fungal strain, and (iii) a non-pathogenic bacterial strain. For example, the composition comprises: (i) one or more (for example, 1, 2, 3, 4, 5 or more) enzymes capable of disrupting a biofilm in a preselected region of a subject, (ii) one or more (for example, 1, 2, 3, 4, 5 or more) non-pathogenic fungal strains that are viable (e.g., with or without replication) in the region of the subject, and (iii) one or more (for example, 1, 2, 3, 4, 5 or more) non-pathogenic bacterial strains that are viable (e.g., with or without replication) in the region of the subject.

In another aspect, the invention provides a composition capable of disrupting a biofilm comprising pathogenic bacteria and/or pathogenic fungi disposed within a preselected region of a subject. The composition comprises (i) one or more (for example, 1, 2, 3, 4, 5 or more) enzymes capable of disrupting the biofilm, (ii) one or more (for example, 1, 2, 3, 4, 5 or more) non-pathogenic fungal strains that are viable (e.g., with or without replication) in the region of the subject, and (iii) one or more (for example, 1, 2, 3, 4, 5 or more) non-pathogenic bacterial strains that are viable (e.g., with or without replication) in the region of the subject.

In another aspect, the invention provides a dosage form capable of disrupting a biofilm comprising pathogenic bacteria and/or pathogenic fungi disposed within a preselected region of a subject. The dosage form comprises a composition comprising (i) one or more (for example, 1, 2, 3, 4, 5 or more) enzymes capable of disrupting the biofilm, (ii) one or more (for example, 1, 2, 3, 4, 5 or more) non-pathogenic fungal strains that are viable (e.g., with or without replication) in the region of the subject, and (iii) one or more (for example, 1, 2, 3, 4, 5 or more) non-pathogenic bacterial strains that are viable (e.g., with or without replication) in the region of the subject.

I. Biofilms

The composition or dosage forms of the invention can be used to disrupt and/or replace a biofilm present at a preselected region of a subject, which can include, for example, the gastrointestinal tract, urinary tract, reproductive organs (e.g., testes, penis, urethra, ovaries, vagina, or uterus), upper respiratory tract (including the nose), lower respiratory tract (e.g., lung), biliary tract, mouth, eye, nose, ear, or skin.

Exemplary microorganisms disposed within the biofilm that may be rendered susceptible to disruption by the composition of the dosage form of the invention include, but are not limited to, species of the Firmicutes phylum, Ascomycota phylum, and Zygomycota phylum for example, *Enterococcus* spp., including *Enterococcus faecalis, Escherichia* spp., including *Escherichia coli; Chlamydia* spp., including *Chlamydia* pneumonia and *Chlamydia trachomatis, Salmonella* spp., including *Salmonella typhi* and *Salmonella typhimurium, Pseudomonas* spp., including *Pseudomonas aeruginosa* and *Pseudomonas anaerobius, Staphylococcus* spp., including *Staphylococcus aureus, Staphylococcus capitus, Staphylococcus epidermidis, Staphylococcus saprophyticus, Listeria* spp., including *Listeria monocytogenes, Helicobacter* spp., including *Helicobacter pylori, Campylobacter* spp., including *Campylobacter jejuni, Yersinia* spp., including *Yersinia pestis, Vibrio* spp., including *Vibrio cholera, Haemophilus* spp. including *Haemophilus aphrophilus* and *Haemophilus influenza, Mycobacterium* spp. including *Mycobacterium leprae, Mycobacterium tuberculosis, Burkholderia* spp., including *Burkholderia cepacia, Mycoplasma* spp., including *Mycoplasma pneumoniae, Klebsiella* spp. including *Klebsiella pneumoniae, Enterobacter* spp. including *Enterobacter cloacae, Candida* spp., including *Candida albicans, Candida dubliniensis, Candida parapsilosis, Candida tropicalis, Candida parapsilosis, Candida glabrata, Candida krusei, Candida* Auris and *Aspergillus* spp., including *Aspergillus clavatus, Aspergillus flavus, Aspergillus terreus*, and *Aspergillus fumigatus*.

Gastrointestinal Tract Biofilms

In certain embodiments, composition or dosage forms described herein can be used to disrupt a biofilm comprising, for example, pathogenic bacteria and fungi within the gastrointestinal (GI) tract (for example, esophagus, stomach, upper intestine, and/or the lower intestine) of a subject. In certain embodiments, the preselected region comprises the duodenum, the jejunum, and/or the ileum of the upper GI tract, whereas in other embodiments, the preselected region comprises the appendix, the proximal colon, and/or the rectum of the lower GI tract.

In certain embodiments, a composition or dosage form described herein is used to disrupt a biofilm disposed within the GI tract of a subject with an elevated relative abundance of pathogenic bacterial species such as *E. coli, Serratia marcescens*, and *Ruminococcus gnavus* in the biofilm disposed within the GI tract of the subject when compared to levels typically found in healthy subjects. In certain embodiments, a composition or dosage form described herein comprises non-pathogenic bacterial strains for disrupting or replacing a biofilm containing two pathogenic bacterial species. For example, the biofilm targeted for disruption or replacement may contain *E. coli* and a *Bacteroides* spp. (e.g., *Bacteroides coprophilus, Bacteroides eggerthii, Bacteroides ovatus, Bacteroides fragilis, Bacteroides plebeius*, or *Bacteroides uniformis*).

In certain embodiments, the abundance of pathogenic fungus *Candida tropicalis* in a biofilm disposed within the GI tract of a subject is elevated when compared to levels typically found in healthy subjects. In certain embodiments, biofilms within the GI tract containing *C. tropicalis* or *C. Albicans* combined with *E. coli* and/or *S. marcescens* are enriched in fungal hyphae, a form of growth associated with pathogenic conditions. Fungal filamentation can sometimes be a virulence factor used by *Candida* to damage host tissues and to trigger a specific host immune response. In certain embodiments, the dosage form of the invention is used to disrupt a biofilm disposed within the GI tract of a subject with an elevated relative abundance of bacterial species such as species of the Fimncutes phylum. In certain embodiments, the dosage form of the invention is used to disrupt a biofilm disposed within the GI tract of a subject with an elevated relative abundance of fungal species such as species of the Ascomycota phylum and species of the Zygomycota phylum and species of the Basidiomycota phylum.

The bacteria within the biofilm exist in intimate contact with the fungus but may differ in their specific interactions with the fungus. In certain embodiments, the pathogenic bacteria (e.g., *E. coli*) may be fused to the fungal cells within the biofilm. Alternatively or in addition, the pathogenic bacteria and pathogenic fungi disposed within the biofilm may form a "digestive plaque," where the bacteria and fungi are protected from antimicrobial drugs and host's immune system. It is understood that digestive plaque can disrupt the normal or healthy microbiome of the GI tract, and cause or be otherwise associated with a GI disease or disorder (e.g., hyperammonemia, *Clostridium difficile* colitis, hepatic encephalopathy associated with cirrhosis, inflammatory bowel disease, Crohn's disease, ulcerative colitis and/or irritable bowel disease).

In certain embodiments, the biofilms are formed by at least two, or three different strains of organisms, including, without limitation, *C. tropicalis, E. coli*, and *S. marcescens*. For example, the GI tract biofilm may comprise: (i) *Candida tropicalis* and *Escherichia coli*, (ii) *Candida tropicalis* and *Serratia marcescens*, or (iii) *Candida tropicalis, Escherichia coli*, and *Serratia marcescens*. In certain embodiments, *S. marcescens* cells may produce fimbriae of diameter from about 3 nm to about 18 nm and length or from about 34 nm to about 480 nm in length, which may mediate attachment with *C. tropicalis*. Under certain circumstances, strains of *S. marcescens* interact with both *C. tropicalis* and *E. coli* through such fimbriae.

In certain embodiments, the biofilm in the GI tract comprises C'. *tropicalis* or *C. albicans* that interacts with a number of different specifies including 2, 3, 4, 5, 6, 7, 8, 9, 10, 11, 12, 13 or more bacterial species, including *E. coli* and/or *S. marcescens, Alkalimonas amylolytica, Aquamonas haywardensis, Enterobacter hormaechei, Enterobacter ludwigii, Enterobacter pyrinus, Erwinia chrysanthemi, Erwinia dispersa, Erwinia soli, Erwinia toletana, Escherichia coli, Pantoea agglomerans, Profftia tarda*, and *Serratia marcescens*.

In certain embodiments, a composition or dosage form described herein can be used to disrupt a biofilm in which abundance of a fungal species, for example, *C. tropicalis* or C'. *albicans*, is increased significantly, for example, in biofilms disposed within the GI tract of subjects with Crohn's disease (CD) when compared to subjects without CD. In certain embodiments, the increase in the abundance of *C. tropicalis* or C'. *albicans* can be positively associated with ASCA (directed against terminal α-1,3-mannoside residues), a known biomarker of CD. ASCA are antibodies directed against a di- or tri-α-1-2 linked mannosides with an α-1,3 mannose at the non-reducing end. In certain embodiments, the increase in the abundance of *C. tropicalis* or *C. albicans* in the GI tract of a subject can be determined by measuring the increased detection of ASCA in a biological sample obtained from the subject. As a result, a test subject suitable for treatment with a dosage form of the invention is identified by detection of ASCA in addition to scoring the subject's Biohm Balance Score.

In certain embodiments, a composition or dosage form described herein can be used to disrupt a biofilm in which the levels of *E. coli, S. marcescens, Cronobacter sakazakii*, and *Ruminococcus gnavus* are significantly increased in the GI tract of subject, e.g. of a subject suffering from or diagnosed with having symptoms of CD.

Urinary Tract Biofilm

In certain embodiments, the composition or dosage form described herein can be used to disrupt a biofilm comprising, for example, pathogenic bacteria and pathogenic fungi disposed within the urinary tract of a subject. The biofilm may comprise pathogenic bacteria and fungi. Exemplary bacterial pathogens include, without limitation, *Escherichia coli, Klebsiella pneumoniae, Enterobacter* sp., *Pseudomonas aeruginosa, Proteus mirabilis*, etc.) and enterococci (especially *Enterococcus faecalis*), *Staphylococcus epidermidis*, and *Streptococcus agalactiae*. Fungal pathogens include, without limitation, *C. tropicalis, C. glabrata, C. albicans, C. parapsilosis, C. krusei, Candida kefyr, Candida fabianii, Candida lusitaniae, Candida dubliniensis, Candida auris*, and *Aspergillus*.

Reproductive Tract Biofilm

In certain embodiments, a composition or dosage form described herein can be used to disrupt a biofilm comprising, for example, pathogenic bacteria and pathogenic fungi disposed within the reproductive tract of a subject. The biofilm may comprise pathogenic bacteria and fungi selected from one or more of *Chlamydia trachomatis*, *Neisseria gonorrhoeae*, *Escherichia coli*, *Actinomyces israelii*, N. *Gonorrhoeae*, *Chlamydia trachomatis*, *T pallidum*, *T. vaginalis*, *Candida albicans*, *Candida glabrata*, and *C. tropicalis*.

Oral Biofilms

In certain embodiments, a composition or dosage form described herein can be used to disrupt a biofilm comprising, for example, a pathogenic bacteria and a pathogenic fungus disposed within the oral cavity. In certain embodiments, the preselected region may be the mouth. Pathogenic bacteria may include, for example, *Pseudomonas aeruginosa*, *Streptococcus mutans*, *Porphyromonas* spp., *Campylobacter* spp., *T. forsythia*, *Treponema denticola*, and *A. actinomycetemcomitans*, *Streptococcus oralis*, *Streptococcus mitis*, *Streptococcus anginosu*, *Rothia*, *Actinomyces*, *Lactobacilli* spp., *Bifidobacterium* spp., and *Fusobacterium* spp. Pathogenic fungi may include, for example, *Candida albicans*, *Candida glabrata*, and *Candida dubliniensis*.

Biofilms may be present at different locations of the oral cavity where varying environmental conditions contribute to different pathogenic bacteria and fungi being present in biofilms disposed at the different locations. For example, supragingival plaque (dental plaque) may comprise multiple types of biofilms, including biofilms formed on the surface of teeth above the gingival crevice (the highest location were the gum meets the tooth). Other locations for varied oral microbiotas include the subgingival crevice (subgingival plaque), the tongue, mucosal surfaces (buccal cells and the floor of the mouth), and dental prosthetics and fillings.

Some environmental or temporal stimuli may negatively affect the composition of a subject's microbiota by stimulating the outgrowth of pathogenic microorganisms, resulting in infection and disease. Periodontal diseases such as chronic gingivitis and periodontitis result from an increase in the complexity and volume of biofilms located in the gingival crevice. These biofilms often comprise Gram-positive facultative anaerobes, for example; *Streptococcus anginosus* and *A. naeslundii*, but in the absence of proper hygiene, the percentage of Gram-negative species, for example, *Porphyromonas* spp., *Campylobacter* spp., *T. forsythia*, *Treponema denticola*, and *A. actinomycetemcomitans*, in the biofilms increases, contributing to periodontal inflammation.

Another example of the role of pathogenic biofilms in oral disease includes dental caries, which involves cariogenic plaque (a type of biofilm), and often results in demineralization of the hard tissue of the tooth. Cariogenic plaques comprise numerous different microbial species, including *S. mutans* and other low-pH streptococci such as *Streptococcus oralis*, *Streptococcus mitis*, and, *Streptococcus* anginosu, *Rothia*, *Actinomyces*, *Lactobacilli* spp., *Bifidobacterium* spp., *Candida albicans*, and *C. glabrata*. Cariogenic plaques result when normally low populations of acidogenic and aciduric bacterial species, previously in balance with the oral environment and other plaque species, increase following high frequency carbohydrate exposure. The metabolism of carbohydrate by these microbiota results in the acidification of plaque (pH<5), and acid-induced demineralization of the enamel and dentin, and eventual cavitation.

Eye Biofilm

In certain embodiments, a composition or dosage form described herein can be used to disrupt a biofilm comprising, for example, pathogenic bacteria and pathogenic fungi disposed within the eye of a subject. The biofilm may comprise pathogenic bacteria selected from *Pseudomonas aeruginosa*, *S. marcescens*, and *Staphylococcus aureus*. The biofilm may comprise pathogenic fungi selected from *Fusarium solani*, *Fusarium oxysporum*, *Asperigullus*, and *Candida albicans* (see Szczotka-Flynn, L. B. et al. (2009) CORNEA 28:918-926).

Skin Biofilm

In certain embodiments, a composition or dosage form described herein can be used to disrupt a biofilm comprising, for example, pathogenic bacteria and pathogenic fungi associated with the skin of a subject. The biofilm may comprise pathogenic bacteria selected from *Citrobacter freundii Staphylococcus* sirnulans, *Staphylococcus*, *Enterococcus*, *Serratia*, *Pseudomonas*, *Finegoldia*, *Corynebacterium*, *Anaerococcus*, *Bacteroides*, *Serratia*, *Staphylococcus aureus*, *Finegoldia magna*, *Corynebacterium striatum*, *Anaerococcus vaginalis*, *Bacteroides vulgatus*, *Serratia rnarcescens*, *Prevotella* sp., *Peptoniphilus harei*, *Peptoniphilus ivorii*, *Pseudomonas* sp., *Pseudomonas* sp., *Anaerococcus* sp., *Streptococcus agalactiae*, *Klebsiella* sp., *Prevotella* sp., *Enterococcus* sp., *Peptoniphilus* sp., *Corynebacterium tuberculostearicum*, *Peptostreptococcus* sp., *Corynebacterium tuberculostearicum*, *Peptostreptococcus* sp., *Clostridium cellobioparum*, and *Staphylococcus capitis*. The biofilm may comprise pathogenic fungi selected from *Candida albicans*, *Candida glabrata*, *C. tropicalis*, *Candida dubliniensis*, *Candida orthopsilosis*, *Candida boleticola*, *Candida smithsonii*, *Candida xylopsoci*, *Trichosporon ovoides*, *Rhodosporidium diobovatum*, *Rhodosporidium kratochvilovae*, *Trichosporon* spp., *Wallemia* spp., *Rodotorula* spp., *Rodotorula vanillica*, *Rodotorula nothofagi*, and *Schizophyllum commune*.

Nose/Respiratory Tract Biofilm

In certain embodiments, a composition or dosage form described herein can be used to disrupt a biofilm comprising, for example, pathogenic bacteria and pathogenic fungi disposed within the nose/respiratory tract of a subject. The biofilm may comprise pathogenic bacteria selected from *Streptococcus pneumonia*, *Haemophilus influenza*, *Moraxella catarrhalis*, *P. aeruginosa*, *S. aureus*, *Escherichia coli*, and *Klebsiella* spp. The biofilm may comprise pathogenic fungi selected from *Candida* spp., *Aspergillus*, *Cryptococcus*, and *Pneumocystis* spp.

Ear Biofilm

In certain embodiments, a composition or dosage form described herein can be used to disrupt a biofilm comprising, for example, pathogenic bacteria and pathogenic fungi disposed within the ear of a subject. The biofilm may comprise pathogenic bacteria selected from *Streptococcus pneumoniae*, *Streptococcus pyogenes*, *Haemophilus influenza*, *Pseudomonas aeruginosa*, methicillin resistant *Staphylococcus aureus*, *Fusobacterium necrophorum*, *Moraxella catarrhalis*, and *Kerstersia gyiorum*. The biofilm may comprise pathogenic fungi selected from *Aspergillus flavus*, *A. fumigatus*, *A. nidulans*, *A. niger*, *C. albicans*, *C. glabrata*, *C. tropicalis*, and *C. parapsilosis*.

II. Dosage Form and Composition

The invention provides compositions or dosage forms that can prevent and/or disrupt the biofilm at preselected regions of subjects by, for example, degrading the EPS matrix and permitting non-pathogenic organisms (e.g., non-pathogenic bacteria and fungi) to replace pathogenic organisms present at that region.

In certain embodiments, the composition is formulated as a powdered blend of one or more isolated and viable non-pathogenic bacterial strains and one or more isolated and viable non-pathogenic fungal strains that is capable of disrupting a biofilm or preventing formation of biofilm comprising pathogenic bacteria and/or fungi that optionally is coated with a functional coating (e.g., controlled release coating) or a non-functional coating (e.g., aesthetic coating). In certain embodiments, the powder blend of one or more isolated and viable non-pathogenic bacterial strains and one or more isolated and viable non-pathogenic fungal strains is freeze-dried or spray-dried. In certain embodiments, the freeze-dried or spray-dried blend of one or more isolated and viable non-pathogenic bacterial strains and one or more isolated and viable non-pathogenic fungal strains is further blended with an enzyme (for example, amylase).

In certain embodiments, the composition of the present invention comprises (i) one or more enzymes capable of disrupting a biofilm in a preselected region of the subject, (ii) one or more non-pathogenic fungal strains that are viable (e.g., with or without replication) in the region of the subject, and (iii) one or more non-pathogenic bacterial strains that are viable (e.g., with or without replication) in the region of the subject. In certain embodiments, the composition comprises (i) one or more enzymes capable of disrupting the biofilm in the target region (e.g., gastrointestinal tract, urinary tract, reproductive tract, upper respiratory tract, lower respiratory tract, biliary tract, mouth, eye, nose, ear, or skin) of a subject, (ii) one or more non-pathogenic fungal strains that are viable (e.g., with or without replication) in the region of the subject, and (iii) one or more non-pathogenic bacterial strains that are viable being viable (e.g., with or without replication) in the region of the subject. The subject may be a mammal (e g, human, a companion animal (e.g., dog, cat, or rabbit), or livestock animal (for example, cow, sheep, pig, goat, horse, donkey, and mule, buffalo, oxen, or camel)).

In certain embodiments, the dosage form of the present invention comprises a composition comprising (i) one or more enzymes capable of disrupting a biofilm in a preselected region of the subject, (ii) one or more non-pathogenic fungal strains that are viable (e.g., with or without replication) in the region of the subject, and (iii) one or more non-pathogenic bacterial strains that are viable (e.g., with or without replication) in the region of the subject. In certain embodiments, the dosage form comprises a composition comprising (i) one or more enzymes capable of disrupting the biofilm in the target region (e.g., gastrointestinal tract, urinary tract, reproductive tract, upper respiratory tract, lower respiratory tract, biliary tract, mouth, eye, nose, ear, or skin) of a subject, (ii) one or more non-pathogenic fungal strains that are viable (e.g., with or without replication) in the region of the subject, and (iii) one or more non-pathogenic bacterial strains that are viable being viable (e.g., with or without replication) in the region of the subject. The subject may be a mammal (e.g., human, a companion animal (e g., dog, cat, or rabbit), or livestock animal (for example, cow, sheep, pig, goat, horse, donkey, and mule, buffalo, oxen, or camel)).

(i) Non-Pathogenic Bacteria

The composition or dosage form comprises one or more (e.g., 2, 3, 4, 5, 6, 7, 8, 9, 10, or more) different non-pathogenic bacterial strains capable of being viable or replicating in a preselected region (e.g., gastrointestinal tract, urinary tract, reproductive tract, upper respiratory tract, lower respiratory tract, biliary tract, mouth, eye, ear, or skin) of a subject.

In certain embodiments, exemplary bacterial strains to be included in the composition or dosage form of the present invention may comprise bacterial strains of any one or more of the following bacterial species: *Agrococcus jenensis, Alistipes indistinctus, Alistipes massiliensis, Alkalibacterium iburiense, Anoxybacillus kestanbolensis, Bacillus cereus, Bacillus clausii, Bacillus Coagulans, Bacteroides coprophilus, Bacteroides eggerthii, Bacteroides ovatus, Bacteroides fragilis, Bacteroides plebeius, Bacteroides uniformis, Bifidobacterium adolescentis, Bifidobacterium animalis, Bifidobacterium bifidum, Bifidobacterium breve, Bifidobacterium longum, Bifidobacterium pseudolongum, Blautia obeum, Blautia product, Candidatus azobacteroides, Candidatus portiere, Candidatus Portiera, Clostridium celatum, Clostridium hiranonis, Clostridium neonatale, Clostridium perfringens, Clostridium tyrobutyricum, Collinsella aerofaciens, Collinsella stercoris, Coprococcus eutactus, Corynebacterium stationis, Desulfosporosinus meridiei, Desulfovibrio D168, Dorea formicigenerans, Eggerthella lenta, Erwinia oleae, Faecalibacterium prausnitzii, Lactobacillus agilis, Lactobacillus reuteri, Lactobacillus ruminis, Lactobacillus salivarius, Lactobacillus zeae, Listeria weihenstephanensis, Paenibacillus mucilaginosus, Parabacteroides distasonis, Pediococcus acidilactici, Peptostreptococcus anaerobius, Prevotella copri, Prevotella melaninogenica, Prevotella stercorea, Propionibacterium acnes, Pseudoramibacter eubacterium, Roseburia faecis, Rothia dentocariosa, Rothia mucilaginosa, Ruminococcus bromii, Ruminococcus callidus, Ruminococcus flavefaciens, Ruminococcus lavefaciens, Ruminococcus gnavus, Ruminococcus torques, Salinibacillus aidingensis, Staphylococcus sciuri, Streptococcus anginosus, Streptococcus sobrinus, Tissierella soehngenia, Veillonella dispar*, and *Veillonella parvula*.

In certain embodiments, one or more of the bacterial strains listed in TABLE 1 below are included in the composition or dosage form of the present invention.

TABLE 1

| | |
|---|---|
| Bifidobacterium adolescentis | Bacillus clausii |
| Bifidobacterium animalis | Agrococcus jenensis |
| Bifidobacterium pseudolongum | Propionibacterium acnes |
| Pseudoramibacter eubacterium | Bacteroides uniformis |
| Faecalibacterium prausnitzii | Bacteroides eggerthii |
| Dorea formicigenerans | Alistipes massiliensis |
| Blautia producta | Collinsella aerofaciens |
| Bacillus cereus | Candidatus Portiera |
| Eggerthella lenta | Coprococcus eutactus |
| Ruminococcus bromii | Collinsellas tercoris |
| Bifidobacterium longum | Prevotella melaninogenica |
| Veillonella dispar | Clostridium tyrobutyricum |
| Parabacteroides distasonis | Ruminococcus gnavus |
| Ruminococcus callidus | Anoxybacillus kestanbolensis |
| Salinibacillus aidingensis | Ruminococcus flavefaciens |
| Staphylococcus sciuri | Lactobacillus rhamnosus |
| Desulfosporosinus meridiei | Bifidobacterium breve |
| Lactobacillus zeae | Lactobacillus acidophilus |
| Roseburia faecis | Bifidobacterium bifidum |
| Clostridium perfringens | Lactobacillus reuteri |
| Veillonella parvula | |

In certain embodiments, one or more of the bacterial strains listed in TABLE 2 below are included in the composition or dosage form of the present invention.

TABLE 2

| | |
|---|---|
| Bifidobacterium adolescentis | Eggerthella lenta |
| Bifidobacterium animalis | Veillonella dispar |
| Bifidobacterium pseudolongum | Lactobacillus zeae |
| Pseudoramibacter eubacterium | Lactobacillus rhamnosus |
| Faecalibacterium prausnitzii | Bifidobacterium breve |
| Dorea formicigenerans | Lactobacillus acidophilus |
| Blautia producta | Bifidobacterium bifidum |
| Bacillus cereus | Lactobacillus reuteri |

In certain embodiments, the composition or dosage form comprises one, two or three different bacterial strains (e.g., strains listed in TABLE 1 or 2) or one, two or three of *Lactobacillus rhamnosus, Bifidobacterium breve, Bifidobacterium bifidum, Lactobacillus reuteri*, and *Lactobacillus acidophilus*) capable of replicating in the region of the mammal.

In certain embodiments, the composition or dosage form comprises non-pathogenic bacterial strains for disrupting a biofilm containing one or more of *C. tropicalis, E. coli* and/or *S. marcescens* in the GI tract. For example, the GI tract biofilm may comprise: (i) *Candida tropicalis* and *Escherichia coli*, *Candida tropicalis* and *Serratia marcescens*, or (iii) *Candida tropicalis, Escherichia coli*, and *Serratia marcescens*. In certain embodiments, the biofilm in addition to or alternatively to *Candida tropicalis* may comprise: (i) *Candida albicans* and *Escherichia coli*, (ii) *Candida albicans* and *Serratia marcescens*, or (iii) *Candida albicans, Escherichia coli*, and *Serratia marcescens*.

In certain embodiments, the composition or dosage form comprises non-pathogenic bacterial strains for disrupting or replacing a biofilm containing two bacterial species. For example, the biofilm may contain *E. coli* and a *Bacteroides* spp. (e.g., *Bacteroides coprophilus, Bacteroides eggerthii, Bacteroides ovatus, Bacteroides fragilis, Bacteroides plebeius*, or *Bacteroides uniformis*).

In certain embodiments, the non-pathogenic bacterial strains included in the composition or dosage forms of the present invention may comprise a combination of any two of *Lactobacillus rhamnosus* LB 20, *Bifidobacterium breve* S 46, and *Lactobacillus acidophilus* RP 32. In certain embodiments, the non-pathogenic bacterial strains included in the composition or dosage form may comprise a combination of *Lactobacillus rhamnosus* LB 20 and *Bifidobacterium breve* S 46. In certain embodiments, the non-pathogenic bacterial strains included in the composition or dosage form may comprise a combination of *Lactobacillus rhamnosus* LB 20 and *Lactobacillus acidophilus* RP 32. In certain embodiments, the non-pathogenic bacterial strains included in the composition or dosage form may comprise a combination of *Bifidobacterium breve* S 46 and *Lactobacillus acidophilus* RP 32. In certain embodiments, the non-pathogenic bacterial strains included in the composition or dosage form of the present invention may comprise a combination of *Lactobacillus rhamnosus* LB 20, *Bifidobacterium breve* S 46, and *Lactobacillus acidophilus* RP 32.

In certain embodiments, the composition or dosage form of the invention comprises from about 10 billion to about 40 billion, e.g., from about 15 billion to about 40 billion, from about 20 billion to about 40 billion, from about 10 billion to about 30 billion, from about 15 billion to about 30 billion, from about 20 billion to about 30 billion colony forming units of the non-pathogenic bacterial strain(s).

(ii) Non-Pathogenic Fungi

The composition or dosage form also comprises one or more (e.g., 2, 3, 4, 5, 6, 7, 8, 9, 10, or more) different non-pathogenic fungal strains capable of replicating in a preselected region (e.g., gastrointestinal tract, urinary tract, reproductive tract, upper respiratory tract, lower respiratory tract, biliary tract, mouth, eye, ear, or skin) of a subject.

In certain embodiments, exemplary fungal strains to be included in the composition or dosage form of the present invention may comprise any one or more of the following fungal species: *Albatrellus syringae, Alternaria alli, Alternaria daturicola, Ambispora granatensis, Amyloathelia crassiuscula, Amylomyces rouxii*, species of Ascomycota, *Ascosphaera apis, Aspergillus flavus, Aspergillus fumigatus, Aspergillus oryzae, Aspergillus sp, Aspergillus terreus, Aspergillus versicolor, Bettsia alvei, Botryosphaeria mamane, Botryotinia fuckeliana, Candida arabinofermentans, Candida ernobii, Candida ethanolica, Candida glabrata, Candida humilis, Candida intermedia, Candida parapsilosis, Candida piceae, Candida quercitrusa, Candida tartarivorans, Candida temnochilae, Candida zemplinina, Candida zeylanoides, Chamonixia caespitosa, Cladonia polystomata, Cladosporium cladosporioides, Cladosporium halotolerans, Cladosporium sp JP67, Cladosporium sphaerospemum, Clavicorona taxophila, Clavispora lusitaniae, Craterellus sp, Dactylellina phymatopaga, Debaryomyces hansenii, Debaryomyces marasmus, Debaryomyces sp, Debaryomyces subglobosus, Dipodascus australiensis, Ectomycorrhizal, Emericella nidulans, Epulorhiza sp, Eremascus fertilis, Erernotheciurn gossypii, Eupenicilliurn cinnarnopurpureurn, Eurotiurn arnstelodami, Eurotium cristatum, Exophiala dennatitidis, Filobasidiella neoformans, Fonsecaea monophora, Fusarium solani, Fusarium dimerum, Fusarium oxysporum, Fusarium sp, Galactomyces geotrichum, Galactornyces sp, Geornyces sp, Geotrichum cucujoidarurn, Geotrichum sp, Glomus mosseae, Hanseniaspora sp, Helicobasidium longisporum, Helicostylum pulchrum, Hyphodontia flavipora, Hypochmicium cystidiatum, Inocybe sp, Kazachstania africana, Kazachstania unispora, Kluyveromyces lactis, Kluyveromyces yarrowii, Kodamaea ohmeri, Leptosphaeria biglobosa, Leptosphaerulina chartarum, Leucoagaricus sp, Lewia infectoria, Lichtheimia ramose, Macrophomina phaseolina, Monacrosporium coelobrochum, Mucor circinelloides, Mucor flavus, Mucor fuscus, Mucor sp, Myrothecium sp, Myxozyma melibiosi, Neocallimastix frontalis, Neocallimastix sp, Omphalotus nidiformis, Ophiocordyceps filifonnis, Ophiocordyceps sinensis, Penicillium carneum, Penicillium chrysogenum, Penicillium concentricum, Penicillium crustosum, Penicillium digitatum, Penicillium granulatum, Penicillium griseofulvum, Penicillium griseoroseum, Penicillium polonicum, Penicillium psychrosexualis, Penicillium pulvillorum, Penicillium roqueforti, Penicillium sclerotigenum, Penicillium sp, Penicillium spinulosum, Penicillium verrucosum, Pezizomycetes spgenotype 323, Phaeophyscia exornatula, Phialocephala lagerbergii, Phlebia radiata, Phlebia sp, Phomopsis sp, Physcia stellaris, Physoderma maydis, Pichia burtonii, Pichia jadinii, Pichia kudriavzevii, Pichia onychis, Pichia sp, Picoa juniperi, Pilaira cesatii, Pilaira sp, Pirella circinans, Preussia sp, Reddellomyces donkii, Rhizomucor pusillus, Rhizopus oryzae, Rhodosporidium kratochvilovae, Rhodosporidium sp, Rhodotorula sp, Rinodina milvina, Saccharomyces bayanus, Saccharomyces bulderi, Saccharomyces cerevisiae, Saccharomyces mikatae, Saccharomyces sp, Saccharomycetes sp, Scleroderma sp, Sclerotinia sp, Scutellospora nodose, Sebacinales sp, Sporopachydermia sp, Stenocarpella maydis, Thamnidium elegans, Torulaspora delbrueckii, Trichosporon chiarellii, Tuber oligospermum, Umbelopsis isabellina, Wallemia sebi, Wallemia sp*, and *Zygoascus meyerae*.

In certain embodiments, one or more of the fungal strains listed in TABLE 3 below may be included in the composition or dosage form of the present invention.

TABLE 3

| | |
|---|---|
| Saccharomycetes sp HZ178 | Pilaira sp Pi 3 |
| Mucor fuscus | Fungal endophyte sp M24 3281 |
| Saccharomyces bayanus | Candida temnochilae |
| Glomus mosseae | Cladosporium cladosporioides |
| Myxozyma cf melibiosi UWO | Galactomyces sp 3S 28C |
| Phaeophyscia exornatula | Exophiala dermatitidis |
| Sporopachydermia sp 91 1101 | Rhizomucor pusillus |
| Pichia kudriavzevii | Fungal sp K4 |
| Saccharomyces sp AS 23317 | Rhizopus oryzae |
| Galactomyces sp SDCF17 | Aspergillus fumigatus |
| Saccharomyces cerevisiae | Debaryomyces hansenii var hansenii |
| Aspergillus oryzae | Dipodascus australiensis |
| Candida arabinofermentans | Saccharomyces mikatae |

In certain embodiments, the composition or dosage form may comprise a non-pathogenic fungal strain selected from Saccharomyces boulardii, Saccharomyces cerevisiae, Saccharomycetes sp HZ178, Saccharomyces bayanus, strains belonging to the Pichia genus (for example, including but not limited to Pichia burtonii, Pichia jadinii, Pichia kudriavzevii, Pichia onychis, and Pichia juniper).

In certain embodiments, the composition or dosage form comprises a composition comprising a non-pathogenic fungal strain for disrupting a biofilm containing C. tropicalis. For example, the GI tract biofilm may comprise: (i) Candida tropicalis and Escherichia coli, (ii) Candida tropicalis and Serratia marcescens, or (iii) Candida tropicalis, Escherichia coli, and Serratia marcescens. In certain embodiments, the composition or dosage form comprises a composition comprising a non-pathogenic fungal strain for disrupting a biofilm containing C. albicans. In certain embodiments, the biofilm may comprise: (i) Candida albicans and Escherichia coli, (ii) Candida albicans and Serratia marcescens, or (iii) Candida albicans, Escherichia coli, and Serratia marcescens.

In certain embodiments, the composition or dosage form of the invention comprises one or more fungal strains listed in TABLE 3. In certain embodiments, the composition or dosage form of the invention comprises one or more fungal strains listed in TABLE 3 and one or more of the bacterial strains listed in TABLE 1 or TABLE 2.

In certain embodiments, the composition or dosage form comprises a composition comprising a non-pathogenic fungal strain Saccharomyces boulardii SB 48. In certain embodiments, the composition or dosage form of the invention comprises a non-pathogenic fungal strain Saccharomyces boulardii SB 48 and one or more of the bacterial strains listed in TABLE 1 or TABLE 2.

In certain embodiments, the composition or dosage form of the invention comprises from about 1 billion to about 10 billion, e.g., from about 2 billion to about 8 billion, from about 3 billion to about 6 million colony forming units of the non-pathogenic fungal strain(s).

In certain embodiments, the composition or dosage form of the invention comprises a non-pathogenic fungal strain Saccharomyces boulardii SB 48 and non-pathogenic bacterial strains of one or more of Lactobacillus rhamnosus LB 20, Bifidobacterium breve S 46, and Lactobacillus acidophilus RP 32. In certain embodiments, the composition or dosage form comprises a non-pathogenic fungal strain Saccharomyces boulardii SB 48 and non-pathogenic bacterial strains Lactobacillus rhamnosus LB 20 and Bifidobacterium breve S 46. In certain embodiments, the composition or dosage form comprises a non-pathogenic fungal strain Saccharomyces boulardii SB 48 and non-pathogenic bacterial strains Lactobacillus rhamnosus LB 20 and Lactobacillus acidophilus RP 32. In certain embodiments, the composition or dosage form comprises a non-pathogenic fungal strain Saccharomyces boulardii SB 48 and non-pathogenic bacterial strains Bifidobacterium breve S 46 and Lactobacillus acidophilus RP 32. In certain embodiments, the composition or dosage form comprises a non-pathogenic fungal strain Saccharomyces boulardii SB 48 and the non-pathogenic bacterial strains Lactobacillus rhamnosus LB 20, Bifidobacterium breve S 46, and Lactobacillus acidophilus RP 32.

In certain embodiments, the composition or dosage form of the invention comprises from about 15 billion colony forming units of Bifidobacterium breve, about 10 billion colony forming units of Lactobacillus rhamnosus, about 3.5 billion colony forming units of Saccharomyces boulardii, and about 1.5 billion colony forming units of Lactobacillus acidophilus. In certain embodiments, the composition or dosage form, once administered to a subject, releases about 30 billion live cultures of non-pathogenic bacteria and non-pathogenic fungus within a preselected region (e.g., the GI tract) of the subject.

(iii) Enzymes

In addition to non-pathogenic bacteria and fungi, the composition or dosage form further comprises an enzyme capable of disrupting the biofilm. For example, the enzyme preferably digests or otherwise disrupts/breaks down the EPS matrix of the biofilm.

The enzyme can be selected from amylase, cellulase, hemicellulase, lysozyme, pectinase, DNase I, Serratia peptidase, Serratiopeptidase, hemicellulase/pectinase complex, β-1,3-glucanase, acid protease, alkaline protease, glucoamylase, endoglucanase, xylanase, lipase, lysozyme, protease/peptidase complex, dipeptidyl peptidase IV (DPP-IV), chitosanasc, bromelain, papain, kiWi protease actinidi, a plant-derived protease, phytase, zymolase and nuclease. The enzyme may be chosen depending upon the type of biofilm and the microorganisms disposed therein. For example, an amylase enzyme may be used to degrade or otherwise disrupt carbohydrate components of the biofilm, and a nuclease such a DNase I may be used for digest or otherwise disrupt DNA in the biofilm.

In certain embodiments, the composition or dosage form comprises two or more (e.g., 2, 3, 4, 5, or more) different enzymes selected from amylase, cellulase, hemicellulase, lysozyme, pectinase, DNase I, Serratia peptidase, Serratiopeptidase, hemicellulase/pectinase complex, J3-1,3-glucanase, acid protease, alkaline protease, glucoamylase, endoglucanase, xylanase, lipase, lysozyme, protease/peptidase complex, dipeptidyl peptidase IV (DPP-IV), chitosanase, bromelain, papain, kiWi protease actinidi, a plant-derived protease, phytase, zymolase and nuclease.

In certain embodiments, a composition or dosage form described hereinabove comprises an amylase selected from Bacillus stearothermophilus amylase, Bacillus amyloliquefaciens amylase, Bacillus subtilis amylase, Bacillus licheniformi amylase, Aspergillus niger amylase, and Aspergillus oryzae amylase.

In certain embodiments, the composition or dosage form comprises an amylase, for example, from about 100 to about 5,000 SKB units of amylase, from about 200 to about 4,000 SKB units of amylase, from about 300 to about 2,000 SKB units of amylase or from about 400 to about 1,000 SKB units of amylase. An SKB or Sandstedt, Kneen, and Blish unit refers to the amount of amylase to catalyze 1 µmole substrate per minute. In certain embodiments, composition or dosage form comprises a cellulose, for example, and comprises from about 100 to about 300 CU (Cellulase unit) units per unit composition or dosage form, for example, about 200 CU. In certain embodiments, composition or dosage form comprises a hemicellulose/pectinase complex, and comprises from about 60 to about 100 HSU (Hemicellulose Specific Units) units per unit composition or dosage form, for example, about 80 HSU. In certain embodiments, the composition or dosage form comprises a β-gluconase, and comprises from about 6 to about 10 BGU (Beta Glucanase Unit), units per unit composition or dosage form, for example, about 8 BGU. In certain embodiments, the composition or dosage form comprises an acid protease, and comprises from about 15 to about 25 SAP (Shrimp Alkaline Phosphatase) units per unit composition or dosage form, for example, about 20 SAP units. In certain embodiments, the composition or dosage form comprises alkaline protease, and comprises from about 15 to about 25 HUT (hemoglobin unit Tyrosine base) units per unit composition or dosage form, for example, about 20 HUT units.

In certain embodiments, total amount of cellulase administered, for example, by the administration of one or more units of the composition or dosage form, may range from about 1 to about 10,000 CU, the total amount of hemicellulase/pectinase complex administered, for example, by the administration of one or more units of the composition or dosage form, may range from about 1 to about 8,000 HSU, the total amount of β-gluconase, for example, by the administration of one or more dosage units, may range from about 1 to about 1000 BGU, the total amount of acid protease, for example, by the administration of one or more dosage units, may range from about 1 to about 10,000 SAP, and the total amount of alkaline protease, for example, by the administration of one or more dosage units, may range from about 1 to about 40,000 HUT.

In certain embodiments, the composition or dosage form comprises about 500 SKB units of amylase, selected from α-Amylase, an endo-hydrolase that catalyzes the hydrolysis of internal α-1, 4-glycosidic linkages in starch to yield products like glucose and maltose, β-Amylase, an exo-hydrolase enzyme that hydrolyses α-1, 4-glucan linkages to yield successive maltose units, and γ-Amylase, which cleaves α-1, 6-glycosidic linkages, in addition to cleaving the last α-1, 4-glycosidic linkages to yield glucose, or a combination thereof.

(iv) Exemplary Compositions

Exemplary compositions or dosage forms of the present invention are described in Table 4. The composition of the present invention may include bacteria (*B. breve, L. acidophilus, L. rhamnosus*), fungi (*S. boulardii*), and an enzyme (e.g., amylase), and can be used as a probiotic which breaks down digestive plaque and achieves total gut balance. The probiotic composition can be delivered in powder form comprising one or more isolated and viable non-pathogenic bacterial strains and one or more isolated and viable non-pathogenic fungal strains that is optionally coated with a functional coating, which is optionally further blended with an enzyme, and contained in a capsule. In certain embodiments, 30-50 of such capsules (e.g., 42 capsules) can be consumed over a period of 2-8 weeks (e.g., 6 weeks). For example, one capsule can be consumed per day, with or without the simultaneous consumption of food. The probiotic composition preferably does not contain an allergen, artificial ingredient, or sweetener, and/or can be stored at room or ambient temperature, without refrigeration.

In certain embodiments, a composition or dosage form of the present invention comprises non-pathogenic bacteria (*B. breve, L. acidophilus, L. rhamnosus*), non-pathogenic fungi (*S. boulardii*), and an enzyme (e.g., amylase), and can be used as a pediatric/children's probiotic to break down digestive plaque and achieve total gut balance. The pediatric probiotic optionally can further comprise calcium carbonate, a sugar alcohol (e.g., xylitol), a fatty alcohol (e.g., cetyl alcohol), a weak organic acid (e.g., citric acid), natural flavor, a sweetener (e.g., monk fruit). The pediatric probiotic composition can be delivered as a powder form contained in a chewable tablet. In certain embodiments, 30-50 of such tablets (e.g., 42 tablets) can be consumed over a period of 2-8 weeks (e.g., 6 weeks). For example, one tablet can be consumed per day, with or without the simultaneous consumption of food. The pediatric probiotic composition can be naturally sweetened, for example, with monk fruit, and preferably does not contain an allergen, artificial ingredient, or sweetener, and/or can be stored at room or ambient temperature, without refrigeration.

In certain embodiments, a composition or dosage form of the present invention comprises non-pathogenic bacteria (*B. breve, L. acidophilus*, and *L. rhamnosus*), non-pathogenic fungi (e.g., *S. boulardii*), an enzyme (e.g., amylase), and vitamins (e.g., vitamin C), and can be used as a specially engineered immunity formulation to support optimal immune performance. The immunity formulation combines the power of probiotics with vitamins to provide dual-action immunity support, to break down digestive plaque and achieve total gut balance. The immunity formulation can be delivered in a powder form contained in a capsule. In certain embodiments, 30-50 of such capsules (e.g., 42 capsules) can be consumed over a period of 2-8 weeks (e.g., 6 weeks). For example, one capsule can be consumed per day, with or without simultaneous food intake. The immunity formulation preferably does not contain any artificial ingredients or sweeteners, and can be stored at room or ambient temperature, without refrigeration.

In certain embodiments, a composition or dosage form of the present invention comprises non-pathogenic bacteria (*B. breve, L. acidophilus, L. rhamnosus*), non-pathogenic fungi (*S. boulardii*), and one or more digestive enzymes (e.g., amylase, bromelain, cellulose, lipase, papain) and is used as an organic super green. The organic super green can be an engineered formulation that combines fruits, vegetables and herbal extracts with probiotics, probiotics and enzymes to break down digestive plaque and achieve total gut balance. The organic super green composition can further comprise organic plant extract (e.g., *spirulina*, barley grass, alfalfa leaf, wheat grass, chloerlla, dulse, spinach leaf, broccoli (whole plant), parsley leaf, kale leaf, *Echinacea angustifolia* root, licorice root, milk thistle seed, Siberian Eleuthero root, beet root, rose hips, acai (fruit), green tea leaf, raspberry leaf, blueberry (fruit), goji berry, bilberry (fruit), ashwagandha root, *rhodiola* root, reishi mushroom, maca root, bee pollen, nettle leaf, ginko *biloba* (4:1 leaf extract), royal jelly (3× concentrate), grape seed (2:1 extract), and fiber (e.g., sunflower lecithin, apple (fruit), brown rice bran, inulin). The organic super green formulation can be delivered in a powdered form. In certain embodiments, the product can be consumed by a subject for up to one month (e.g., 30 days), or repeated cycles of one month. In each cycle, a single serving size (e.g., 1 scoop) may be consumed per day. The organic super green formulation preferably is naturally sweetened, for example, with monk fruit, does not contain an artificial ingredient or sweetener, is allergen free, and can be stored at room or ambient temperature, without refrigeration.

TABLE 4

| Composition | Properties | Ingredients |
| --- | --- | --- |
| Exemplary Probiotic | Combines good bacteria and good fungi<br>Addresses total gut balance<br>Breaks down digestive plaque<br>Survives stomach acid<br>No refrigeration required<br>No artificial ingredients or sweeteners<br>Allergen free | Bacteria (*B. breve, L. acidophilus, L. rhamnosus*)<br>Fungi (*S. boulardii*)<br>Enzyme (Amylase) |
| Exemplary Pediatric Probiotic | Combines good bacteria and good fungi<br>Addresses total gut balance<br>Breaks down digestive plaque<br>No refrigeration required<br>Naturally sweetened<br>No artificial ingredients or sweeteners<br>Allergen Free | Bacteria (*B. breve, L. acidophilus, L. rhamnosus*)<br>Fungi (*S. boulardii*)<br>Enzyme (Amylase)<br>Additives: Calcium Carbonate, Xylitol, Cetyl Alcohol, Citric Acid, Natural Flavor, Monk Fruit |
| Exemplary Immune Stimulator | Combines Probiotic with Vitamin C for dual-action immunity support<br>Combines good bacteria and good fungi<br>Addresses total gut balance<br>Breaks down digestive plaque<br>Survives stomach acid<br>No refrigeration required<br>No artificial ingredients or sweeteners<br>Allergen free | 150 mg of Vitamin C in each capsule<br>Bacteria (*B. breve, L. acidophilus, L. rhamnosus*)<br>Fungi (*S. boulardii*)<br>Enzyme (Amylase) |
| Exemplary Organic Super Green | Organic plant extracts<br>Prebiotic Fiber<br>Combines good bacteria and good fungi<br>Addresses total gut balance<br>Breaks down digestive plaque<br>No refrigeration required<br>No artificial ingredients or sweeteners<br>Naturally sweetened<br>Allergen free | Bacteria (*B. breve, L. acidophilus, L. rhamnosus*)<br>Fungi (*S. boulardii*)<br>Digestive Enzyme Blend: (Amylase, Bromelain, Cellulase, Lipase, Papain, Protease)<br>Super Greens Blend: (Spirulina, Barley Grass, Alfalfa Leaf, Wheat Grass, Chloerlla, Dulse, Spinach Leaf, Broccoli (Whole Plant), Parsley Leaf, Kale Leaf, Echinacea angustifolia Root, Licorice Root, Milk Thistle Seed, Siberian Eleuthero Root, Beet Root, Rose Hips, Acai (Fruit), Green Tea Leaf, Raspberry Leaf, Blueberry (Fruit), Goji Berry, Bilberry (Fruit), Ashwagandha Root, Rhodiola Root, Reishi Mushroom, Maca Root, Bee Pollen, Nettle Leaf, Ginko biloba (4:1 Leaf Extract), Royal Jelly (3x Concentrate), Grape Seed (2:1 Extract)<br>Fiber Blend: (Sunflower Lecithin, Apple (Fruit), Brown Rice Bran, Inulin) |

The compositions or dosage forms of the invention described herein, can be administered or consumed individually or in combination. For example, a composition or dosage form of the present invention that includes non-pathogenic bacteria (*B. breve, L. acidophilus*, and *L. rhamnosus*), non-pathogenic fungi (*S. boulardii*), and an enzyme (e.g., amylase) may be administered or consumed individually as such, or may be co-administered or concurrently consumed with other nutrients or supplements.

(v) Manufacturing Process

Figure 20:
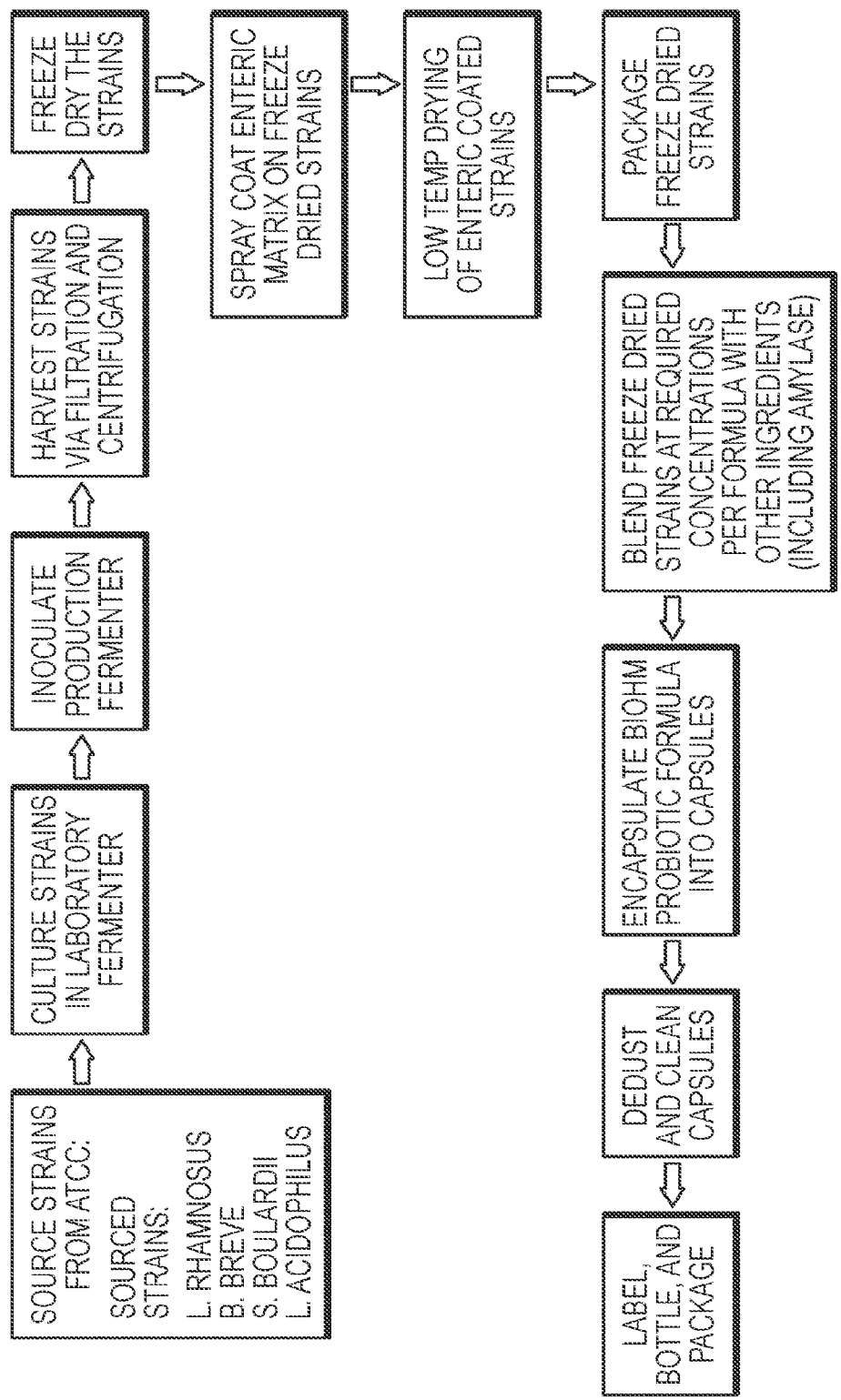
FIG. 20 is a schematic representation of an exemplary process for making a probiotic composition described herein.

In certain embodiments, a composition of the present invention may be manufactured according to the following process: The non-pathogenic fungal (e.g., *S. boulardii*) and non-pathogenic bacterial strains (e.g., *B. breve, L. acidophilus*, and *L. rhamnosus*), available at the American Type Culture Collection (ATCC), are each cultured separately in a small scale fermenter. For each strain, a culture sample is then used to inoculate a corresponding large scale production fermenter. The cultured fungal and bacterial strains are harvested via filtration and/or centrifugation, and can then be dried, for example, freeze dried. The dried organisms can then be coated, for example, spray coated with a polymer such as hydroxylpropylmethyl cellulose (HPMC). The coated strains, for example, HPMC-coated strains, can then be subjected to further drying, such as, low temperature drying (e.g., room temperature). The resulting strains are then blended together at the appropriate concentrations for the specific formulation being manufactured. At this blending stage, if desired, other ingredients specific to the formulation (e.g., dried amylase) can be added. If desired, the blended composition can then be encapsulated, which can then be packaged into an appropriately labeled container. An exemplary manufacturing process is depicted in FIG. 20

(vi) Formulation

The compositions and dosage forms described herein can be used to disrupt a biofilm present in a variety of regions within the body of a subject, for example, the GI tract, urinary tract, reproductive tract, upper respiratory tract (nose), lower respiratory tract (e.g., lung), biliary tract, mouth, eye, nose, ear, or skin. The means by which the composition or dosage form is administered to a subject may depend on the region in which the biofilm is located, and the desire for local and/or systemic administration. As such, the composition or dosage form may be formulated for use in a variety of drug delivery systems.

In certain embodiments, the composition or dosage form comprises a powder, for example, a coated powder, comprising about 10 million-about 50 billion colony forming units (CFUs) of isolated non-pathogenic fungal strain(s) and isolated non-pathogenic bacterial strain(s). In certain embodiments, the composition or dosage form of the present invention comprises about 10 million-about 40 billion, about 10 million-about 30 billion, about 10 million-about 20 billion, about 10 million-about 10 billion, about 10 million-about 5 billion, about 10 million-about 1 billion, about 10 million-about 500 million, about 10 million-about 100 million, about 10 million-about 50 million CFUs of non-pathogenic fungal strain(s) and non-pathogenic bacterial strain(s). In certain embodiments, the composition or dosage form of the present invention comprises about 20 million-50 billion, about 50 million-50 billion, about 100 million-about 50 billion, about 200 million-about 50 billion, about 500 million-about 50 billion, about 1 billion-about 50 billion, about 5 billion-about 50 billion, about 10 billion-about 50 billion, about 20 billion-about 50 billion, about 30 billion-about 50 billion, or about 40 billion-about 50 billion CFUs of non-pathogenic fungal strain(s) and non-pathogenic bacterial strain(s). In certain embodiments, the composition or dosage form may further comprise an enzyme (e.g., amylase, cellulase, hemicellulase, lysozyme, pectinase, DNase I, *Serratia* peptidase, Serratiopeptidase, hemicellulase/pectinase complex, β-1,3-glucanase, acid protease, alkaline protease, glucoamylase, endoglucanase, xylanase, lipase, lysozyme, protease/peptidase complex, dipeptidyl peptidase IV (DPP-IV), chitosanase, bromelain, papain, kiWi protease actinidi, a plant-derived protease, phytase, zymolase and nuclease).

In certain embodiments, the composition or dosage form comprises about 50 billion, about 40 billion, about 30 billion, about 20 billion, about 10 billion, about 1 billion, about 500 million, about 100 million, about 50 million, or about 10 million CFUs of non-pathogenic fungal strain(s) and non-pathogenic bacterial strain(s). In certain embodiments, one capsule comprises about 30 billion colony forming units of non-pathogenic fungal strain(s) and non-pathogenic bacterial strain(s) and an enzyme. In certain embodiments, one capsule comprises about 15 billion colony forming units of *Bifidobacterium breve*, about 1.5 billion colony forming units of *Lactobacillus acidophilus*, about 10 billion colony forming units of *Lactobacillus rhamnosus*, about 3.5 billion *Saccharomyces boulardii*, and about 500 SKB units of amylase. In certain embodiments, a low dose of 10 million CFU is effective for use as a probiotic or a composition as set forth in TABLE 4.

Oral Dosage Form

In certain embodiments, the composition or dosage form may be consumed orally by the subject. In certain embodiments, the composition is consumed as a powder or product containing the powder. In other embodiments, the composition can be in the form of an oral dosage form, for example, where the composition in included, for example, within a capsule, cachet, pill, tablet, lozenge, powder, granule, or as a solution or a suspension in an aqueous or non-aqueous liquid, or as an oil-in-water or water-in-oil liquid emulsion, or as an elixir or syrup, or as pastilles, each containing the requisite number of colony forming units of the non-pathogenic bacteria and non-pathogenic fungus, and optionally the appropriate amount of enzyme.

In certain embodiments, the composition is disposed in a capsule or in a tablet. In certain embodiments, the composition is formulated as a tablet. In certain embodiments, the capsule is a vegetable cellulose capsule. In certain embodiments, the dosage form, for example, capsule or tablet, is coated with a coating, for example, a non-functional aesthetic coating or a functional coating, for example, a controlled release coating. The capsule or tablet may be formulated so as to provide slow or controlled release of the ingredients disposed therein.

In certain embodiments, a dosage form contains a composition comprising (i) an enzyme capable of disrupting the biofilm, (ii) a non-pathogenic fungal strain capable of replicating in the region of the subject, and (iii) a non-pathogenic bacterial strain capable of replicating in the region of the subject that is formulated as a powder and encapsulated in a capsule.

In one exemplary probiotic, a capsule comprises a probiotic blend containing the ingredients set forth in TABLE 5, where, for example, powder containing the organisms can be optionally coated with a functional or a non-functional coating, and/or the capsule can be coated with a functional or a non-functional coating:

TABLE 5

Probiotic Blend (Size 1 capsule)

| Ingredient | CFU/cap | SKB/cap | mg/cap |
|---|---|---|---|
| Lactobacillus rhamnosus | 10 billion | | 90 |
| Bifidobacterium breve | 15 billion | | 75 |
| Saccharomyces boulardii | 3.5 billion | | 145 |
| Lactobacillus acidophilus | 1.5 billion | | 145 |
| Amylase | | 500 | 175 |
| Total | 30 billion | 500 | 630 |

In certain embodiment, the composition or dosage form comprises additives such as calcium carbonate, xylitol, cetyl alcohol, citric acid, natural flavor, monk fruit. In certain embodiments, the composition comprises additives such as cascara sagrada bark, *psyllium* husk, *senna* leaf, Flaxseed, aloe vera leaf, licorice root, medium chain triglyceride (MCT) oil. In certain embodiments, the composition or dosage form comprises additives such as a dietary fiber, e.g., inulin (fructooligosaccharides FOS) and apple pectin. In certain embodiments, the composition or dosage form comprises additives such as a blend of *spirulina*, barley grass, alfalfa leaf, wheat grass, chloerlla, dulse, spinach leaf, broccoli, parsley leaf, kale leaf, *echinacea angustifolia* root, licorice root, milk thistle seed, Siberian eleuthero root, beet root, rose hips, acai (fruit), green tea leaf, raspberry leaf, blueberry (fruit), goji berry, bilberry (fruit), ashwagandha root, *rhodiola* root, reishi mushroom, maca root, bee pollen, nettle leaf, ginko *biloba* (leaf extract), royal jelly (3× concentrate), grape seed. In certain embodiments, the composition further comprises a vitamin, such as, vitamin C.

Coatings

Depending upon the mode of delivery or the region to be treated, the composition or dosage form of the present invention may be prepared as a powdered blend of organisms where the powder can be coated with a non-functional coating (e.g., aesthetic coating) or a functional coating (e.g., controlled release coating to modulate the release of the organisms in, for example, a time- and/or pH-dependent manner). Similarly, the composition or dosage form may be a capsule containing a powdered blend of organisms, where the capsule is coated with a non-functional (e.g., aesthetic coating) or a functional coating (e.g., a controlled release coating to modulate the release of the organisms in, for example, a time- and/or pH-dependent manner). In certain embodiments, controlled release coating is hydroxypropyl methylcellulose (HPMC).

Controlled release coatings can facilitate the continuous release, gradual release, prolonged release, and/or programmed release (e.g., pH-dependent release) of the microorganisms in the compositions or dosage forms disclosed herein.

Exemplary controlled release coatings can be selected from the group consisting of acetate succinate, a polyvinyl derivative (for example, polyvinyl alcohol, polyvinyl acetate, polyvinyl acetate phthalate, a copolymer of vinyl acetate and vinyl pyrrolidone, a copolymer of vinyl acetate and crotonic acid, polyvinylpyrrollidone), polyethylene oxide, polyacrylic acid, polysaccharides (for example, modified starch, cross-linked high amylose starch, hydroxypropyl starch, cellulose and cellulose derivatives (for example, microcrystalline cellulose, carboxymethylethyl cellulose, cellulose acetate, methylcellulose, methylhydroxyethylcellulose, ethylcellulose, hydroxypropyl cellulose, hydroxyethylcellulose, hydroxypropylmethyl cellulose, cellulose phthalate, cellulose acetate, cellulose acetate phthalate, cellulose acetate propionate, cellulose-acetate succinate, cellulose acetate butyrate, cellulose-acetate trimellitate, ethylhydroxyethylcellulose, carboxymethylcellulose or methylcarboxymethylcellulose), poloxamer, povidone, alginic acid, sodium alginate, polyethylene glycol, polyethylene glycol alginate, gums (for example, xanthan gum), polymethacrylates (including, for example, a copolymer of methacrylic acid and methyl-methacrylate, and a copolymer of methacrylic acid and ethyl acrylate), a copolymer of methacrylic acid and ethyl acrylate, a copolymer of polymethyl vinyl ether and malonic acid anhydride, a copolymer of polymethyl vinyl ether and malonic acid or the ethyl-, isopropyl-, n-butylesters thereof, zein, and mixtures of the foregoing.

Further examples of controlled release film-coating polymers include, but are not limited to, ethylcellulose (for example, AQUACOAT®, SURELEASE®, methylhydroxypropylcellulose (for example, PHARMACOAT®, acrylic polymers, polyvinylacetates, polyvinyl chlorides, hydroxypropylmethylcellulose acetate succinate (for example, AQOAT), and polyvinyl acetate phthalate (for example, SURETERIC).

In certain embodiments, the coating can be an enteric coating. Enteric coatings can be used to create a barrier that controls the region along the GI tract where the active ingredient(s) are released and absorbed. Enteric coatings may include, for example, a polymer that disintegrates at different rates according to pH. Enteric coatings may include, for example, cellulose acetate phthalate, cellulose acetate trimellitate, methyl acrylate-methacrylic acid copolymers, cellulose acetate succinate, hydroxymethylcellulose, hydroxylpropylmethyl cellulose phthalate, methyl methacrylate-methacrylic acid copolymers, ethylacrylate-methacrylic acid copolymers, methacrylic acid copolymer type C, polyvinyl acetate-phthalate, cellulose acetate phthalate, polyvinyl acetate phthalate, carboxymethylethylcellulose, co-polymerized methacrylic acid/methacrylic acid methyl esters such as, for instance, materials known under the trade name EUDRAGIT® L12.5, L100, or EUDRAGIT® S12.5, S100 or similar compounds used to obtain enteric coatings. Aqueous colloidal polymer dispersions or re-dispersions can be also applied, e.g. EUDRAGIT® L 30D-55, EUDRAGIT® L100-55. EUDRAGIT® S100, EUDRAGIT® preparation 4110D (Rohm Pharma); AQUATERIC®, AQUACOAT® CPD 30 (FMC): KOLLICOAT MAE® 30D and 30DP (BASF): EASTACRYL® 30D (Eastman Chemical).

In certain embodiments, the enteric coating comprises an anionic, cationic, or neutral copolymer based on methacrylic acid, methacrylic/acrylic esters or their derivatives. Cationic polymers often are used for taste-masking and for achieving high bioavailability of active ingredients by their low solubility in oral cavity (pH 5.8-7.4) and high solubility in the stomach (pH 1-3.5), respectively. Anionic polymers have higher water solubility at basic pH than at acidic pH and are used for protecting active ingredients from acid degradation in the stomach and/or enzyme digestion in the intestine.

In certain embodiments, the enteric coating comprises an ethylacrylate-methacrylic acid copolymer. Commercially available enteric coatings include Opadry® AMB, ethylacrylate-methacrylic acid copolymers (e.g., ACRYL-EZE®), dimethylaminoethyl methacrylate-butyl methacrylate-methyl methacrylate copolymer (2:1:1), or poly (methacrylic acid-co-methyl-methacrylate) copolymers, and poly(methacrylic acid-co-methyl-methacrylate) copolymers (e.g., EUDRAGIT®). In certain embodiments, the enteric coating may comprise from about 0.1% to about 10%, from about 1% to about 10%, from about 5% to about 10%, from about 5% to about 20%, from about 8% to about 15%, from about 8% to about 18%, from about 10% to about 12%, or from about 12% to about 16%, of the dosage form (e.g., capsule, tablet or pellet) by weight.

In certain embodiments, the composition or dosage form of the present invention prepared as a powdered mix of one or more isolated and viable non-pathogenic bacterial strains and one or more isolated and viable non-pathogenic fungal strains, which may be enteric-coated, or as a capsule containing a powdered mix, where the capsule is enteric-coated, for delivery to the upper intestine. In certain embodiments, the bacterial and fungal strains of the present invention are mixed in a blend to prepare a powder composition, which is then enteric-coated with an cationic copolymer. For example, the powdered mix of the non-pathogenic bacterial and the non-pathogenic fungal strains of the present invention may be coated with a cationic polymer comprising dimethylaminoethyl methacrylate, butyl methacrylate, and methyl methacrylate at a ratio of 2:1:1 (EUDRAGIT® E 100); a cationic copolymer based on dimethylaminoethyl methacrylate, butyl methacrylate, and methyl methacrylate at a ratio of 2:1:1 (EUDRAGIT® EPO); a cationic copolymer based on dimethylaminoethyl methacrylate, butyl methacrylate, and methyl methacrylate at a ratio of 2:1:1 (EUDRAGIT® E 12, 5), an anionic copolymer based on methacrylic acid and ethyl acrylate (EUDRAGIT® L 100-55 (ACRYL-EZE®)), or an equivalent thereof.

In certain embodiments, the bacterial and fungal strains of the present invention are mixed in a blend to prepare a powder composition, which is then enteric-coated with an anionic copolymer. For example, the powder blend of the bacterial and fungal strains of the present invention may be coated with an anionic copolymer comprising methacrylic acid and methyl methacrylate (e.g., EUDRAGIT® L 100, EUDRAGIT® S 100, EUDRAGIT® L/S (25/75, 50/50, or 75/25 ratio)), or an anionic copolymer comprising methacrylic acid and ethyl acrylate (EUDRAGIT® L 100-55

(ACRYL-EZE®)). Additional but non-limiting examples of the coatings for delivery in the colon include, EUDRAGIT® L 100-55, EUDRAGIT® L 30 D-55, PlasACRYL® HTP 20, EUDRAGIT® L 12,5, EUDRAGIT® FS 100, EUDRAGIT® FS 30 D, and PlasACRYL® T20.

In certain embodiments, the bacterial and fungal strains of the present invention are mixed in a blend to prepare granulates or pellets, which are enteric-coated.

In certain embodiments, the powder blend of the bacterial and fungal strains of the present invention may be enteric-coated for time-controlled delivery throughout the entire GI-tract to increase therapeutic effect. For example, the composition or dosage form may be coated with EUDRAGIT® RL 100, EUDRAGIT® RL PO, EUDRAGIT® RL 30 D, EUDRAGIT® RL 12,5, EUDRAGIT® RS 100, EUDRAGIT® RS PO, EUDRAGIT® RS 30 D, EUDRAGIT® RS 12,5, EUDRAGIT® NE 30 D, EUDRAGIT® NE 40 D, and/or EUDRAGIT® NM 30 D.

An exemplary method of producing an oral dosage form comprises selecting the appropriate non-pathogenic bacterial and fungal strains to be combined in the dosage form, growing the organisms in a fermenter, either individually or combination depending upon the growth conditions. Once the appropriate amount of biomass has been created, the cells can be harvested via filtration and/or centrifugation. If one or more of the organisms is grown individually, the organisms then can be combined in the appropriate amounts to give the appropriate composition or dosage form, which can then be dried, for example, via freeze drying or spray drying. Alternatively, the organisms, once harvested, can be dried, for example, via freeze drying or spray drying, and then the appropriate dried biomass of each organism can be combined in the appropriate amounts to give the appropriate composition or dosage form. In certain embodiments the dried biomass is prepared in a powder form, and is coated with a functional coating, for example, a controlled release coating (e.g., hydroxypropylmethyl cellulose). The enzyme can be added to the biomass during one or more of each of the foregoing steps, for example, before or after the biomass has been dried. In certain embodiments, the enzyme can be added to the biomass prepared as a powder, for example, before or after coating the powdered biomass when a coating is desired. The resulting biomass (e.g., coated powder) can then be packaged into capsules and packaged into a container.

Topical Dosage Form

In certain embodiments, the composition or dosage form may be formulated for topical delivery, for example, as a liquid, emulsion, suspension, ointment, cream, gel, lotion, or powder. In certain embodiments, upon application to a skin of a subject, the composition or dosage form may form a patch. Depending up the concentration of non-pathogenic organisms and the particular delivery device, the composition or dosage form may be formulated to deliver from about 1.0 mL/5 cm$^2$ to 1.0 mL/50 cm$^2$, or from about 1.0 mL/5 cm$^2$ to 50 mL/50 cm$^2$, or from about 1.0 mL/5 cm$^2$ to about 100 mL/50 cm$^2$.

The topical dosage form may also include a pharmaceutically acceptable carrier. Suitable carriers that may be useful in topical formulations include, but are not limited to, solubilizers such as $C_2$-$C_8$, straight and branched chain alcohols, diols and triols, moisturizers and humectants such as glycerin, amino acids and amino acid derivatives, polyaminoacids and derivatives, pyrrolidone carboxylic acids and its salts and derivatives, surfactants such as sodium lauryl sulfate, sorbitan monolaurate, emulsifiers such as cetyl alcohol, stearyl alcohol, thickeners such as methyl cellulose, ethyl cellulose, hydroxymethylcellulose, hydroxypropylcellulose, polyvinylpyrollidone, polyvinyl alcohol and acrylic polymers.

The composition or dosage form may be applied to the skin by any means known in the art including, for example, by an aerosol, spray, pump-pack, brush, swab, or other applicator. In certain embodiments, the applicator may provide either a fixed or variable metered dose such as a metered dose aerosol, or a manual metered dose pump. In certain embodiments, the active ingredients may be delivered by a unit volume dispenser with or without a roll-on or other type of applicator. In certain embodiments, the active ingredients are applied to the skin of the subject covering a delivery surface area from about 10 to about 800 cm$^2$, from about 10 to about 400 cm$^2$, or from about 10 to about 200 cm$^2$.

Ointments are semisolid preparations that typically are based on petrolatum or other petroleum derivatives. As with other carriers or vehicles, an ointment base should be inert, stable, non-irritating and non-sensitizing.

Creams are viscous liquids or semisolid emulsions, either oil-in-water or water-in-oil. Typically, cream bases are water-washable, and contain an oil phase, an emulsifier, and an aqueous phase. The oil phase, also called the "internal" phase, generally comprises petrolatum and a fatty alcohol such as cetyl or stearyl alcohol. The aqueous phase usually, although not necessarily, exceeds the oil phase in volume, and generally contains a humectant. The emulsifier in a cream formulation is generally a nonionic, anionic, cationic, or amphoteric surfactant.

Gels are semisolid, suspension-type systems. Single-phase gels contain organic macromolecules distributed substantially uniformly throughout the carrier liquid, which is typically aqueous, but also contains an alcohol and, optionally, an oil. In certain embodiments, gelling agents comprise crosslinked acrylic acid polymers such as carbomers, for example, carboxypolyalkylenes that may be obtained commercially (CARBOPOL™). Hydrophilic polymers such as polyethylene oxides, polyoxyethylene-polyoxypropylene copolymers, and polyvinylalcohol; cellulosic polymers such as hydroxypropyl cellulose, hydroxyethyl cellulose, hydroxypropyl methylcellulose, hydroxypropyl methylcellulose phthalate, and methyl cellulose; gums such as tragacanth and xanthan gum; sodium alginate; and gelatin may also be included. In order to prepare a uniform gel, dispersing agents such as alcohol or glycerin may be added, or the gelling agent can be dispersed by trituration, mechanical mixing, or stirring, or combinations thereof.

Various additives, known to those skilled in the art, may be included in the topical dosage forms. For example, solvents, including relatively small amounts of alcohol (e.g., equal to or less than 10%) may be used to solubilize certain components. In certain embodiments, the formulation may include a suitable enhancer, for example, ethers such as diethylene glycol monoethyl ether (available commercially as TRANSCUTOL™) and diethylene glycol monomethyl ether; surfactants such as sodium laurate, sodium lauryl sulfate, cetyltrimethylammonium bromide, benzalkonium chloride, Poloxamer (231, 182, 184), TWEEN® (20, 40, 60, 80), and lecithin; alcohols such as ethanol, propanol, octanol, benzyl alcohol, and the like; polyethylene glycol and esters thereof such as polyethylene glycol monolaurate (PEGML); amides and other nitrogenous compounds such as urea, dimethylacetamide (DMA), dimethylformamide (DMF), 2-pyrrolidone, 1-methyl-2-pyrrolidone, ethanolamine, diethanolamine, and triethanolamine; terpenes; alkanones; and organic acids such as citric acid and succinic acid.

Spray and Inhalation Dosage Forms

In certain embodiments, the composition or dosage form may be formulated for nasal administration in the form of a nasal spray and inhalation solution, and suspension, that is administered for example, by inhalation through the nose. The dose can be delivered to the nasal cavity via a spray pump or as nasal drops for local and/or systemic effects.

In certain embodiments, the composition or dosage form may be an inhalation solution and/or suspension for delivery to the upper and lower respiratory tract (e.g. oropharynx, lungs) by oral inhalation for local and/or systemic effects and can be used with a specified nebulizer.

(III) Dose

The size of the dose delivered or consumed, will depend upon, among other things, the size and age of the subject, the indication or condition to be treated, and the mode of delivery of the composition or dosage form. In certain embodiments, for example, oral composition or dosage forms may comprise from about 1 mg to about 1,000 mg or 50 mg to about 1,000 mg of the active ingredients (for example, the non-pathogenic bacteria, the non-pathogenic fungus, and/or the enzyme). In certain embodiments, the composition or dosage form may comprise from about 1 mg to about 900 mg, about 1 mg to about 800 mg, about 1 mg to about 700 mg, about 1 mg to about 600 mg, about 1 mg to about 500 mg, about 1 mg to about 400 mg, about 1 mg to about 300 mg, about 1 mg to about 200 mg, about 1 mg to about 100 mg, about 1 mg to about 500 mg, about 10 mg to about 1000 mg, about 20 mg to about 1000 mg, about 30 mg to about 1000 mg, about 40 mg to about 1000 mg, about 50 mg to about 1000 mg, about 100 mg to about 1000 mg, about 200 mg to about 1000 mg, about 300 mg to about 1000 mg, about 400 mg to about 1000 mg, about 500 mg to about 1000 mg, about 600 mg to about 1000 mg, about 700 mg to about 1000 mg, about 800 mg to about 1000 mg, or about 900 mg to about 1000 mg of the active ingredients (for example, the non-pathogenic bacteria, the non-pathogenic fungus, and/or the enzyme).

In certain embodiments, the composition or dosage form may comprise from about 100 mg to about 200 mg, from about 200 mg to about 300 mg, from about 300 mg to about 400 mg, from about 400 mg to about 500 mg, from about 500 mg to about 600 mg, from about 600 mg to about 700 mg, from about 700 mg to about 800 mg, from about 800 to about 900 mg, or from about 900 to about 1000 mg of the active ingredients. In certain embodiments, the composition or dosage form may comprise about 700 mg of the active ingredients.

In certain embodiments, the composition or dosage form comprises about 50, 40, 30, or 20 billion colony forming units of the non-pathogenic bacteria strains and non-pathogenic fungal strain(s). In certain embodiments, the composition or dosage form comprises about 30 billion colony forming units of the non-pathogenic bacteria strains and non-pathogenic fungal strain(s).

In certain embodiments, the composition or dosage form of the invention comprises from about 10 billion to about 40 billion, e.g., from about 15 billion to about 40 billion, from about 20 billion to about 40 billion, from about 10 billion to about 30 billion, from about 15 billion to about 30 billion, from about 20 billion to about 30 billion colony forming units of the non-pathogenic bacterial strain(s). Alternatively, or in addition, the composition or dosage form of the invention comprises from about 1 billion to about 10 billion, e.g., from about 2 billion to about 8 billion, from about 3 billion to about 6 million colony forming units of the non-pathogenic fungal strain(s).

In certain embodiments, the composition or dosage form comprises about 15 billion colony forming units of *Bifidobacterium breve*, about 10 billion colony forming units of *Lactobacillus rhamnosus*, about 3.5 billion colony forming units of *Saccharomyces boulardii*, and about 1.5 billion colony forming units of *Lactobacillus acidophilus*.

The composition or dosage forms (either one or multiple units (for example 2, 3, 4, or 5 units, for example, capsules or tablets) may be administered once, twice or three times a day during the treatment period, for example, until the biofilm of interest has been disrupted, prevented from forming, and/or the subject's normal microbiome has been restored which could take, for example, one week, two weeks, one month, two months, or three months and one year. In certain embodiments, one capsule, such as one enteric-coated capsule, that comprises about 30 billion colony forming units of non-pathogenic fungal strain(s) and non-pathogenic bacterial strain(s) and an enzyme, is administered once, twice, or three times a day during the treatment period, for example, until the biofilm of interest has been disrupted and/or the subject's normal microbiome has been restored which could take, for example, one week, two weeks, one month, two months, or three months and one year. In certain embodiments, one capsule, such as one enteric-coated capsule, that comprises about 30 billion colony forming units of non-pathogenic fungal strain(s) and non-pathogenic bacterial strain(s) and an enzyme is administered once per day. In certain embodiments, the capsule, such as the enteric-coated capsule, administered once per day comprises about 15 billion colony forming units of *Bifidobacterium breve*, about 1.5 billion colony forming units of *Lactobacillus acidophilus*, about 10 billion colony forming units of *Lactobacillus rhamnosus*, about 3.5 billion *Saccharomyces boulardii*, and about 500 SKB units of amylase.

(IV) Cooked Food Products

In addition, the invention provides cooked, for example, baked, food products that contain any of the probiotic compositions of the invention described herein. Exemplary baked food products may include but are not limited to: breads, buns, bagels, cakes, cookies, crackers, pancakes, muffins, biscuits, pies, brownies, casseroles, puddings, or tarts.

In certain embodiments, the baked food product comprises a probiotic composition comprising (i) one or more (for example, 1, 2, 3, 4, 5 or more) non-pathogenic fungal strains, (ii) one or more (for example, 1, 2, 3, 4, 5 or more) non-pathogenic bacterial strains, and (iii) an optional enzyme. In certain embodiments, the baked food product comprises a probiotic composition comprising (i) one or more (for example, 1, 2, 3, 4, 5 or more) non-pathogenic fungal strains, (ii) one or more (for example, 1, 2, 3, 4, 5 or more) non-pathogenic bacterial strains, and (iii) an enzyme.

In certain embodiments, the non-pathogenic bacteria included in the probiotic composition contained in the baked food products may include *Lactobacillus rhamnosus*, *Lactobacillus acidophilus*, and *Bifidobacterium breve*, and the non-pathogenic fungi may include *Saccharomyces boulardii* and *Saccharomyces cerevisiae*.

In certain embodiments, the enzyme included in the probiotic composition contained in the baked food products may include amylase, cellulase, hemicellulase, lysozyme, pectinase, DNase I, *Serratia* peptidase or Serratiopeptidase, hemicellulase/pectinase complex, β-1,3-glucanase, acid protease, alkaline protease, glucoamylase, endoglucanase, xylanase, lipase, lysozyme, protease/peptidase complex, dipeptidyl peptidase IV (DPP-IV), chitosanase, bromelain, papain, kiWi protease actinidi, a plant-derived protease, and phytase.

In a specific embodiment, the baked food product contains a probiotic composition comprising *Lactobacillus rhamnosus* LB 20, *Bifidobacterium breve* S 46, *Lactobacillus acidophilus* RP 32, and *Saccharomyces boulardii* SB 48. In a specific embodiment, the baked food product contains a probiotic composition comprising *Lactobacillus rhamnosus* LB 20, *Bifidobacterium breve* S 46, *Lactobacillus acidophilus* RP 32, *Saccharomyces boulardii* SB 48, and amylase.

It surprisingly has been discovered that the baking process for producing a baked product does not materially comprise the viability or efficacy of the probiotic composition contained therein. For example, the microbial strains (non-pathogenic fungal and non-pathogenic bacterial strains) and/or an enzyme included in the probiotic composition contained in the baked food product survive baking temperatures up to 450° F. (e.g., 200, 250, 300, 350, 400, or 450° F.) for up to 90 minutes (e.g., 20, 30, 40, 50, 60, 70, 80, or 90 minutes). As a result, the completed baked food products contain probiotic compositions with viable microbial strains (non-pathogenic fungal and bacterial strains) and optionally an enzyme.

(V) Methods of Disrupting a Biofilm and Treatment

The invention provides a method of disrupting a biofilm or preventing formation of a biofilm that comprises both pathogenic bacteria and pathogenic fungi disposed within a preselected region of a subject in need of treatment. The method comprises administering to the subject one or multiple units (for example, capsules or tablets) of compositions or dosage forms described herein, thereby to disrupt the biofilm. In certain embodiments, the biofilm is disposed in the gastrointestinal tract, urinary tract, reproductive tract, upper respiratory tract (for example, nose), lower respiratory tract (for example, lung), biliary tract, mouth, eye, nose, ear, or skin. The subject may be a mammal (e.g., human, a companion animal (e.g., dog, cat, or rabbit), or livestock animal (for example, cow, sheep, pig, goat, horse, donkey, and mule, buffalo, oxen, or camel)).

Depending upon the circumstances, the non-pathogenic bacterial strains in the composition or dosage form can (i) displace the pathogenic bacteria in the biofilm, (ii) interfere with the attachment of the pathogenic bacteria/fungus to a substratum of the biofilm, (iii) displace the pathogenic bacteria/fungus from an extracellular polymeric matrix present in the biofilm, (iv) prevent filamentation of the pathogenic fungus in the biofilm, (v) a combination of any of the foregoing, (vi) inhibit the virulence factors of the pathogenic bacteria and fungi (e.g. germination, adherence, etc.).

Under certain circumstances, administration of the composition or dosage form to the subject maintains the total balance of the subject's gut microbiome (including the subject's mycobiome and/or bacteriome), without causing harmful digestive plaque, thereby supporting the subject's optimal digestive health.

In certain embodiments, administration of the composition or dosage form to the subject treats a misbalance in the microbiome of the subject (for example, permits restoration of natural microbiome in a region of the subject) or treats a disorder such as hyperammonemia, *Clostridium difficile* colitis, hepatic encephalopathy associated with cirrhosis, inflammatory bowel disease, Crohn's disease, ulcerative colitis, diarrhea and/or irritable bowel disease. In certain embodiments, administration of the composition or dosage form to the subject treats digestive disorder or symptoms, for example, heartburn/GERD, IBD, and IBS, bloating, diarrhea, gas, stomach pain, and/or stomach cramps.

As used herein, the terms "treat," "treating," or "treatment," and other grammatical equivalents as used herein, include alleviating, abating, ameliorating, or preventing a disease, condition or symptoms, preventing additional symptoms, ameliorating or preventing the underlying causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition, and are intended to include prophylaxis.

As used herein, the terms, "subject," "patient," "subject in need thereof," and "patient in need thereof" are used interchangeably herein, and refer to a living organism, including animals and humans, suffering from or prone to a disease or condition that can be treated by the methods and compositions provided herein. The subject can be a human or non-human animal.

(VI) Improvement of Nutrient Absorption in a Subject

In addition, the invention provides methods and compositions for improving nutrient absorption in a subject. Pathogenic organisms such as *Candida tropicalis, Candida albicans, Escherichia coli*, and *Serratia marcescens* may work together to form a robust biofilm on the gastrointestinal lining of a subject. By forming a layer over the gut lining, these biofilms scavenge nutrients (e.g., sugars) to fuel their own growth and may impede nutrient absorption across the gastrointestinal lining, and subsequently, may reduce nutrient availability. Accordingly, the invention provides methods and compositions for improving nutrient absorption in a subject, by consumption or administration of a probiotic composition that leads to disruption or elimination of biofilms on the gastrointestinal lining of the subject.

In some embodiments, the improvement in nutrient absorption in a subject includes improving absorption of nutrients such as, but not limited to, vitamins (e.g., vitamins A, B, C, D, E, K), proteins, amino acids including but not limited to, histidine, isoleucine, leucine, lysine, methionine, phenylalanine, threonine, tryptophan, and valine; collagen, minerals included but not limited to, calcium, potassium, iron, sodium, magnesium, zinc, phosphorus, chloride; and carbohydrate included but not limited to, sugars.

In certain embodiments, the improvement in nutrient absorption in a subject comprises consumption by, or administering to, the subject a probiotic composition comprising (i) one or more (for example, 1, 2, 3, 4, 5 or more) non-pathogenic fungal strains and (ii) one or more (for example, 1, 2, 3, 4, 5 or more) non-pathogenic bacterial strains. In certain embodiments, the method comprises consumption by, or administering to, the subject a probiotic composition comprising (i) one or more (for example, 1, 2, 3, 4, 5 or more) non-pathogenic fungal strains, (ii) one or more (for example, 1, 2, 3, 4, 5 or more) non-pathogenic bacterial strains, and (iii) an enzyme.

In certain embodiments, the non-pathogenic bacteria included in the probiotic composition may include *Lactobacillus rhamnosus, Lactobacillus acidophilus*, and *Bifidobacterium breve*, and the non-pathogenic fungi may include *Saccharormyces boulardii* and *Saccharomyces cerevisiae*.

In certain embodiments, the enzyme included in the probiotic composition may include one or more of: amylase, cellulase, hemicellulase, lysozyme, pectinase, DNase I, *Serratia* peptidase or Serratiopeptidase, hemicellulase/pectinase complex, β-1,3-glucanase, acid protease, alkaline protease, glucoamylase, endoglucanase, xylanase, lipase, lysozyme, protease/peptidase complex, dipeptidyl peptidase IV (DPP-IV), chitosanase, bromelain, papain, kiWi protease actinidi, a plant-derived protease, and phytase.

In a specific embodiment, the improvement in nutrient absorption in a subject comprises consumption by, or administering to, the subject a probiotic composition comprising *Lactobacillus rhamnosus* LB 20, *Bifidobacterium breve* S 46, *Lactobacillus acidophilus* RP 32, and *Saccharomyces boulardii* SB 48. In a specific embodiment, the improvement in nutrient absorption in a subject comprises consumption by, or administering to, the subject a probiotic composition comprising *Lactobacillus rhamnosus* LB 20, *Bifidobacterium breve* S 46, *Lactobacillus acidophilus* RP 32, *Saccharomyces boulardii* SB 48, and amylase.

In some embodiments, the subject consumes or is administered the probiotic composition for 2-8 weeks (e.g., 6 weeks), wherein the probiotic composition is delivered as an enteric-coated powder comprising one or more isolated and viable non-pathogenic bacterial strains and one or more isolated and viable non-pathogenic fungal strains contained in a capsule. In some embodiments, the subject consumes or is administered the probiotic composition for up to 7 days or repeated cycles of 7 days. In some embodiments, the subject consumes or is administered the probiotic composition for up to one month or repeated cycles of one month.

(VII) Method of Testing Suitability of a Subject for Treatment

The invention also provides a method of identifying a test subject suitable for treatment with a composition or dosage form described herein. The method comprises: (a) quantifying the number or density and/or abundance of organisms of (i) at least one non-pathogenic bacterial strain and (ii) at least one non-pathogenic fungal strain present in a tissue or body fluid sample harvested from the region of the test subject; and (b) comparing the number or density of organisms quantified in the sample against the number or density of corresponding organisms present in a corresponding sample size of a corresponding region of a healthy subject. When the number or level of organisms in the sample from the test subject is less than the number or level of organisms present in the corresponding region of the healthy subject, the test subject is suitable for treatment with the dosage form.

In certain embodiments, the non-pathogenic bacteria that are quantified may include *Lactobacillus rhamnosus, Lactobacillus acidophilus*, and *Bifidobacterium breve* and/or the non-pathogenic fungi that are quantified may include *Saccharomyces boulardii* and *Saccharomyces cerevisiae*.

Figure 3:
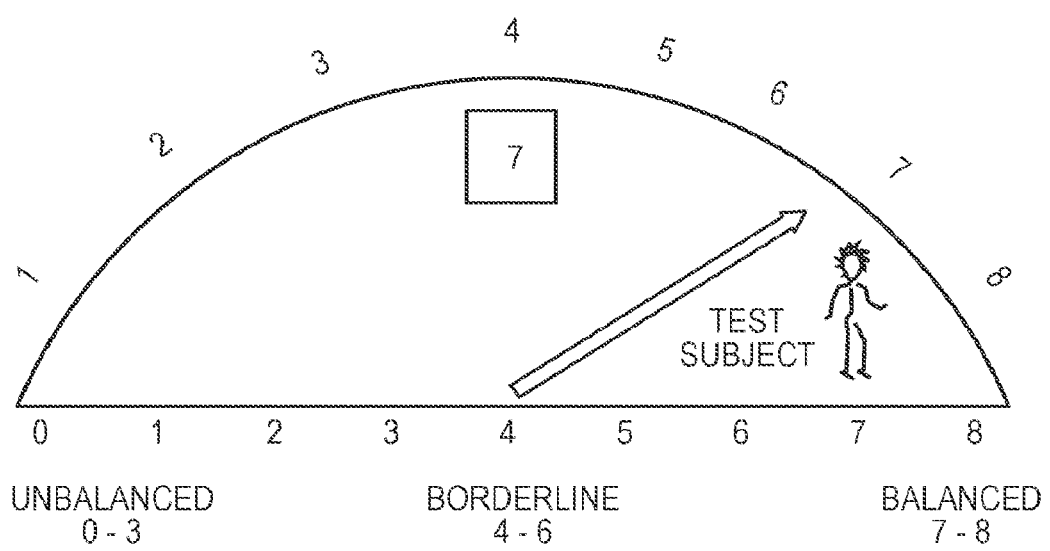
FIG. 3 is a schematic representation of a Biohm Balance Score ("BBS") system. A cumulative score of 8 for all organisms (e.g., in a given sample the tested bacterial and fungal organisms are present at higher levels than in the control sample, thus each is assigned a score of "1") identifies the subject as having a "balanced" microbiome. Likewise, a score of 7 identifies the subject as having a balanced microbiome. In contrast, a score of 4-6 identifies the subject as having a microbiome that is borderline between balanced and unbalanced microbiome, and a score of 0-3 identifies the subject as having an "unbalanced" microbiome, and a good candidate for receiving the composition of the invention.

In cases when the number or density of one of the organisms in the sample from the test subject is less than the number or density of the corresponding organism present in the corresponding region of the healthy subject, a score of "0" (zero) is assigned. Conversely, in cases when the number or density of one of the organisms in the sample from the test subject is equal to or more than the number or density of the corresponding organism present in the corresponding region of the healthy subject, a score of "1" is assigned. A cumulative score of 8 for all organisms (i.e., in a given sample all tested bacterial and fungal organisms are higher than in the control sample, thus each is assigned a score of "1") identifies the subject as having a "balanced" microbiome (FIG. 3). Likewise, a score of 7 identifies the subject as having a balanced microbiome (FIG. 3). In contrast, a score of 4-6 identifies the subject as having a microbiome that is borderline between balanced and unbalanced microbiome, and a score of 0-3 identifies the subject as having an "unbalanced" microbiome (FIG. 3).

When the score of the test subject is 0-3, then the test subject is identified as suitable candidate for treatment by disrupting a biofilm comprising pathogenic bacteria and pathogenic fungus with a dosage form comprising a composition of one or more non-pathogenic bacterial strains, an enzyme, and a non-pathogenic fungal strain. When the score of the test subject is 4-6, then the test subject is identified as suitable for treatment after further monitoring for 2-6 weeks. When the score of the test subject is 7-8, the test subject is identified as being healthy, where the subject does not need treating with a dosage form described herein.

(VIII) Definitions

The following definitions are included for the purpose of understanding the present subject matter and for constructing the appended patent claims.

Throughout the description, where compositions are described as having, including, or comprising specific components, or where processes and methods are described as having, including, or comprising specific steps, it is contemplated that, additionally, there are compositions of the present invention that consist essentially of, or consist of, the recited components, and that there are processes and methods according to the present invention that consist essentially of, or consist of, the recited processing steps.

In the application, where an element or component is said to be included in and/or selected from a list of recited elements or components, it should be understood that the element or component can be any one of the recited elements or components, or the element or component can be selected from a group consisting of two or more of the recited elements or components.

Further, it should be understood that elements and/or features of a composition or a method described herein can be combined in a variety of ways without departing from the spirit and scope of the present invention, whether explicit or implicit herein. For example, where reference is made to a particular composition, that composition can be used in the various embodiments of such compositions of the present invention and/or in methods of the present invention, unless otherwise understood from the context. In other words, within this application, embodiments have been described and depicted in a way that enables a clear and concise application to be written and drawn, but it is intended and will be appreciated that embodiments may be variously combined or separated without parting from the present teachings and invention(s). For example, it will be appreciated that all features described and depicted herein can be applicable to all aspects of the invention(s) described and depicted herein.

It should be understood that the expression "at least one of" includes individually each of the recited objects after the expression and the various combinations of two or more of the recited objects unless otherwise understood from the context and use. The expression "and/or" in connection with three or more recited objects should be understood to have the same meaning unless otherwise understood from the context.

The use of the term "include," "includes," "including," "have," "has," "having," "contain," "contains," or "containing," including grammatical equivalents thereof, should be understood generally as open-ended and non-limiting, for example, not excluding additional unrecited elements or steps, unless otherwise specifically stated or understood from the context.

Where the use of the term "about" is before a quantitative value, the present invention also includes the specific quantitative value itself, unless specifically stated otherwise. As used herein, the term "about" refers to a ±10% variation from the nominal value unless otherwise indicated or inferred.

Where a molecular weight is provided and not an absolute value, for example, of a polymer, then the molecular weight should be understood to be an average molecule weight, unless otherwise stated or understood from the context.

It should be understood that the order of steps or order for performing certain actions is immaterial so long as the present invention remain operable. Moreover, two or more steps or actions may be conducted simultaneously.

At various places in the present specification, components, or features thereof are disclosed in groups or in ranges. It is specifically intended that the description include each and every individual sub-combination of the members of such groups and ranges. By way of other examples, an integer in the range of 1 to 20 is specifically intended to individually disclose 1, 2, 3, 4, 5, 6, 7, 8, 9, 10, 11, 12, 13, 14, 15, 16, 17, 18, 19, and 20.

The use of any and all examples, or exemplary language herein, for example, "such as" or "including," is intended merely to illustrate better the present invention and does not pose a limitation on the scope of the invention unless claimed. No language in the specification should be construed as indicating any non-claimed element as essential to the practice of the present invention.

As a general matter, compositions specifying a percentage are by weight unless otherwise specified.

Practice of the invention will be more fully understood from the foregoing examples, which are presented herein for illustrative purposes only, and should not be construed as limiting the invention in any way.

EXAMPLES

The following Examples are merely illustrative and are not intended to limit the scope or content of the invention in any way.

Example 1—Inhibition of Candida Tropicalis Filamentation in Mature Biofilms by Probiotic Bacterial and Fungal Strains In this Example, a composition comprising four non-pathogenic microbial strains (three bacterial and one fungal strains) including *Lactobacillus rhamnosus, Lactobacillus acidophilus, Bifidobacterium breve,* and *Saccharomyces boulardii* ("the probiotic strains") was used to disrupt (treat) a mixed-species biofilm formed by the pathogenic microorganisms *Candida tropicalis, Escherichia coli,* and *Serratia marcescens*.

The probiotic strains *Lactobacillus rhamnosus, Lactobacillus acidophilus* and *Saccharomyces boulardii* with starting cell number of approximately $10^6$ CFUs per strain were cultured in yeast nitrogen base (YNB) and brain heart infusion (BHI) broth (ratio of the YNB and BHT broth was 1:1) in a sterile 50 mL conical tube, and incubated at 37° C. for 24 hours. *B. breve* with starting cell number of approximately $10^6$ CFUs was cultured in anaerobic conditions in YNB and BHI broth (ratio of the YNB and BHI broth was 1:1) in a sterile 50 mL conical tube and incubated at 37° C. for 24 hours. After 24 hours of cell growth, the two cultures were mixed and then gently centrifuged at 1,500 g for 5 minutes to retain some of the probiotic strains in the supernatant. The supernatant containing the probiotic strains was then decanted from the tube, and was stored at −20° C. until use.

Biofilms were formed on silicon elastomer (SE) discs. Single (*C. tropicalis* alone) and mixed-species (*C. tropicalis, E. coli,* and *S. marcescens*) inocula were added to 12-well plates containing SE discs that had previously been soaked in fetal bovine serum (1-BS) for 24 hours, and allowed to adhere to the surface for 90 minutes. After the adhesion phase, the discs were rinsed twice with phosphate buffered saline (PBS) to remove any non-adhered cells, and then placed in a new 12-well plate containing 4 mL of YNB/BHI media at a 1:1 concentration. The plates were then incubated at 37° C. for 24 hours to allow biofilm maturation. After the maturation phase, biofilms were removed and carefully rinsed with PBS, and placed into a new 12-well plate containing the probiotic containing supernatant and incubated at 37° C. for an additional 24 hours.

Next, the discs were rinsed with sterile PBS and placed in 2% glutaraldehyde for 24 hours at 4° C. Following fixation, the discs were prepared for scanning electron microscopy (SEM). Briefly, the fixed discs were rinsed in 0.1M sodium cacodylate 3 times for 10 minutes each. The discs were then placed in 1% osmium tetroxide for 1 hour at 4° C. After secondary fixation in osmium tetroxide, the discs were rinsed again in 0.1M sodium cacodylate 3 times for 10 minutes each, and placed in uranyl acetate overnight at 4° C. The discs were removed and rinsed twice in sterile water for 5 minutes each before being passing through a gradual ethanol dehydration process using 25, 50, 75, 95, and 100% ethanol. Once air dried, the samples were placed in a desiccator for 48 hours to complete the dehydration process. The dehydrated samples were sputter coated with palladium for 60 seconds and viewed with the Nova NanoLab 200 FEG-SEM/FIB scanning electron microscope in high-vacuum mode.

Figure 1B:
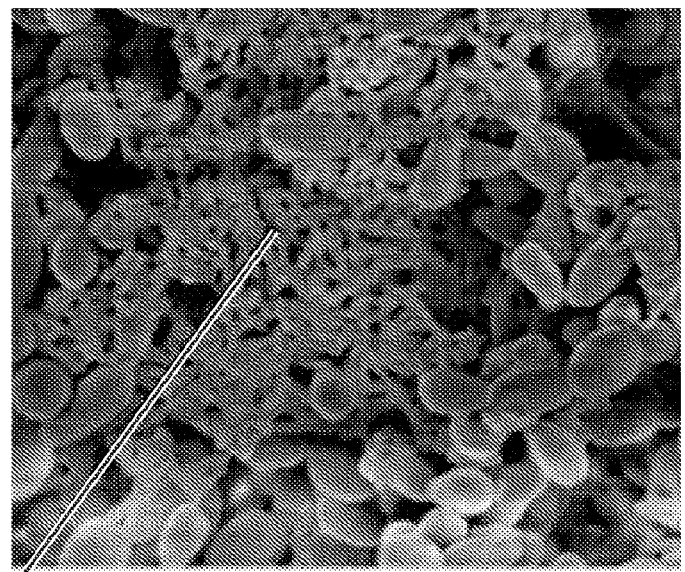
Figure 2A:
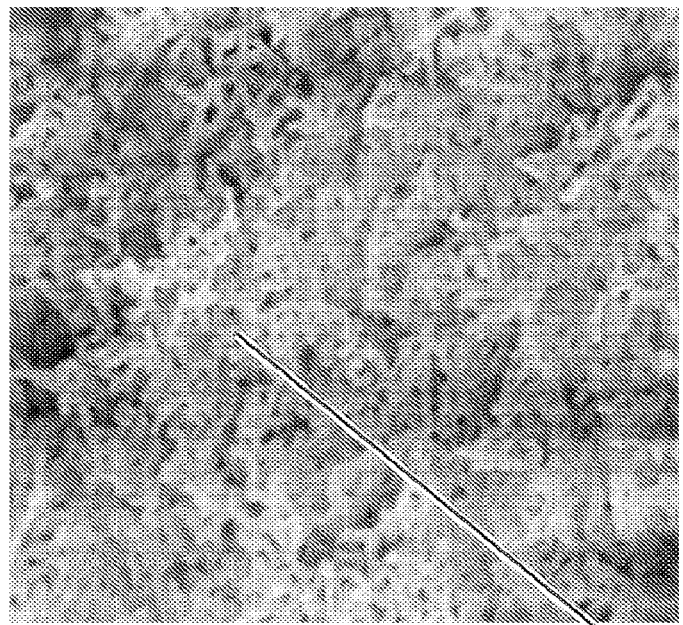
FIGS. 2A-2B are photographs showing effects of probiotic strains on mixed-species biofilms formed by pathogenic organisms where FIG. 2A (500× magnification) and FIG. 2B (1,000× magnification) show that fungal hyphenation is significantly reduced in the mixed-species biofilm after being treated with the probiotic strains, compared to the mixed species biofilm control.
Figure 2B:
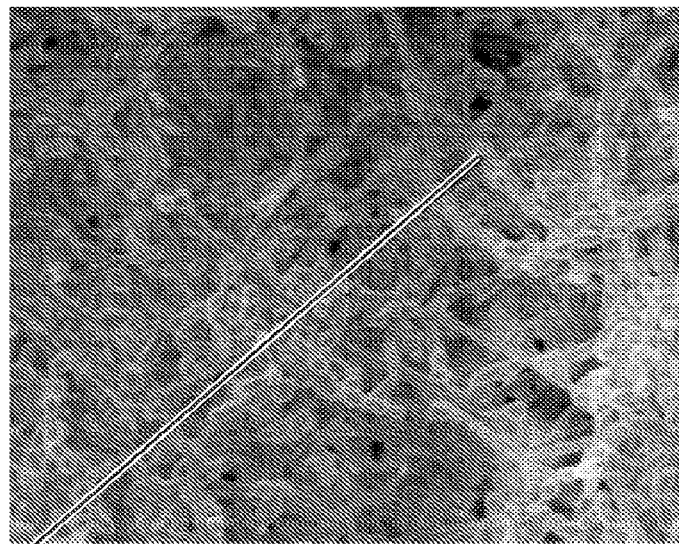

Treatment of the biofilms with the probiotic strains led to a reduction in the ability of *Candida* to form filaments (a well-known virulence factor of *Candida* species) both in single species (FIGS. 1A and 1B) and triple mixed-species biofilms (FIGS. 2A and 2B). The data demonstrated that by inhibiting fugal filamentation, the probiotic strains (*Lactobacillus rhamnosus, Lactobacillus acidophilus, Bifidobacterium breve, Saccharomyces boulardii*) are capable of reducing the virulence of *Candida* and therefore, prevent them from invading the epithelial mucosa.

Example 2—Disruption of a Biofilm Comprising Pathogenic Organisms with a Composition Comprising Non-pathogenic Bacterial and Fungal Strains, and an Enzyme In this Example, a composition of four non-pathogenic microbial strains, *Lactobacillus rhamnosus, Lactobacillus*

*acidophilus, Bifidobacterium breve, Saccharomyces boulardii* ("the probiotic strains") and an enzyme is used to disrupt a biofilm formed by the pathogenic microorganisms *Candida tropicalis, Escherichia coli*, and *Serratia marcescens*.

The probiotic strains are grown as described in Example 1. The probiotic strains is collected from the supernatant or the cell pellets obtained after centrifugation. An enzyme (e.g., amylase), is added to the pellet and the resulting enzyme containing composition is stored at −20° C. until use. Amylases added to the composition may be *Bacillus slearolhermophilus* amylase, *Bacillus amyloliquefaciens* amylase, *Bacillus subtilis* amylase, *Bacillus licheniformis* amylase, *Aspergillus niger* amylase, and/or *Aspergillus oryzae* amylase.

Biofilms are created as described in Example 1. After biofilm formation, the discs are rinsed twice with PBS to remove any non-adhered cells, and then placed in a new 12-well plate containing 4 mL of the probiotic-enzyme composition. The plates are then incubated at 37° C. for 24 hours, after which the biofilms are removed and carefully rinsed with PBS, and placed in 2% glutaraldehyde for 24 hours at 4° C. Following fixation, the discs are prepared for scanning electron microscopy (SEM) as described in Example 1.

It is contemplated that the addition of the composition comprising the nonpathogenic bacterial and fungal strains and an enzyme to the mixed-species biofilm will be effective at inhibiting the growth of the biofilm compared to the untreated control biofilm that produces a very large, dense plaque, with an extensive network of hyphae.

Example 3—Method of Identifying a Test Subject Suitable for Treatment

This Example describes a method of identifying whether a test subject is suitable for treatment with a dosage form described herein.

The number or density of the non-pathogenic bacterial strains and the non-pathogenic fungal strains are measured and quantified from the harvested sample. Examples of non-pathogenic bacteria that are quantified include *Lactobacillus rhamnosus, Lactobacillus acidophilus*, and *Bifidobacterium breve*. Examples of non-pathogenic fungi that are quantified include Saccharonyces *boulardii* and *Saccharomyces* cerev isiae.

The number or density of non-pathogenic microorganisms quantified in the sample of the candidate subject is then compared against the number or density of corresponding organisms in a corresponding sample size of a corresponding region of a healthy subject. In cases when the number or density of one of the organisms in the sample from the test subject is less than the number or density of the corresponding organism present in the corresponding region of the healthy subject, a score of "0" (zero) is assigned. Conversely, in cases when the number or density of one of the organisms in the sample from the test subject is equal to or more than the number or density of the corresponding organism present in the corresponding region of the healthy subject, a score of "1" is assigned. A cumulative score of 8 for all organisms (i.e., in a given sample all tested bacterial and fungal organisms are higher than in the control sample, thus each is assigned a score of "1") identifies the subject as having a "balanced" microbiome (FIG. 3). Likewise, a score of 7 identifies the subject as having a balanced microbiome (FIG. 3). In contrast, a score of 4-6 identifies the subject as having a microbiome that is borderline between balanced and unbalanced microbiome, and a score of 0-3 identifies the subject as having an "unbalanced" microbiome (FIG. 3).

When the score of the test subject is 0-3, then the test subject is identified as suitable candidate for treatment by disrupting a biofilm comprising pathogenic bacteria and pathogenic fungus with a dosage form comprising a composition of one or more non-pathogenic bacterial strain, an enzyme, and a non-pathogenic fungal strain. When the score of the test subject is 4-6, then the test subject is identified as suitable for treatment after further monitoring for another 2-6 weeks. When the score of the test subject is 7-8, the test subject is identified as being healthy, not suitable for treatment with the compositions described herein.

Example 4—Effects of Probiotic Consumption on the Bacteriome and Mycobiome

In this Example, a slow food cohort (SFC) received probiotic capsules, referred to herein as BIOHM capsules, and the effect on the bacteriome and mycobiome profiles of the cohort subjects were analyzed. The BIOHM capsule for once per day administration comprises hydroxypropylmethylcellulose (HPMC)-coated powder that contains about 15 billion colony forming units of *Bifidobacterium breve*, about 1.5 billion colony forming units of *Lactobacillus acidophilus*, about 10 billion colony forming units of *Lactobacillus rhamnosus*, and about 3.5 billion *Saccharomyces boulardii*, and admixed with about 500 SKB units of amylase.

Fecal samples were collected from a slow food cohort (SFC) (n=21) before (baseline) and after receiving one BIOHM capsule per day for four weeks. The collected samples were analyzed for levels of their bacterial communities using Ion-Torrent sequencing platform (Thermo Fisher). Pre- and Post-BIOHM data were analyzed for each sample and compared to corresponding data from the Normal Human Microbiome Project subjects (NHMPS).

Abundance profiles the bacteriome and mycobiome were generated and imported into Partek Discovery Suite (v6.11) for principal component analysis (PCA). Statistical significance levels were calculated comparing the changes across groups by t-Test for a given species or phylum. A p-value <0.05 was considered significant.

Bacteriome

Figure 4:
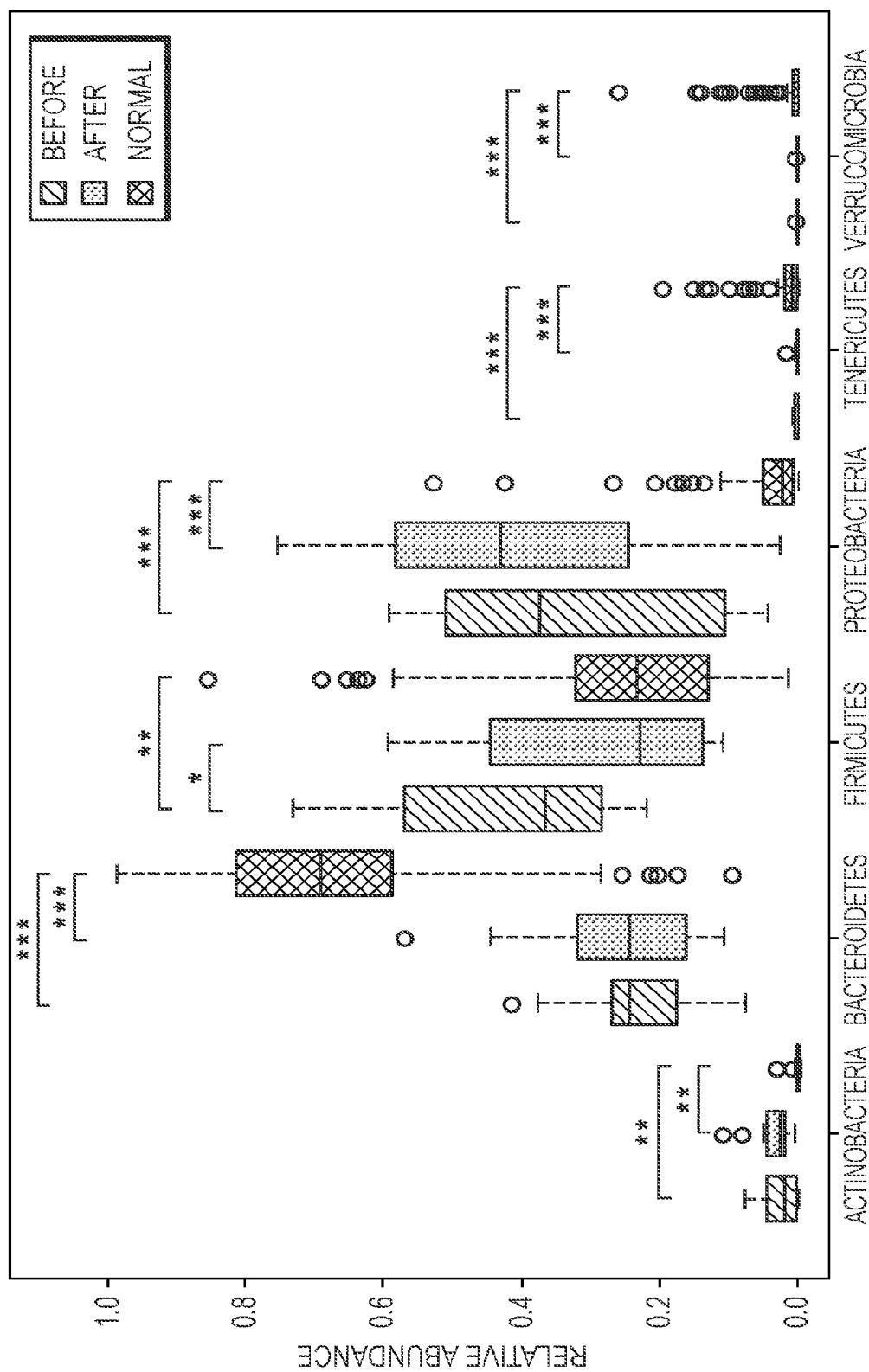
FIG. 4 is a series of box plots showing relative abundance profiles of six bacterial phyla analyzed in a slow food cohort (SFC). For each phylum, levels of bacteria were analyzed before and after administration of a capsule comprising a composition of the present invention. The pre- and post-administration profile was compared to the profiles from the Normal Human Microbiome Project subjects (NHMPS). Statistical significance levels: * <0.01, <0.001, *<0.

Prior to treatment, as shown in FIG. 4, subjects in the SFC had significantly lower levels of Bacteroidetes (both pre- and post-BIOHM) compared to the NHMPS. The level of Firmicutes phylum was higher at baseline in SFC subjects compared to the NHMPS. Subjects in the SFC had significantly higher levels of Proteobacteria phylum (both pre- and post-BIOHM) compared to the NHMPS. The phyla Actinobacteria, Tenericutes, and Verrucomicrobia were detected at low abundance in all subjects irrespective of the time of collection.

Post-treatment, subjects in the SFC, upon administration of the BIOHM capsule displayed a reduction in the abundance of the Firmicutes phylum, where the level in the post-BIOHM samples mirrored that of the NHPMS. However, no significant changes between pre- and post-treatment were observed across the other bacterial phyla.

Mycobiome

Figure 5:
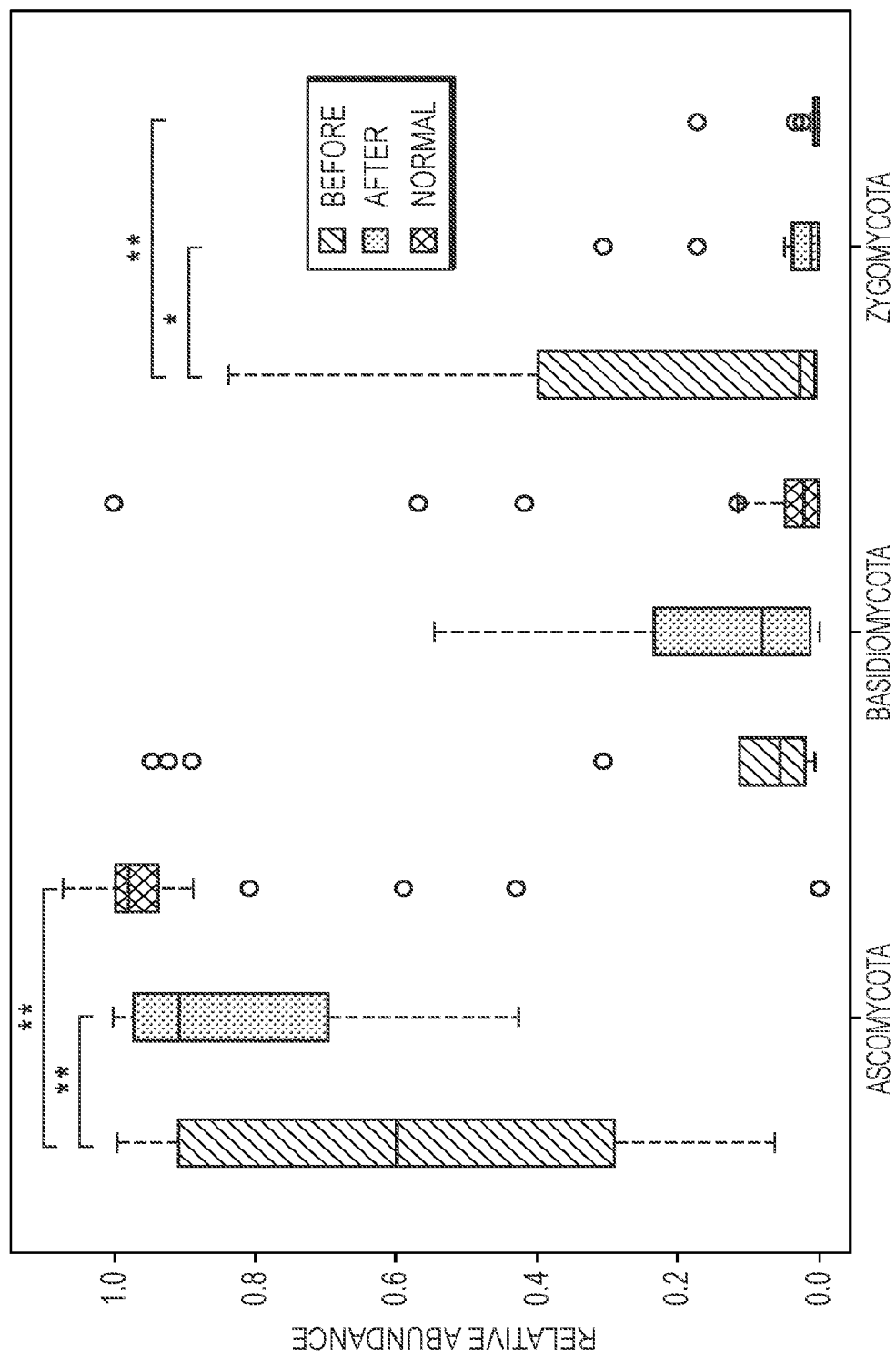
FIG. 5 is a series of box plots showing relative abundance profiles of three fungal phyla analyzed in the SFC. For each phylum, levels of fungi were analyzed before and after receiving a capsule containing probiotic composition described herein called a BIOHM capsule, and compared to the profile of the NHMPS. Statistical significance levels: * <0.01, **<0.001.

Prior to treatment, as shown in FIG. 5, subjects in the SFC had significantly lower levels of Ascomycota phylum at baseline compared to the NHMPS. The levels of Zygomycota phylum of SFC was higher at baseline compared to the NHMPS. No significant difference in Basidiomycota was observed in the SFC subjects compared to the NHMPS, and no statistically significant difference in the Basidiomycota was detected between before and after BIOHM administered samples and the NHMPS.

Post-treatment, subjects in the SFC, upon administration of the BIOHM capsule displayed an increase in Ascomycota levels. Moreover, the abundance of this phylum increased to match those of the NHMPS (p>0.05). Furthermore, a reduction in Zygomycota level was observed following BIOHM capsule administration (p<0.01). The abundance of this phylum decreased to match those of the NHMPS (p>0.05).

Example 5—Modification of *Candida* Species and *Candida albicans* Upon Probiotic Consumption In this Example, the slow food cohort (SFC) of Example 4, that consumed the probiotic capsules was analyzed to determine the effect of treatment on the *Candida* spp. and *Candida albicans* levels of the cohort subjects. Abundance profiles were generated and imported into Partek Discovery Suite (v6.11) for principal component analysis (PCA).

Figure 6:
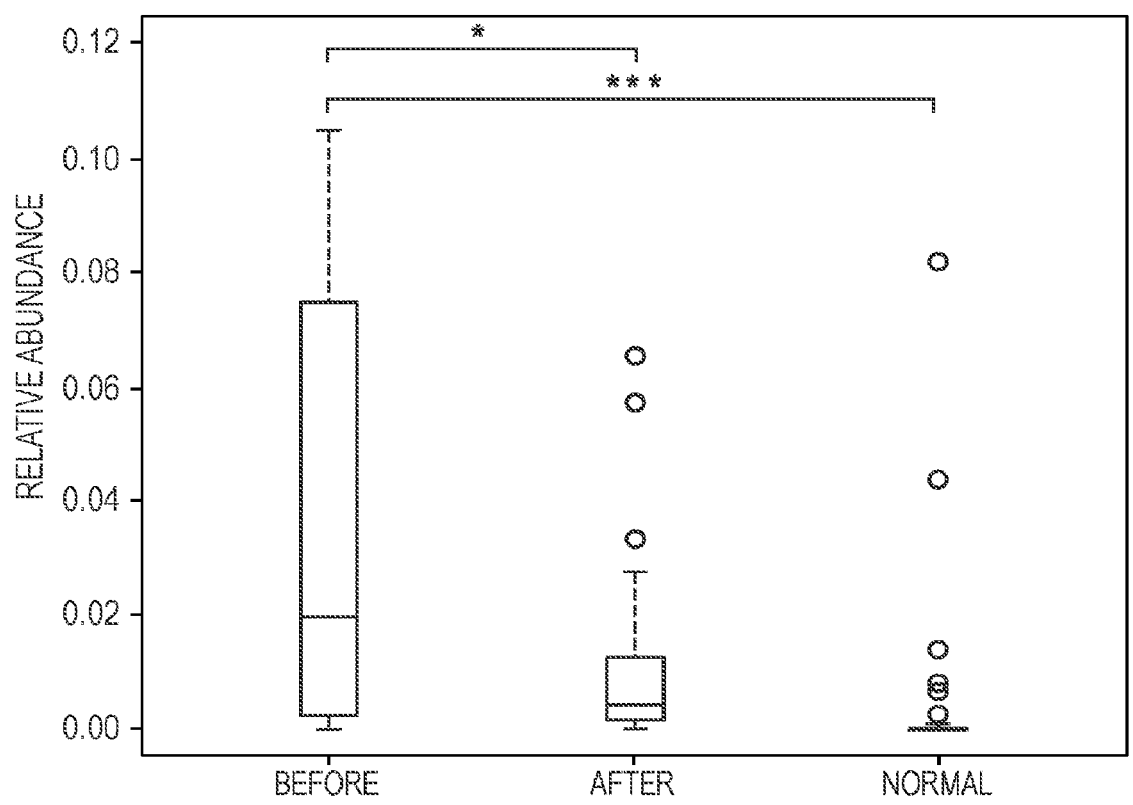
FIG. 6 shows box plots showing a relative abundance profile of the *Candida* genus in subjects analyzed in the SFC. Levels of *Candida* genus were analyzed before and after BIOHM capsule consumption, and compared to the profile of healthy control subjects. Statistical significance levels: * <0.01, **<0.001.
Figure 7:
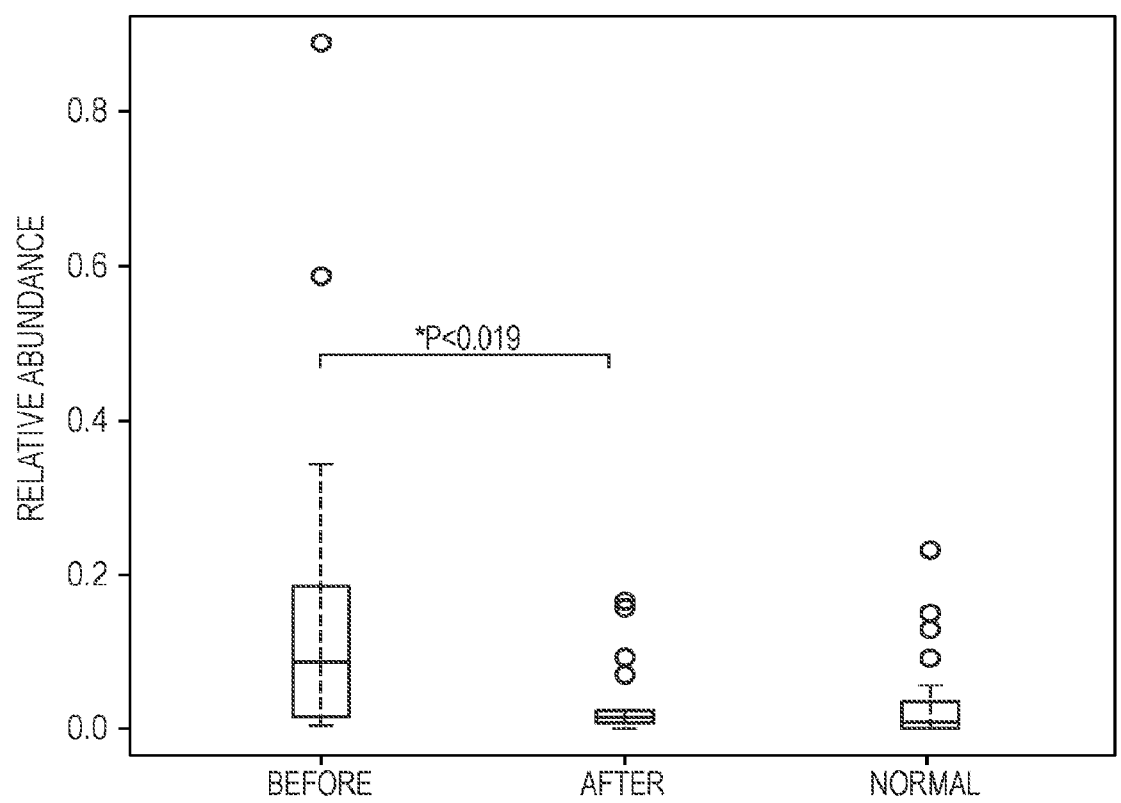
FIG. 7 shows box plots showing a relative abundance of the *Candida albicans* species in subjects analyzed in the SFC. Levels of *Candida albicans* were analyzed before and after BIOHM capsule administration, and compared to the profile of healthy control subjects. Statistical significance levels: * <0.01, <0.001, *<0.

Prior to treatment, as shown in FIG. 6 and FIG. 7, at baseline both *Candida* genus and *Candida albicans* species levels in the SFC subjects were significantly higher compared to the NHMPS (p<0.019 and <0.0001, respectively).

After treatment, subjects in the SFC, upon administration of the probiotic capsule displayed a significant reduction of both *Candida* spp. and *Candida albicans* (p<0.01 and <0.0001, respectively). The results described in Examples 4 and 5 demonstrate (i) a reduction in the abundance of Firmicutes bacterial phylum mirrors that of the NHMPS, (ii) an increase in Ascomycota levels that match those of NHMPS, (iii) a reduction in Zygomycota levels that match those of NHMPS, and (iv) a significant reduction in the abundance of both *Candida* spp. and *C. albicans*. Together, the results show that the use of probiotic therapy modifies gut fungal and bacterial microbiota.

Example 6—Prevention and Treatment of Single and Mixed Species Biofilms by Probiotic Bacterial and Fungal Strains In this Example, a composition containing four non-pathogenic microbial strains (three bacterial strains and one fungal strain including *Lactobacillus rhamnosus*, *Lactobacillus acidophilus*, *Bifidobacterium breve*, and *Saccharomyces boulardii* ("the probiotic strains")) were used to treat biofilms formed by the pathogenic microorganisms *Candida tropicalis* or *Candida albicans*, either grown singly and as mixed species biofilms with *Escherichia coli* and *Serratia marcescens*.

The probiotic strains *Lactobacillus rhamnosus*, *Lactobacillus acidophilus*, and *Saccharomyces boulardii* were cultured in yeast nitrogen base (YNB) and brain heart infusion (BHI) broth (ratio of the YNB and BHI broth was 1:1) in a sterile 50 mL conical tube, and incubated at 37° C. for 24 hours. *B. breve* was cultured under anaerobic conditions in YNB and BHI broth (ratio of the YNB and BHI broth was 1:1) in a sterile 50 mL conical tube and incubated at 37° C. for 24 hours. After 24 hours of cell growth, the cultures were then centrifuged at 3,000 g for 5 minutes. The probiotic culture supernatants were then decanted and filter sterilized using 0.22 micron filters. The resulting filtrate was stored at −20° C. until use.

Biofilms were formed on silicon elastomer (SE) discs. *C. albicans*, *C. tropicalis*, or *Trichosporon* alone, or mixed with *E. coli* and *S. marcescens* inocula, were added to 12-well plates containing SE discs that had previously been soaked in fetal bovine serum (FBS) for 24 hours, and allowed to adhere to the surface of the SE discs for 90 minutes.

For analyzing the prevention of biofilm formation, after the adhesion phase, the discs were rinsed twice with phosphate buffered saline (PBS) to remove any non-adhered cells, and then placed in a new 12-well plate containing 4 mL of probiotic filtrate. The plates were then incubated at 37° C. for 24 hours to allow biofilm maturation.

For analyzing the treatment of mature biofilms, after the adhesion phase above, some biofilm discs were transferred into YNB+BHI media and allowed to mature for 24 hours at 37° C. After the maturation phase, biofilms were removed and rinsed with PBS, and placed into a new 12-well plate containing 4 mL of probiotic filtrate and were then further incubated at 37° C. for 24 hours.

Following the treatment of biofilms, the discs were stained with the dyes, Concanavalin Alexa fluor 488 conjugate and FUN-1. The discs were then observed under confocal scanning laser microscope (CSLM). Separate discs were fixed and prepared for scanning electron microscopy (SEM) following the protocol described in Example 1. The discs were viewed with the Helios NanoLab 650 scanning electron microscope in high-vacuum mode.

For analyzing effects on *Candida* germination, *Candida albicans*, or *Candida tropicalis* cells were inoculated in YNB medium for 18-20 hours and washed three times with Hank's Buffered Saline Solution (HBSS). Cells were counted and diluted to obtain $5 \times 10^5$ cells/ml. Probiotic filtrate was then added to the above concentration of cells in conical tubes. Cells with no probiotic filtrate were used as untreated controls. The conical tubes were incubated at 37° C. for 3 hours. At time zero, and at 30-minutes intervals, tubes were removed and vortexed. Cell suspension (10 µl) was transferred at each time point and cells were counted in a hemacytometer. Total cells and only geminated cells (defined as a germ-tube length greater than or equal to the diameter of a blastospore) were counted. The assay was discontinued after 3 hours and percent germinated cells (germinated cells per the total number of cells) were calculated for each time point. Confocal scanning laser microscope was used to observe the cells at each time points. All the experiments were done in triplicate.

Statistical analyses for all data were performed using GraphPad Prism 6 software. Probiotic-treated groups were compared to control untreated groups using unpaired t-tests. A p-value of 0.0.05 was considered significant.

Figure 8:
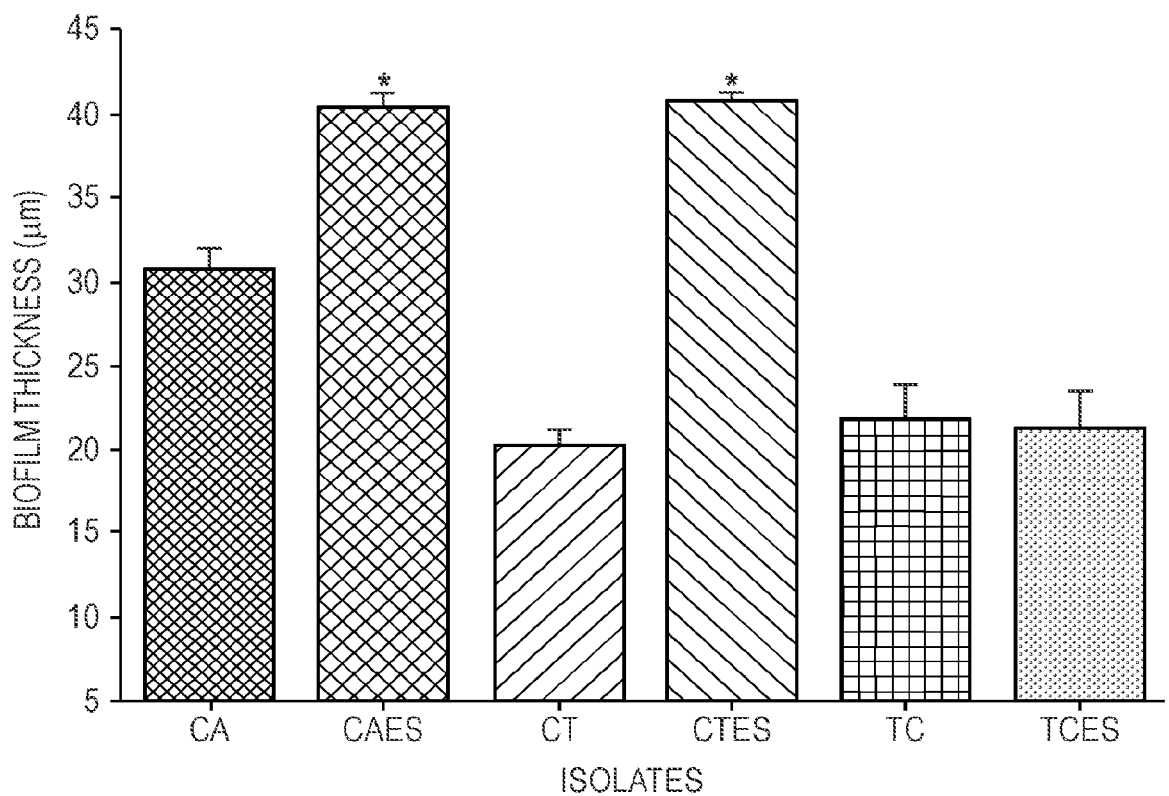
FIG. 8 is a graph showing the thickness of biofilms formed by *C. albicans* (CA), *C. tropicalis* (CT) or *Trichosporon* (TC) alone, and the thickness of mixed species biofilms formed by *C. albicans, E. coli* and *S. marcescens* (CAES), and *C. tropicalis, E. coli* and *S. marcescens* (CTES).

Results: To study the interaction between *C. tropicalis*, *E. coli*, and *S. marcescens* biofilms (CTES) or *C. albicans*, *E. coli*, and *S. marcescens* biofilms (CAES), and to determine if the interaction was specific, biofilms formed by the control fungus, *Trichosporon*, were analyzed. Unlike CAES or CTES, which formed robust biofilms and showed a significant increase in biofilm thickness (p≤0.05) compared to *C. albicans* or *C. tropicalis* alone, TCES biofilms (*Trichosporon*, *E. coli*, and *S. marcescens*) showed no difference in biofilm thickness compared to *Trichosporon* alone (FIG. 8). The observed lack of difference in biofilm thickness suggested that the interaction between *C. tropicalis*, *E. coli*, and *S. marcescens* (CTES) or *C. albicans*, *E. coli* and *S. marcescens* (CAES) may be *C. tropicalis* or *C. albicans* specific. Thus, *C. albicans* and *C. tropicalis* appear to form robust biofilms when mixed with *E. coli* and *S. marcescens* compared to *Trichosporon*.

When observed under CSLM, *C. albicans* single species and triple mixed species (CAES) biofilms grown in the presence of the probiotic filtrate demonstrated reduced biofilm matrix for both the adhesion phase and mature phase.

Figure 9:
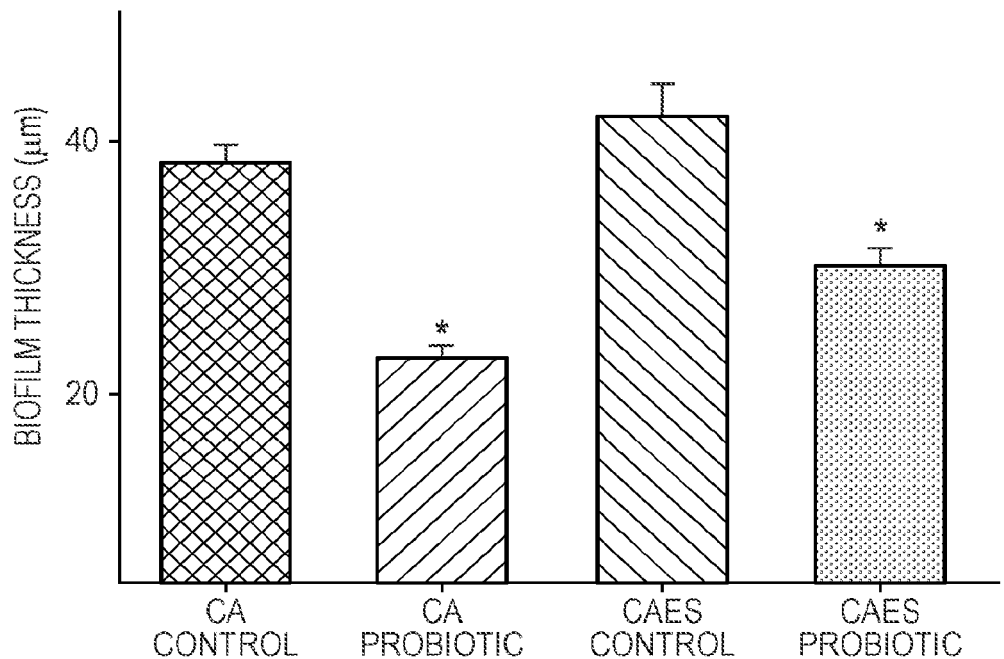
FIG. 9 is a graph showing the effect of the probiotic filtrate on the adhesion phase (prevention) of *C. albicans* biofilms formed alone and with mixed species. The thickness (μm) of biofilms formed by *C. albicans* alone (CA) and by mixed species *C. albicans, E. coli* and *S. marcescens* (CAES) are significantly reduced when treated with the probiotic filtrate, compared to the respective untreated controls (*p≤0.05).
Figure 11:
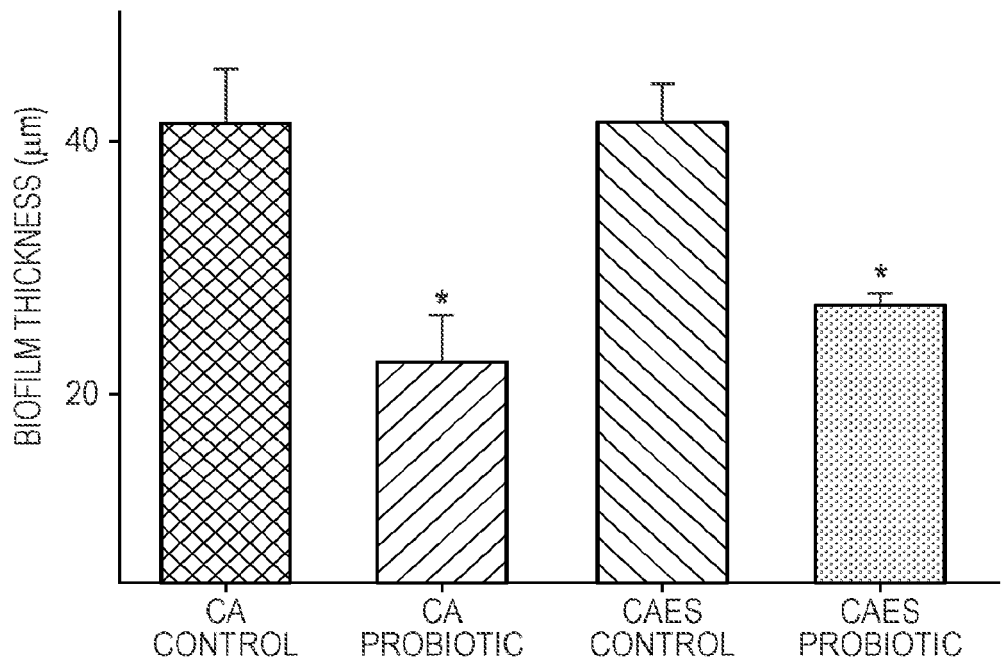
FIG. 11 is a graph showing the effect of the probiotic filtrate on the mature phase (treatment) of *C. albicans* biofilms formed alone and with mixed species. The thickness (μm) of biofilms formed by *C. albicans* alone (CA) and by mixed species *C. albicans, E. coli* and *S. marcescens* (CAES) are significantly reduced when treated with the probiotic filtrate, compared to the respective untreated controls (*p≤0.05).

Furthermore, the thickness of *C. albicans* single species and triple mixed species (CAES) biofilms exposed to probiotic filtrate was significantly reduced compared to untreated controls for both the adhesion and mature phase, respectively (FIGS. 9 and 11; p≤0.05).

Figure 10:
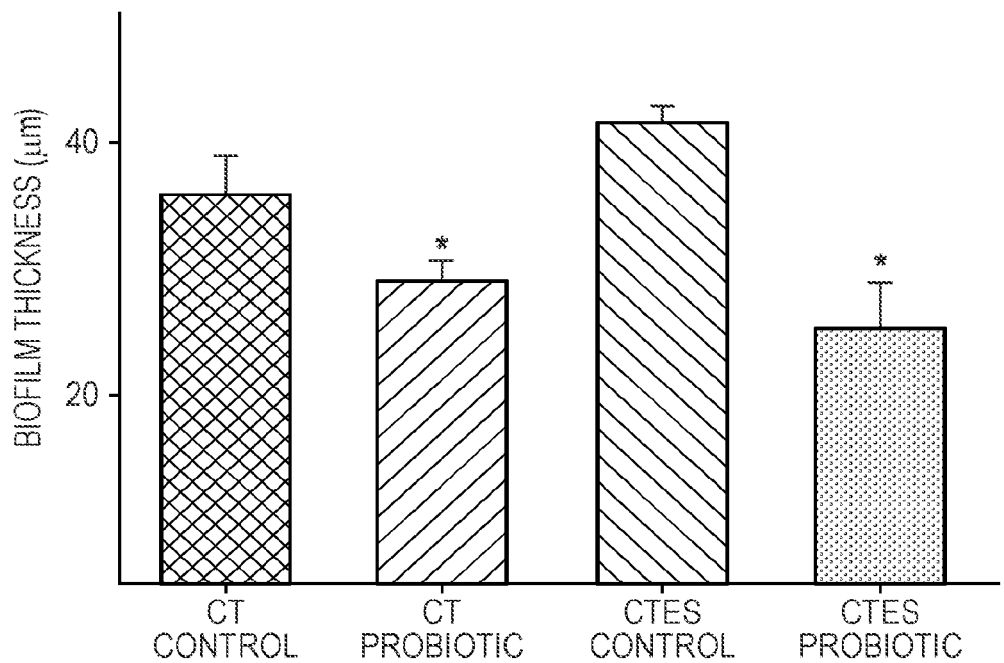
FIG. 10 is a graph showing the effect of the probiotic filtrate on the adhesion phase (prevention) of *C. tropicalis* biofilms formed alone (CT) and with mixed species. The thickness (μm) of biofilms formed by *C. tropicalis* alone (CT) and by mixed species *C. tropicalis, E. coli* and *S. marcescens* (CTES) are significantly reduced when treated with the probiotic filtrate, compared to the respective untreated controls (*p≤0.05).
Figure 12:
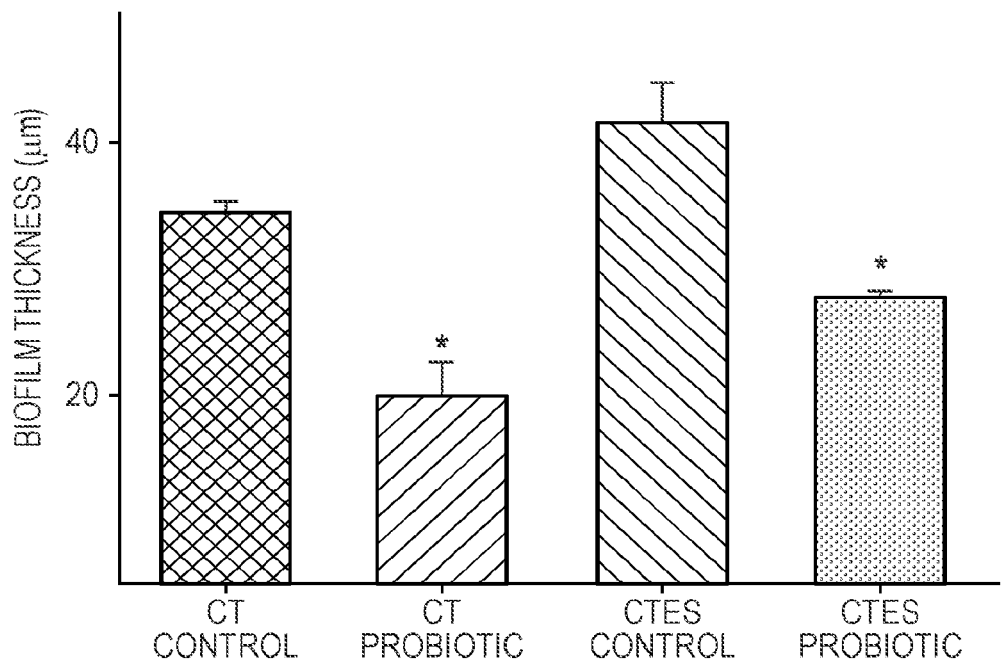
FIG. 12 is a graph showing the effect of the probiotic filtrate on the mature phase (treatment) of *C. tropicalis* biofilms formed alone (CT) and with mixed species. The thickness (μm) of biofilms formed by *C. tropicalis* alone (CT) and of mixed species *C. tropicalis, E. coli* and *S. marcescens* (CTES) biofilms is significantly reduced when treated with the probiotic filtrate compared to the respective untreated controls (*p≤0.05).

When observed under CSLM, *C. tropicalis* single species and triple mixed species (CTES) biofilms grown in the presence of the probiotic filtrate demonstrated reduced biofilm growth with decreased extracellular matrix for both the adhesion phase and mature phase. Furthermore, the thickness of *C. tropicalis* single species and triple mixed species (CTES) biofilms exposed to probiotic filtrate was significantly reduced compared to untreated controls for both the adhesion and mature phase, respectively (FIGS. 10 and 12; p≤0.05).

Figure 13B:
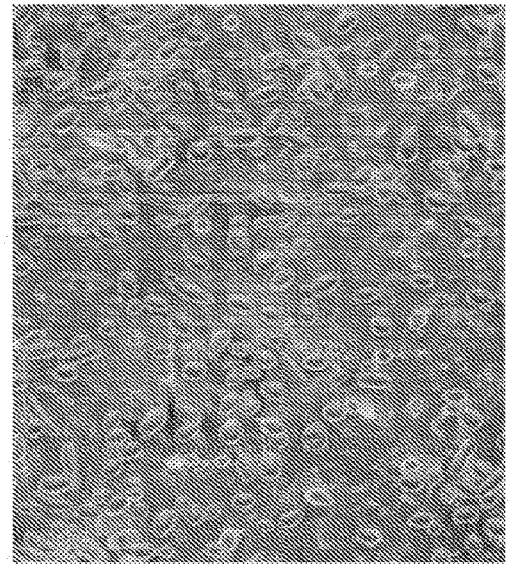
FIGS. 13A-13D are scanning electron micrographs (SEM) showing the effect of the Probiotic filtrate on the adhesion phase (prevention) of *C. albicans* biofilms alone and with mixed species.
Figure 13D:
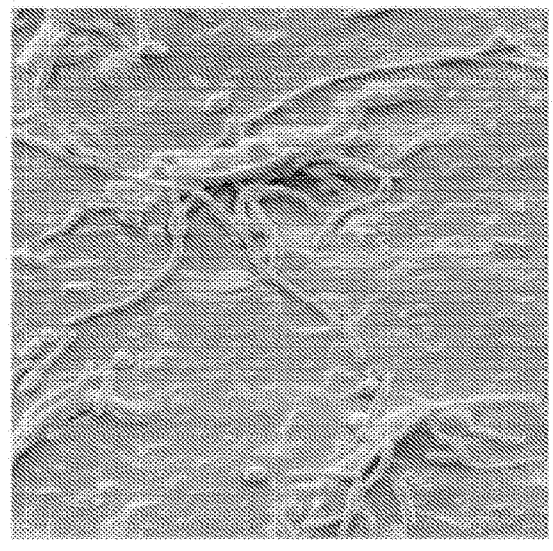
Figure 13A:
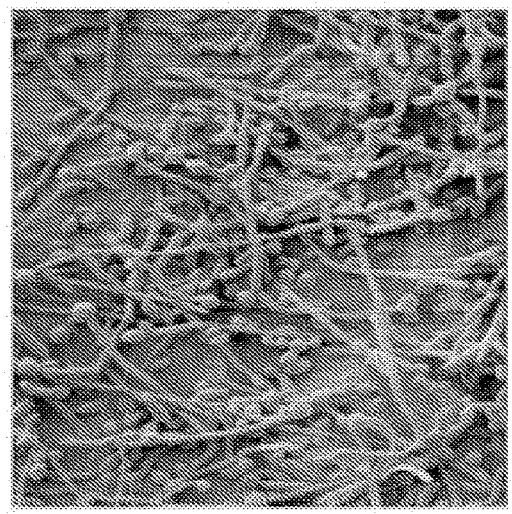
Figure 13C:
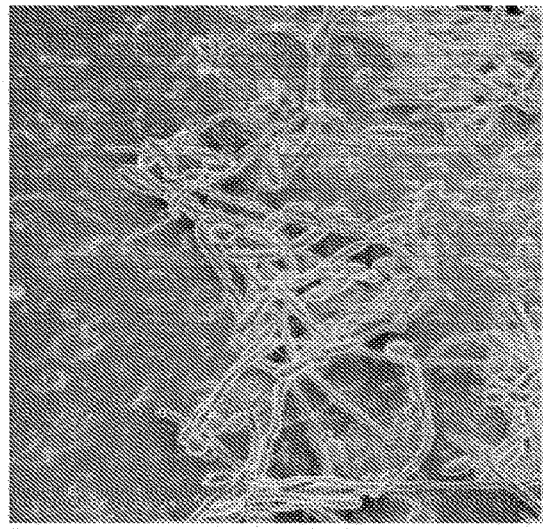

When observed under SEM, micrographs confirmed that, in contrast to untreated controls (FIGS. 13A & 13C), *C. albicans* single species and triple mixed species (CAES) biofilms grown in the presence of the probiotic filtrate demonstrated reduced biofilm growth with broken/deformed cells for the adhesion phase (FIGS. 13B & 13D).

Figure 14B:
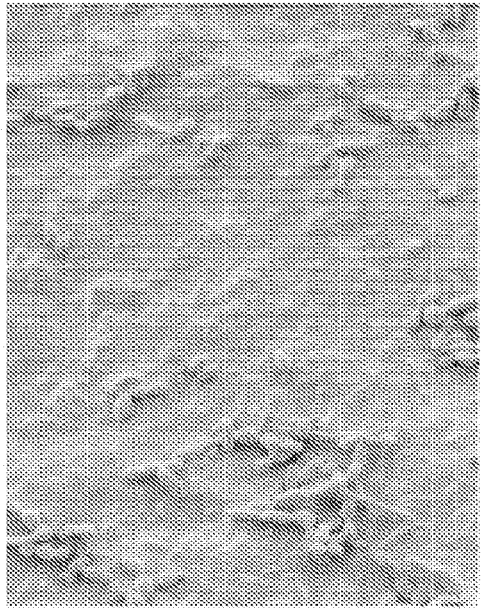
FIGS. 14A-14D are scanning electron micrographs (SEMs) showing the effect of the Probiotic filtrate on the adhesion phase (prevention) of *C. tropicalis* biofilms alone and with mixed species.
Figure 14D:
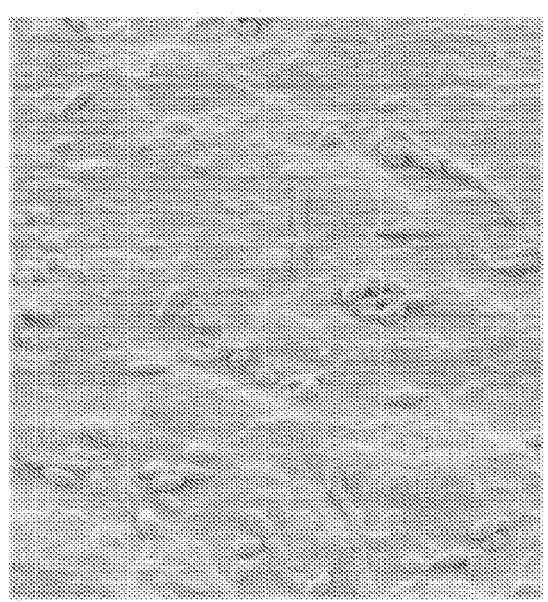
Figure 14A:
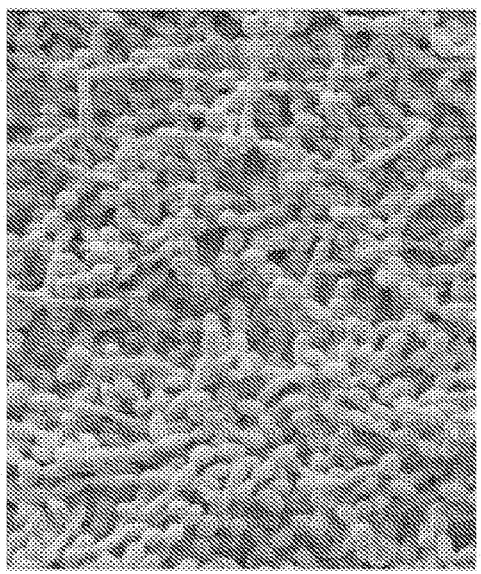
Figure 14C:
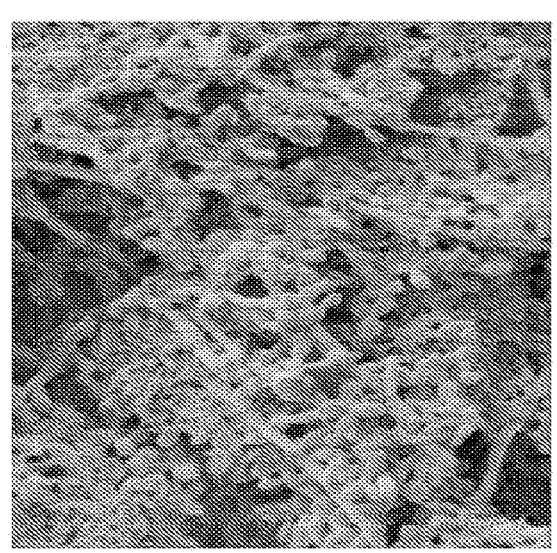

When observed under SEM, micrographs confirmed that, in contrast to untreated controls (FIGS. 14A & 14C), *C. tropicalis* single species and triple mixed species (CTES) biofilms grown in the presence of the probiotic filtrate demonstrated reduced biofilm growth for the adhesion phase (FIGS. 14B & 14D).

Figure 15:
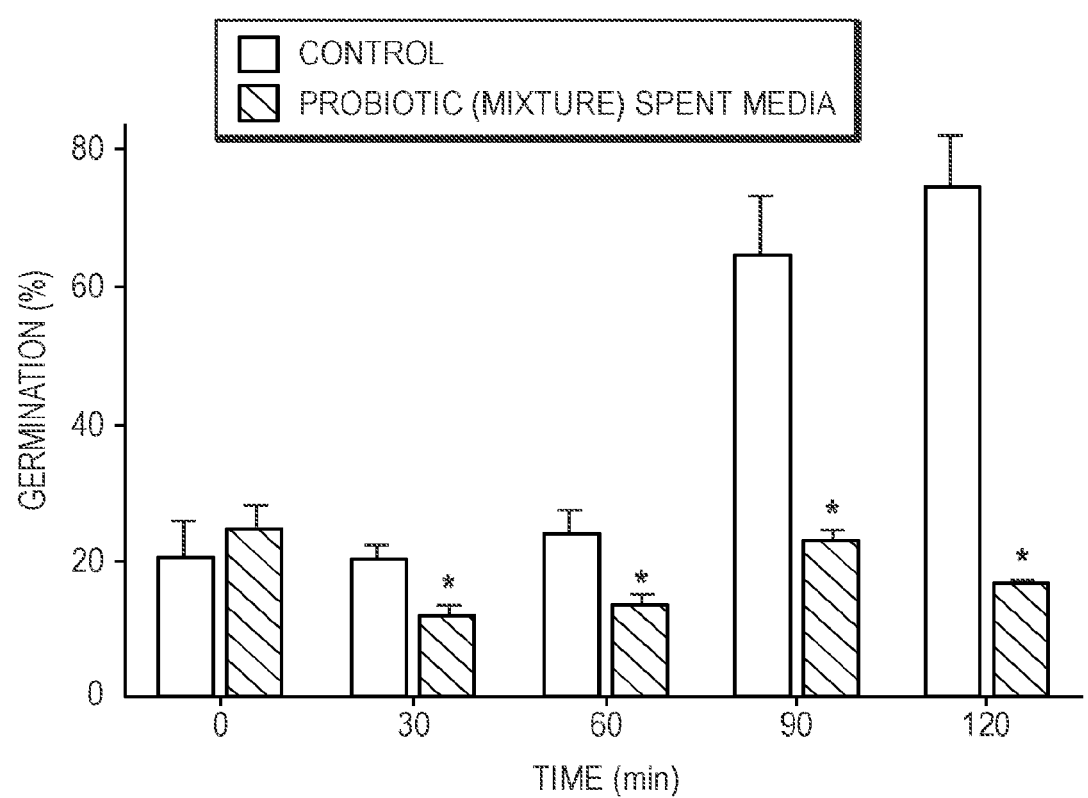
FIG. 15 is a graph showing the effect of the probiotic filtrate on *C. albicans* germination, for example, a significant reduction in percent *C. albicans* germ tube formation after 30 up to 120 minutes exposure to the probiotic filtrate compared to untreated control (*$p \leq 0.05$).
Figure 16:
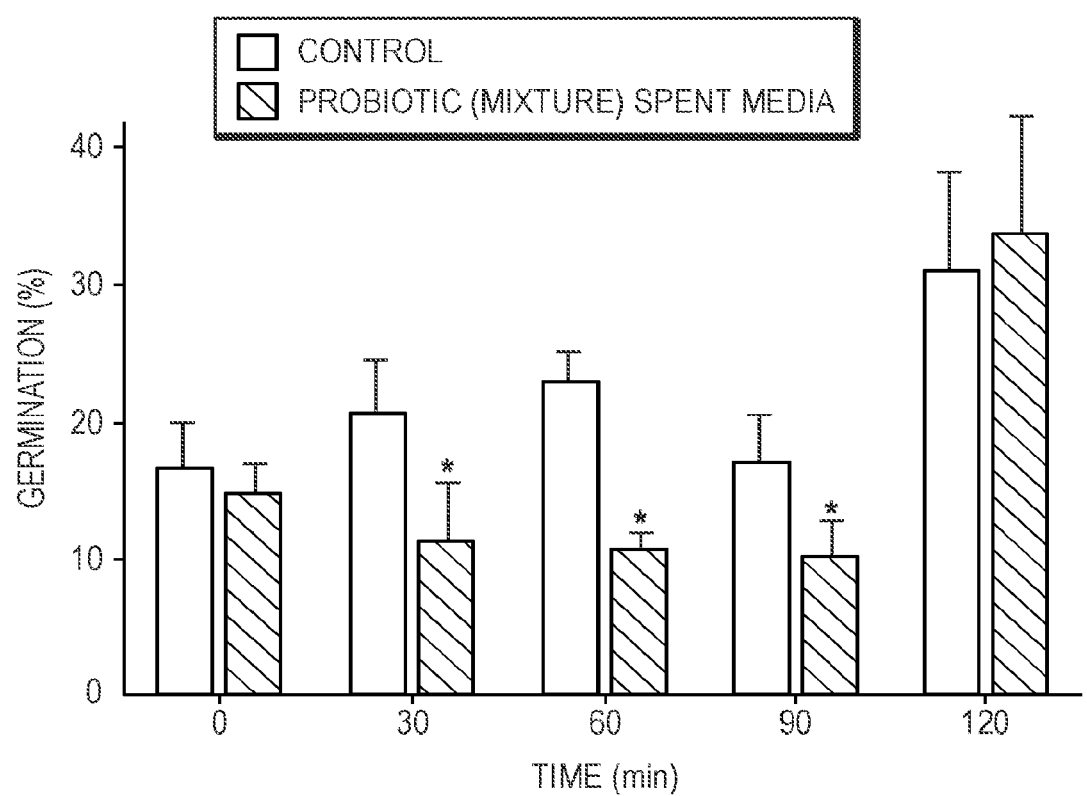
FIG. 16 is a graph showing the effect of the probiotic filtrate on *C. tropicalis* germination, for example, a significant reduction in percent *C. tropicalis* germ tube formation after 30 up to 90 minutes exposure to the probiotic filtrate compared to untreated control (*$p \leq 0.05$).

Upon analyzing the effects of the probiotic filtrate on the germination process, CSLM images showed that untreated *C. albicans* or *C. tropicalis* formed robust hyphae while exposure to probiotic filtrate resulted in stunted *C. albicans* or *C. tropicalis* germ tubes. There was a significant reduction in percent germ tube formation after a 30 minute exposure to probiotic filtrate for both *C. albicans* and *C. tropicalis* compared to their respective controls (FIGS. 15 and 16; p≤0.05). Probiotic filtrate had a significant effect on *C. albicans* percent germination up to 120 minutes (FIG. 15) and *C. tropicalis* percent germination up to 90 minutes (FIG. 16) compared to control.

Altogether, the data demonstrate that the tested probiotics (*S. boulardii, L. acidophilus, B. breve* and *L. rhamnosus*) reduced biofilm growth for both adhesion (prevention) and mature (treatment) phases for *C. albicans* and *C. tropicalis* grown as single species or as mixed species combined with *E. coli* and *S. marcescens*. Probiotic filtrate inhibited *Candida* germination with stunted germ tubes which did not develop into mature hypha for both *C. albicans* and *C. tropicalis*.

Example 7—Effects of the Probiotic Treatment on Nutrient Absorption

In this Example, a filter insert model was used to determine the effect of probiotic treatment upon nutrient absorption. The probiotic referred to as BIOHM (a composition of four non-pathogenic microbial strains, *Lactobacillus rhamnosus, Lactobacillus acidophilus, Bifidobacterium breve, Saccharomyces boulardii* and an enzyme) was found to disrupt a mixed species biofilm.

Figure 17:
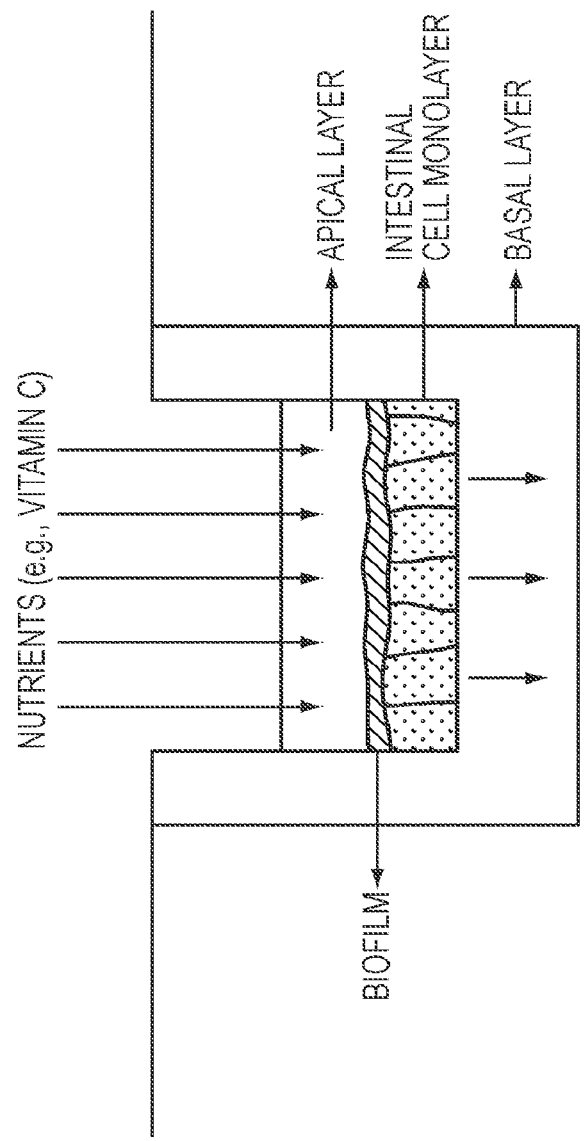
FIG. 17 is a schematic representation of a trans-well filter method, which is an in vitro model for evaluating nutrient absorption.

As depicted in FIG. 17, an intestinal epithelial cell line (Caco-2) was seeded onto the apical side of a transwell filter at a concentration of $1.5 \times 10^5$ cells/ml and was allowed to form a confluent monolayer for 10 days. Next, a mixed species biofilm including *Candida tropicalis, Escherichia coli*, and *Serratia marcescens* was permitted to form on top of the intestinal epithelial cell monolayer. Nutrients (e.g., glucose, dextran) were then added to the media inside the trans-well. BIOHM probiotic filtrate and normal growth media containing vitamin C was then added to the apical chamber and incubated for 6 hours. Control wells just received normal growth media containing vitamin C. Next, an aliquot from the basal chamber of the filter insert was removed and assayed for the amount of vitamin C that was absorbed through the intestinal epithelial monolayer using an L-ascorbic acid assay kit (Abnova). All tests were performed in quadruplicate. An unpaired t-test was used to compare treated and untreated samples. A p value <0.05 was considered significant.

Figure 18:
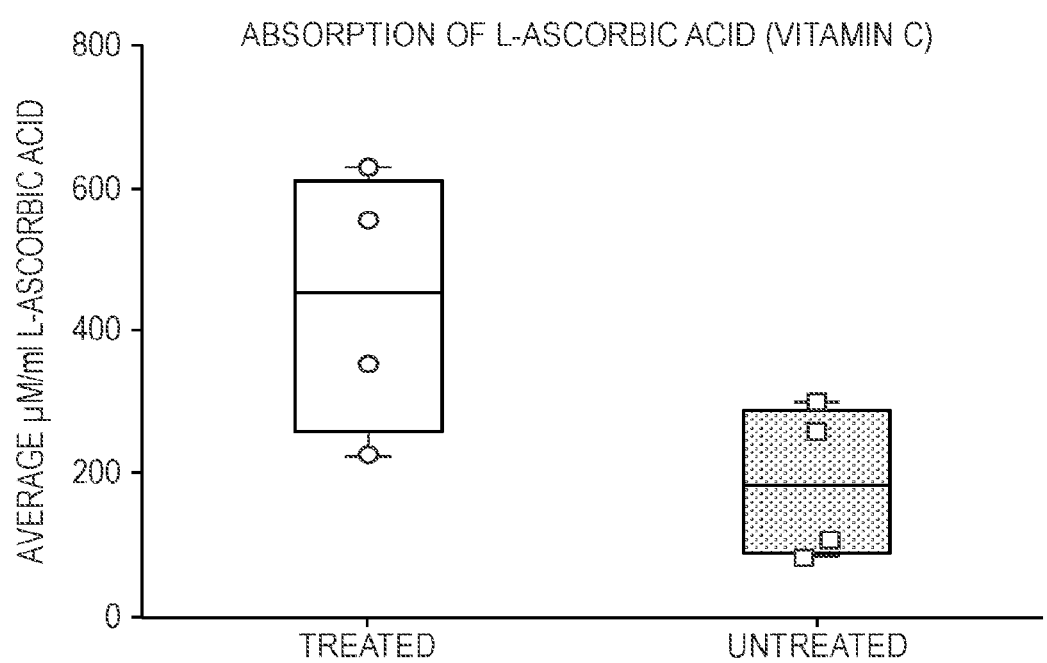
FIG. 18 is a graph showing the effect of the BIOHM probiotic filtrate on vitamin C absorption.

As shown in FIG. 18, treatment of mixed species biofilms formed on the Caco-2 cell monolayer with BIOHM probiotic filtrate resulted in higher transfer (absorption) of vitamin C compared to untreated controls (mean±SE: 440.8 μM/ml±92.22 μM/ml and 187.3 μM/ml±54.55 μM/ml for BIOHM probiotic treated and untreated biofilms, respectively, p value=0.055).

Example 8—Method of Preparing Baked Goods Comprising a Probiotic Composition

In this Example, a composition comprising four non-pathogenic microbial strains including *Lactobacillus rhamnosus, Lactobacillus acidophilus, Bifidobacterium breve*, and *Saccharomyces boulardii*, and the enzyme amylase (together referred to as "the probiotic") was added to a bread mix to determine whether the probiotic microbial strains would remain viable after baking.

A loaf of bread was prepared as follows: 484 mg of the probiotic containing the relative amounts of organisms and enzyme as set forth in Table 5 was added to 454 g of a commercially available bread mix. The bread and probiotic mixture was then poured into a mixing bowl and combined with the suggested amount of water. The combination was thoroughly mixed until the mixture became smooth. The mixture was poured into a loaf pan lightly coated in oil and was then left for 15-30 minutes in a warm location before baking. The bread mixture was then baked in an oven at 350° F. for 45-50 minutes. After baking, the bread was allowed to cool.

In order to test the viability of the probiotic microbial strains in the baked bread, three core samples were taken from the loaf using a cork borer. In order to eliminate any external bacterial contamination, the top layer of bread was removed and the 10 mm core samples were tested. Each sample was then weighed and homogenized in 16 mL of Phosphate buffered saline (PBS) using a Stomacher at the high setting for 2 minutes. Ten-fold serial dilutions of each homogenate were made and were then plated on different Petri dishes. Bacterial cultures were grown on Brain Heart Infusion agar in aerobic and anaerobic conditions, while yeast cultures were grown on Potato Dextrose Agar. Following incubation at 35° C. for 48 hours, the number of colony forming units (CFU) were counted.

Figure 19:
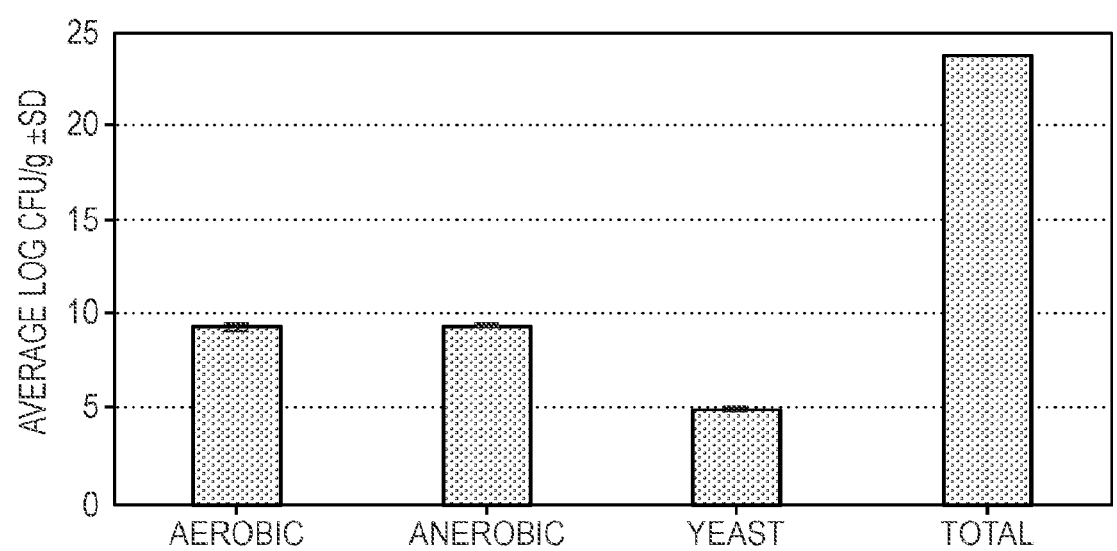
FIG. 19 is a bar graph showing the numbers (in log colony forming units (CFU)/g of bread) of aerobic bacteria, anaerobic bacteria, and yeast isolated from a baked loaf.

As shown in FIG. 19, the aerobic bacteria, anaerobic bacteria and yeast demonstrated average log CFUs/g±SD of 9.33±0.1, 9.37±0.1, and 5.0±0.12, respectively. In total, an average log CFU of 23.7/g (equivalent to 4.6 billion CFUs/core) was retrieved from the bread. The results demonstrate that the microbial stains in the probiotic survived baking at 350° F.

INCORPORATION BY REFERENCE

The entire disclosure of each of the patent and scientific documents referred to herein is incorporated by reference herein for all purposes.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

What is claimed is:

1. A method of improving nutrient absorption and inhibiting biofilm in a subject, the method comprising consumption by, or administration to, the subject of a probiotic composition comprising (i) an isolated non-pathogenic fungal strain *Saccharomyces boulardii*; (ii) isolated non-pathogenic bacterial strains comprising *Lactobacillus rhamnosus, Bifidobacterium breve*, and *Lactobacillus acidophilus*; and (iii) an enzyme, thereby improving nutrient absorption and inhibiting biofilm in the subject.

2. The method of claim 1, wherein the enzyme is selected from the group consisting of amylase, cellulase, hemicellulase, lysozyme, pectinase, DNase I, *Serratia* peptidase or Serratiopeptidase, hemicellulase/pectinase complex, β-1,3-glucanase, acid protease, alkaline protease, glucoamylase, endoglucanase, xylanase, lipase, lysozyme, protease/peptidase complex, dipeptidyl peptidase IV (DPP-IV), chitosanase, bromelain, papain, kiwi protease actinidin, and phytase.

3. The method of claim 2, wherein the enzyme is a plant-derived protease.

4. The method of claim 2, wherein the probiotic composition comprises at least one additional different non-pathogenic bacterial strain.

5. The method of claim 2, wherein an additional non-pathogenic bacterial strain is present in the composition and is *Lactobacillus reuteri*.

6. The method of claim 2, wherein the enzyme is an amylase selected from the group consisting of *Bacillus stearothermophilus* amylase, *Bacillus amyloliquefaciens* amylase, *Bacillus subtilis* amylase, and *Bacillus licheniformi* amylase.

7. The method of claim 5, wherein the probiotic composition is formulated as a granulate, pellet, or powder.

8. The method of claim 7, wherein the probiotic composition is formulated as a powder coated with hydroxypropyl methylcellulose.

9. The method of claim 2, wherein the probiotic composition comprises from about 10 billion to about 40 billion colony forming units of the non-pathogenic bacterial strain(s).

10. The method of claim 2, wherein the probiotic composition comprises from about 1 billion to about 10 billion colony forming units of the non-pathogenic fungal strains.

11. The method of claim 10, wherein the probiotic composition comprises about 15 billion colony forming units of *Bifidobacterium breve*, about 10 billion colony forming units of *Lactobacillus rhamnosus*, about 3.5 billion colony forming units of *Saccharomyces boulardii*, and about 1.5 billion colony forming units of *Lactobacillus acidophilus*.

12. The method of claim 2, wherein the probiotic composition is freeze-dried or spray dried.

13. The method of claim 1, wherein the enzyme is an amylase.

14. The method of claim 1, wherein the enzyme is a plant-derived protease.

15. The method of claim 1, wherein the probiotic composition further comprises at least one additional different non-pathogenic bacterial strain.

16. The method of claim 1, wherein an additional non-pathogenic bacterial strain is present in the composition and is *Lactobacillus reuteri*.

17. The method of claim 1, wherein the enzyme is an amylase selected from the group consisting of *Bacillus stearothermophilus* amylase, *Bacillus amyloliquefaciens* amylase, *Bacillus subtilis* amylase, and *Bacillus licheniformi* amylase.

18. The method of claim 1, wherein the probiotic composition comprises from about 10 billion to about 40 billion colony forming units of the non-pathogenic bacterial strain(s).

19. The method of claim 1, wherein the probiotic composition comprises from about 1 billion to about 10 billion colony forming units of the non-pathogenic fungal strain(s).

20. The method of claim 1, wherein the probiotic composition is in a food product that is baked.

* * * * *